(12) United States Patent
Wagner et al.

(10) Patent No.: US 8,703,793 B2
(45) Date of Patent: Apr. 22, 2014

(54) TRICYCLIC PYRIDINE DERIVATIVES, MEDICAMENTS CONTAINING SUCH COMPOUNDS, THEIR USE AND PROCESS FOR THEIR PREPARATION

(75) Inventors: Holger Wagner, Mettenberg (DE); Daniela Berta, Milan (IT); Riccardo Giovannini, Verona (IT); Alessandro Mazzacani, Brighton (GB); Ruediger Streicher, Biberach (DE); Klaus Fuchs, Mittelbiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 162 days.

(21) Appl. No.: 12/920,722

(22) PCT Filed: Mar. 2, 2009

(86) PCT No.: PCT/EP2009/052459
§ 371 (c)(1),
(2), (4) Date: Oct. 12, 2010

(87) PCT Pub. No.: WO2009/109549
PCT Pub. Date: Sep. 11, 2009

(65) Prior Publication Data
US 2011/0021550 A1    Jan. 27, 2011

(30) Foreign Application Priority Data

Mar. 5, 2008 (EP) .................................... 08152288
Jul. 29, 2008 (EP) .................................... 08161366

(51) Int. Cl.
*A61K 31/4355* (2006.01)
*C07D 491/048* (2006.01)

(52) U.S. Cl.
USPC ........................................... 514/291; 546/89

(58) Field of Classification Search
USPC ........................................... 546/89; 514/291
See application file for complete search history.

(56) References Cited

U.S. PATENT DOCUMENTS

| 4,798,619 | A | 1/1989 | Los |
| 5,932,587 | A | 8/1999 | Schmeck et al. |
| 5,977,136 | A | 11/1999 | Di Fabio et al. |
| 2002/0062024 | A1 | 5/2002 | Stoltefuss et al. |
| 2003/0191306 | A1 | 10/2003 | Sikorski et al. |
| 2005/0043341 | A1 | 2/2005 | Gielen et al. |
| 2008/0194609 | A1 | 8/2008 | Bischoff et al. |
| 2008/0255068 | A1 | 10/2008 | Bischoff et al. |
| 2011/0021550 | A1 | 1/2011 | Wagner et al. |
| 2012/0046304 | A1 | 2/2012 | Wagner et al. |
| 2012/0053197 | A1 | 3/2012 | Wagner et al. |
| 2013/0053404 | A1 | 2/2013 | Wagner et al. |
| 2013/0210850 | A1 | 8/2013 | Trieselmann et al. |
| 2013/0210851 | A1 | 8/2013 | Ostermeier et al. |

FOREIGN PATENT DOCUMENTS

| CA | 2302350 | A1 | 3/1999 |
| EP | 0818197 | A1 | 1/1998 |
| WO | 9002129 | A1 | 3/1990 |
| WO | 9712870 | A1 | 4/1997 |
| WO | 9911629 | A1 | 3/1999 |
| WO | 9914215 | A1 | 3/1999 |
| WO | 03028727 | A1 | 4/2003 |
| WO | 2006024517 | A1 | 3/2006 |
| WO | 2006063828 | A1 | 6/2006 |
| WO | 2006072362 | A1 | 7/2006 |
| WO | 2009109549 | A1 | 9/2009 |
| WO | 2011101424 | A1 | 8/2011 |
| WO | 2012110599 | A1 | 8/2012 |

OTHER PUBLICATIONS

Rano, T.A. et al., "Design and synthesis of potent inhibitors of cholesteryl ester transfer protein (CETP) exploiting a 1,2,3,4-tetrahydroquinoline platform." Biorganic and Medicinal Chemistry Letters, Vo. 19, No. 9, May 1, 2009, p. 2456-2460.

Tamura Y. et al., A Synthesis of 5-Amino- and 5-Hydroxy-1-ethyl-1,4-dihydrio-4-oxo-3-quinolinecarboxylic acides and their derivatives:. Journal of Heterocyclic Chemistry, vol. 19, 1982, p. 289-296.

Torii, S. et al., "A Facile Synthesis of Polyfunctionally Substituted Phroidines from Ethoxycarbonylmalonaldehyde". Synthesis, Communications. May 1986, p. 400-402.

Vasil'ev, A.N. et al., "Reduction of Alkyl-2-amino-5,6-dialkyl-3-cyanopyridine-4-carboxylates". Russian Journal of Organic Chemistry, vol. 41, No. 2, 2005, p. 288-291.

International Search Report for PCT/EP2009/052459 mailed May 4, 2009.

*Primary Examiner* — Rita Desai
(74) *Attorney, Agent, or Firm* — Michael P. Morris; David L. Kershner; Usha R. Patel

(57) ABSTRACT

Compounds of formula (I) wherein the groups R1 to R8 have the meanings indicated in the description, the tautomers, the stereoisomers, the mixtures thereof and the salts thereof have valuable pharmacological properties, which make them useful for the treatment of cardiovascular and related disorders.

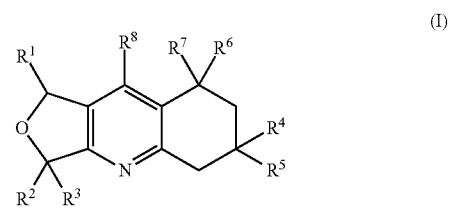

(I)

11 Claims, No Drawings

… (1)

TRICYCLIC PYRIDINE DERIVATIVES, MEDICAMENTS CONTAINING SUCH COMPOUNDS, THEIR USE AND PROCESS FOR THEIR PREPARATION

FIELD OF APPLICATION OF THE INVENTION

The present invention relates to 1,3,5,6,7,8-hexahydro-furo[3,4-b]quinoline derivatives derived from the following chemical scaffold which is structurally defined by the formula I

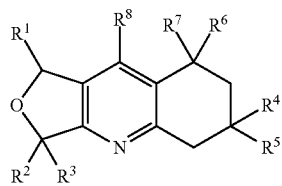

wherein the groups R1 to R8 are as defined hereinafter, including the tautomers, the stereoisomers, the mixtures thereof and the salts thereof. These compounds according to the invention can be used in the pharmaceutical industry for the production of pharmaceutical compositions. The invention further relates to pharmaceutical compositions containing a compound according to the invention as well as the use of a compound according to the invention for preparing a pharmaceutical composition for the treatment of cardiovascular disorders. In addition, the invention relates to processes for preparing compounds and pharmaceutical compositions according to the invention.

KNOWN TECHNICAL BACKGROUND

In the literature, compounds which have an inhibitory effect on the enzyme cholesterol ester transfer protein (CETP) are proposed for the treatment of the cardiovascular disorders, in particular hypolipoproteinemia, dyslipidimia, hypertriglyceridimia, hyperlipidimia, hypercholesterolemia and atherosclerosis.

Compounds from various chemical classes are described in the literature as inhibitors of CETP (WO 98/35937, WO 00/017164, WO 05/100298, US2002120011, US2002177708, WO 00/18724). Also, substituted tetrahydroquinoline derivatives (WO 06/063828) have been described, however substituted 1,3,5,6,7,8-hexahydro-furo[3,4-b]quinoline derivatives defined by formula I have not yet been described for the inhibition of CETP.

AIM OF THE INVENTION

The aim of the present invention is to find new 1,3,5,6,7,8-hexahydro-furo[3,4-b]quinoline derivatives, particularly those which are active with regard to the enzyme CETP. A further aim of the present invention is to discover 1,3,5,6,7,8-hexahydro-furo[3,4-b]quinoline derivatives which have an inhibitory effect on the enzyme CETP in vitro and/or in vivo and possess suitable pharmacological and pharmacokinetic properties to use them as medicaments.

A further aim of the present invention is to provide new pharmaceutical compositions which are suitable for the prevention and/or treatment of cardiovascular disorders, particularly hypolipoproteinemia, dyslipidimia, hypertriglyceridimia, hyperlipidimia, hypercholesterolemia and atherosclerosis.

Other aims of the present invention will become apparent to the skilled man directly from the foregoing and following remarks.

DESCRIPTION OF THE INVENTION

It has now been found, that the compounds, which are described in greater details below, have surprising and particularly advantageous properties.

The invention thus relates in a first aspect (aspect A) to compounds of formula I

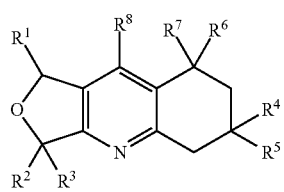

wherein
$R^1$ is phenyl substituted by $R^{11}$ and/or $R^{12}$ and/or $R^{13}$, or pyridyl substituted by $R^{11}$ and/or $R^{12}$ and/or $R^{13}$, in which
$R^{11}$ is halogen, cyano, 1-4C-alkyl, 3-7C-cycloalkyl, 3-7C-cycloalkyl-1-4C-alkyl, 3-7C-cycloalkoxy, 3-7C-cycloalkyl-1-4C-alkoxy, 1-4C-alkoxy, completely or partially fluorine-substituted 1-4C-alkyl, or completely or partially fluorine-substituted 1-4C-alkoxy,
$R^{12}$ is halogen, cyano, 1-4C-alkyl, 1-4C-alkoxy, completely or partially fluorine-substituted 1-4C-alkyl, or completely or partially fluorine-substituted 1-4C-alkoxy,
$R^{13}$ is halogen,
$R^2$ is hydrogen, or 1-4C-alkyl,
$R^3$ is hydrogen, or 1-4C-alkyl,
or $R^2$ and $R^3$ together and with inclusion of the carbon atom, to which they are attached, form a 3-7C-cycloalkane ring, said 3-7C-cycloalkane ring being optionally substituted by halogen, cyano, 1-4C-alkyl, 1-4C-alkoxy, completely or partially fluorine-substituted 1-4C-alkyl, or completely or partially fluorine-substituted 1-4C-alkoxy,
$R^4$ is hydrogen, or 1-4C-alkyl,
$R^5$ is hydrogen, or 1-4C-alkyl,
or $R^4$ and $R^5$ together and with inclusion of the carbon atom, to which they are attached, form a 3-7C-cycloalkane ring, said 3-7C-cycloalkane ring being optionally substituted by halogen, cyano, 1-4C-alkyl, 1-4C-alkoxy, completely or partially fluorine-substituted 1-4C-alkyl, or completely or partially fluorine-substituted 1-4C-alkoxy,
$R^6$ is hydroxyl, halogen, 1-4C-alkoxy, or completely or partially fluorine-substituted 1-4C-alkoxy,
$R^7$ is hydrogen, or 1-4C-alkyl,
or $R^6$ and $R^7$ taken together and with the carbon atom, to which they are bonded, form a carbonyl (>C=O) or oxime (>C=N—OH) group,
$R^8$ is 1-9C-alkyl, $R^{80}$, or $R^{80}$-1-4C-alkyl, in which
$R^{80}$ is 3-7C-cycloalkyl, 3-7C-cycloalkenyl, 3- to 7-membered heterocycloalkyl, 3- to 7-membered heterocycloalkenyl, phenyl, or 5- or 6-membered heteroaryl, said $R^{80}$ being optionally substituted by $R^{81}$ and/or $R^{82}$, in which
$R^{81}$ is halogen, cyano, 1-4C-alkyl, 3-7C-cycloalkyl, 1-4C-alkoxy, 3-7C-cycloalkoxy, 1-4C-alkylcarbonyl, 1-4C-alkoxycarbonyl, completely or partially fluorine-substituted 1-4C-alkyl, or completely or partially fluorine-substituted 1-4C-alkoxy, wherein each of said 1-4C-alkyl, 1-4C-alkoxy, 1-4C-alkylcarbonyl and 1-4C-alkoxycarbonyl may be optionally substituted by $R^{810}$, in which $R^{810}$ is 3-7C-cycloalkyl, 3-7C-cycloalkenyl, 3- to 7-membered heterocycloalkyl, 3- to 7-membered heterocycloalkenyl, phenyl, or 5- or 6-membered heteroaryl, said $R^{810}$ being optionally substituted by $R^{811}$ and/or $R^{812}$, in which $R^{811}$ is halogen, cyano, 1-4C-alkyl, 1-4C-alkoxy, completely or partially fluorine-substituted 1-4C-alkyl, or completely or partially fluorine-substituted 1-4C-alkoxy, $R^{812}$ is halogen, cyano, 1-4C-alkyl, 1-4C-alkoxy, completely or partially fluorine-substituted 1-4C-alkyl, or completely or partially fluorine-substituted 1-4C-alkoxy, $R^{82}$ is halogen, cyano, 1-4C-alkyl, 1-4C-alkoxy, completely or partially fluorine-substituted 1-4C-alkyl, or completely or partially fluorine-substituted 1-4C-alkoxy, the tautomers, the stereoisomers, the mixtures thereof and the salts thereof.

The invention further relates in a second aspect (aspect B), which is an embodiment of aspect A, to compounds of formula I wherein $R^1$ is phenyl substituted by $R^{11}$ and/or $R^{12}$ and/or $R^{13}$, or pyridyl substituted by $R^{11}$ and/or $R^{12}$ and/or $R^{13}$, in which $R^{11}$ is halogen, trifluoromethyl, 1-4C-alkyl, 1-4C-alkoxy, or completely or predominantly fluorine-substituted 1-4C-alkoxy, $R^{12}$ is halogen, trifluoromethyl, 1-4C-alkyl, 1-4C-alkoxy, or completely or predominantly fluorine-substituted 1-4C-alkoxy, $R^{13}$ is halogen, $R^2$ is hydrogen, or 1-4C-alkyl, $R^3$ is hydrogen, or 1-4C-alkyl, or $R^2$ and $R^3$ together and with inclusion of the carbon atom, to which they are attached, form a 3-7C-cycloalkane ring, $R^4$ is hydrogen, or 1-4C-alkyl, $R^5$ is hydrogen, or 1-4C-alkyl, or $R^4$ and $R^5$ together and with inclusion of the carbon atom, to which they are attached, form a 3-7C-cycloalkane ring, $R^6$ is hydroxyl, halogen, 1-4C-alkoxy, or completely or predominantly fluorine-substituted 1-4C-alkoxy, $R^7$ is hydrogen, or 1-4C-alkyl, or $R^6$ and $R^7$ taken together and with the carbon atom, to which they are bonded, form a carbonyl (>C=O) or oxime (>C=N—OH) group, $R^8$ is 1-4C-alkyl, 3-7C-cycloalkyl, or phenyl substituted by $R^{81}$ and/or $R^{82}$, in which $R^{81}$ is halogen, trifluoromethyl, 1-4C-alkyl, 1-4C-alkoxy, or completely or predominantly fluorine-substituted 1-4C-alkoxy, $R^{82}$ is halogen, trifluoromethyl, 1-4C-alkyl, 1-4C-alkoxy, or completely or predominantly fluorine-substituted 1-4C-alkoxy, the tautomers, the stereoisomers thereof, the mixtures thereof and the salts thereof.

The compounds of general formula I according to the invention and the physiologically acceptable salts thereof have valuable pharmacological properties, particularly an inhibitory effect on the enzyme cholesteryl ester transfer protein (CETP).

The present invention also relates to the physiologically acceptable salts of the compounds of formula I according to the invention with inorganic or organic acids.

This invention also relates to pharmaceutical compositions, comprising at least one compound of formula I according to the invention or a physiologically acceptable salt thereof, optionally together with one or more inert carriers and/or diluents.

This invention also relates to the use of at least one compound of formula I according to the invention or one of the physiologically acceptable salts thereof for preparing a pharmaceutical composition which is suitable for the treatment and/or prevention of diseases or conditions which can be influenced by inhibiting the enzyme cholesteryl ester transfer protein (CETP), such as e.g. those diseases and conditions mentioned herein.

This invention also relates to the use of at least one compound of formula I according to the invention or one of the physiologically acceptable salts thereof for preparing a pharmaceutical composition which is suitable for the treatment and/or prevention of cardiovascular disorders.

This invention also relates to the use of at least one compound of formula I according to the invention or one of the physiologically acceptable salts thereof for preparing a pharmaceutical composition for inhibiting the enzyme cholesteryl ester transfer protein (CETP).

This invention also relates to a compound according to the present invention which is suitable for use in therapy and/or prophylaxis, e.g. for the treatment and/or prevention of diseases or conditions which can be influenced by inhibiting the enzyme cholesteryl ester transfer protein (CETP), e.g. cardiovascular and/or related disorders, such as e.g. any of those diseases and conditions mentioned herein.

This invention also relates to a compound according to the present invention which is suitable for inhibiting the enzyme cholesteryl ester transfer protein (CETP).

The invention further relates to a process for preparing a pharmaceutical composition according to the invention, comprising incorporating a compound of formula I according to the invention or one of the physiologically acceptable salts thereof in one or more inert carriers and/or diluents preferably by a non-chemical method.

The present invention also relates to a method for treating and/or preventing a disease or condition which can be influenced by inhibiting the enzyme cholesteryl ester transfer protein (CETP), e.g. a cardiovascular or related disorder, such as e.g. any of those diseases and conditions mentioned herein, in a mammal comprising administering to a mammal in need thereof a compound of formula I according to the invention or one of the physiologically acceptable salts thereof.

The present invention also relates to a process for preparing the compounds of general formula I according to the invention.

The present invention also relates to intermediates which are useful for synthesizing compounds of general formula I according to the invention.

Some terms used above and below to describe the compounds according to the invention will now be defined more closely:

As used herein, the term "alkyl" alone or as part of another group refers to both branched and straight chain saturated aliphatic hydrocarbon groups having the specified numbers of carbon atoms, such as for example:

1-9C-Alkyl within the meaning of this invention is a straight-chain or branched alkyl radical having 1 to 9 carbon atoms. Examples are the nonyl-, octyl-, heptyl- (such as e.g. isoheptyl (5-methylhexyl) or the like), hexyl- (such as e.g. isohexyl (4-methylpentyl), neohexyl (3,3-dimethylbutyl) or the like), and pentyl-isomers (such as e.g. isopentyl (3-methylbutyl), neopentyl (2,2-dimethylpropyl) or the like) as well as the butyl, isobutyl, sec-butyl, tert-butyl, isopropyl, propyl, ethyl and methyl radicals.

1-4C-Alkyl within the meaning of this invention is a straight-chain or branched alkyl radical having 1 to 4 carbon atoms. Examples are the butyl, isobutyl, sec-butyl, tert-butyl, propyl, isopropyl, ethyl and methyl radicals.

Halogen within the meaning of the present invention refers to fluorine, chlorine, bromine and iodine, of which fluorine, chlorine and bromine are more worthy to be mentioned.

1-4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy, ethoxy and methoxy radicals, of which propoxy, isopropoxy, and, particularly, ethoxy and methoxy are more worthy to be mentioned.

The term "cycloalkyl" or "cycloalkane" alone or as part of another group refers to a monocyclic saturated aliphatic hydrocarbon group having the specified numbers of ring carbon atoms, such as for example:

3-7C-Cycloalkyl stands for cyclopropyl, cyclobutyl, cyclopentyl, cyclohexyl and cycloheptyl, of which cyclopropyl, cyclobutyl, cyclopentyl and cyclohexyl are more worthy to be mentioned.

A 3-7C-Cycloalkane ring stands for a cyclopropane, cyclobutane, cyclopentane, cyclohexane and cycloheptane ring, of which cyclopropane, cyclobutane, cyclopentane and cyclohexane are more worthy to be mentioned.

3-7C-Cycloalkoxy stands for cyclopropoxy, cyclobutoxy, cyclopentoxy, cyclohexoxy and cycloheptoxy, of which cyclopropoxy, cyclobutoxy, cyclopentoxy and cyclohexoxy are more worthy to be mentioned.

3-7C-Cycloalkyl-1-4C-alkyl stands for one of the abovementioned 1-4C-alkyl radicals which is substituted by one of the abovementioned 3-7C-cycloalkyl radicals, such as e.g. 3-7C-cycloalkyl-methyl or 2-(3-7C-cycloalkyl)-ethyl. Examples which may be mentioned are the cyclopropylmethyl, cyclopentylmethyl, cyclohexylmethyl and 2-cyclohexylethyl radicals.

3-7C-Cycloalkyl-1-4C-alkoxy stands for one of the abovementioned 1-4C-alkoxy radicals which is substituted by one of the abovementioned 3-7C-cycloalkyl radicals, such as e.g. 3-7C-cycloalkyl-methoxy or 2-(3-7C-cycloalkyl)-ethoxy. Examples which may be mentioned are the cyclopropylmethoxy, cyclopentylmethoxy, cyclohexylmethoxy and 2-cyclohexylethoxy radicals.

3-7C-Cycloalkenyl refers to a monocyclic unsaturated, but not aromatic hydrocarbon group having the specified numbers of ring carbon atoms. Examples of 3-7C-cycloalkenyl include, without being restricted to, cyclopentenyl, cyclohexenyl, 1,3-cyclopentadienyl, 1,3-cyclohexadienyl and 1,4-cyclohexadienyl.

1-4C-Alkoxycarbonyl represents a radical which, in addition to the carbonyl group, contains one of the abovementioned 1-4C-alkoxy radicals. Examples which may be mentioned are the methoxycarbonyl, the ethoxycarbonyl and the isopropoxycarbonyl radicals.

1-4C-Alkylcarbonyl represents a radical which, in addition to the carbonyl group, contains one of the abovementioned 1-4C-alkyl radicals. Examples which may be mentioned are the methylcarbonyl (i.e. acetyl), the ethylcarbonyl and the isopropylcarbonyl radicals.

Completely or partially fluorine-substituted 1-4C-alkyl alone or as part of another group is, for example, the 2,2,3,3,3-pentafluoropropyl, the perfluoroethyl, the 1,2,2-trifluoroethyl, the 1,1,2,2-tetrafluoroethyl, the 2,2,2-trifluoroethyl, the trifluoromethyl and the difluoromethyl as well as the 2-fluoroethyl and the 2,2-difluoroethyl radical, of which the trifluoromethyl radical is to be emphasized.

Completely or predominantly fluorine-substituted 1-4C-alkoxy is, for example, the 2,2,3,3,3-pentafluoropropoxy, the perfluoroethoxy, the 1,2,2-trifluoroethoxy, the 1,1,2,2-tetrafluoroethoxy, the 2,2,2-trifluoroethoxy, the trifluoromethoxy and the difluoromethoxy radical, of which the difluoromethoxy and, particularly, the trifluoromethoxy radicals are to be emphasized. "Predominantly" in this connection means that more than half of the hydrogen atoms of the 1-4C-alkoxy groups are replaced by fluorine atoms.

The term 5- or 6-membered monocyclic heteroaryl group as used herein refers to an aromatic monocyclic heterocycle ring of 5 or 6 ring members comprising 1, 2, 3 or 4 heteroatoms selected from nitrogen, oxygen and sulphur, wherein the nitrogen and sulphur heteroatoms may be optionally oxidized. Representative 5-membered monocyclic heteroaryl groups may include, without being limited to furyl, thienyl, pyrrolyl, oxazoly, imidazolyl, thiazolyl, pyrazolyl, isoxazolyl, isothiazolyl, triazolyl (including 1,2,3-triazoly and 1,2,4-triazolyl), oxadiazolyl (including 1,2,3-oxadiazolyl, 1,2,4-oxadiazolyl and 1,3,4-oxadiazolyl), thiadiazolyl (including 1,2,3-thiadiazolyl, 1,2,4-thiadiazolyl and 1,3,4-thiadiazolyl) and tetrazolyl. Representative 6-membered monocyclic heteroaryl groups may include, without being limited to pyridyl, pyrazinyl, pyridazinyl and pyrimidinyl, as well as N-oxy-pyridyl.

The term 3- to 7-membered heterocycloalkyl as used herein refers to a fully saturated monocyclic ring of 3 to 7 ring members comprising 1 or 2 heteroatoms selected from nitrogen, oxygen and sulphur, wherein the nitrogen and sulphur heteroatoms may be optionally oxidized. Representative 3- to 7-membered heterocycloalkyl groups may include, without being limited to aziridinyl, azetidinyl, pyrrolidinyl, piperidinyl, piperazinyl, morpholinyl, thiomorpholinyl, S-oxy-thiomorpholinyl, S,S-dioxy-thiomorpholinyl, tetrahydrofuranyl, tetrahydrothienyl, tetrahydropyranyl, tetrahydrothiopyranyl, S-oxy-tetrahydrothiopyranyl, S,S-dioxy-tetrahydrothiopyranyl, homopiperidinyl and homopiperazinyl.

The term 3- to 7-membered heterocycloalkenyl as used herein refers to an unsaturated, but not aromatic monocyclic ring of 3 to 7 ring members comprising 1 or 2 heteroatoms selected from nitrogen, oxygen and sulphur, wherein the nitrogen and sulphur heteroatoms may be optionally oxidized. A representative 6-membered heterocycloalkenyl group may be, without being limited to pyranyl, e.g. 2- or 4-pyranyl.

The term $R^{80}$-1-4C-alkyl as used herein stands for one of the abovementioned 1-4C-alkyl radicals which is substituted by the radical $R^{80}$. An example of $R^{80}$-1-4C-alkyl more worthy to be mentioned is the $R^{80}$-methyl radical (i.e. $R^{80}$—$CH_2$—).

In general, unless otherwise mentioned, the heterocyclic radicals mentioned herein include all the possible isomeric forms thereof, e.g. the positional isomers thereof. Thus, for example, the term pyridyl includes pyridine-2-yl, pyridine-3-yl and pyridine-4-yl.

Further, constituents which are optionally substituted as stated herein, may be substituted, unless otherwise noted, at any possible position.

Further, unless otherwise noted, the carbocyclic radicals mentioned herein may be substituted by their given substituents or parent molecular groups at any possible position.

Further, the heterocyclic groups mentioned herein may be substituted by their given substituents or parent molecular groups, unless otherwise noted, at any possible position, such as e.g. at any substitutable ring carbon or ring nitrogen atom.

Further, unless otherwise noted, rings containing quaternizable amino- or imino-type ring nitrogen atoms (—N═) may be preferably not quaternized on these amino- or imino-type ring nitrogen atoms.

If residues, substituents or groups occur several times in a compound they may have the same or different meanings.

Unless otherwise stated, the groups, residues and substituents, particularly $R^1$ to $R^8$, $R^{11}$ to $R^{13}$, $R^{81}$ and $R^{82}$, $R^{810}$ to $R^{812}$, and $R^{80}$ are defined as above and below.

The substituents $R^{11}$, $R^{12}$ and $R^{13}$ as well as $R^{81}$ and $R^{82}$ as well as $R^{811}$ and $R^{812}$ can be attached in the ortho, meta or para position with respect to the binding position in which the phenyl ring is bonded to the scaffold ring system, whereby emphasis is given to the attachment in the meta or in the para position.

Salts of the compounds of formula I according to the present invention include—depending upon their nature—all acid addition salts and all salts with bases, especially all pharmaceutically acceptable inorganic and organic acid addition salts and salts with bases. Particular mention may be made of the physiologically acceptable inorganic and organic acid addition salts and bases customarily used in pharmacy. The salts include water-insoluble and, particularly, water-soluble salts.

Inorganic acids suitable for forming pharmaceutically acceptable acid addition salts include, by way of example and not limitation, hydrochloric acid, hydrobromic acid, phosphoric acid, sulfuric acid, and the like. Organic acids suitable for forming pharmaceutically acceptable acid addition salts include, by way of example and not limitation, citric acid, maleic acid, fumaric acid, succinic acid, lactic acid, tartaric acid, methanesulfonic acid, and the like.

Thus, pharmaceutically acceptable acid addition salts with inorganic or organic acids include, by way of example and not limitation, hydrochlorides, hydrobromides, phosphates, sulfates, citrates, maleates, fumarates, succinates, lactates, tartrates, methanesulfonates (mesylates), and the like.

Salts which are unsuitable for pharmaceutical uses but which can be employed, for example, for the isolation or purification of free compounds of formula I or their pharmaceutically acceptable salts, are also included.

Pharmaceutically non-acceptable salts, which can be obtained, for example, as process products during the preparation of the compounds according to this invention on an industrial scale, are converted into pharmaceutically acceptable salts by processes known to the person skilled in the art.

All isomeric forms (especially all regio- and stereoisomeric forms, e.g. all chiral, enantiomeric, diastereomeric, racemic forms, tautomeric and all geometric isomeric forms) of a compound of formula I are intended within this invention, unless the specific isomer form is specifically indicated. Obviously, the isomer which is pharmacologically most effective and most free from side effects is preferred.

It will be appreciated that the compounds of the present invention contain at least one asymmetrically substituted carbon atom, and may be isolated in optically active or racemic forms.

The compounds of formula I are chiral compounds having chiral centers at least in position 1 as well as, depending on the meanings of $R^2$ and $R^3$, in position 3, depending on the meanings of $R^4$ and $R^5$, in position 6 and, depending on the meanings of $R^6$ and $R^7$, in position 8.

Numbering:

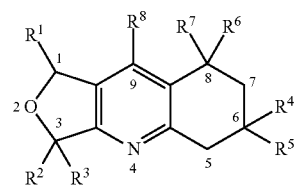

The invention includes all conceivable stereoisomers, like e.g. diastereomers and enantiomers, in substantially pure form, in enriched form (e.g. substantially free of any or all other undesired diastereomers and/or enantiomers) as well as in any mixing ratio, including the racemic forms, as well as the salts thereof.

In some instances, the amount of an undesired stereoisomer as established using conventional analytical methods may be less than 50%, 40%, 30%, 20% or 10%, for example, 8%, 6%, 4%, 2%, 1%, 0.5% or even less. The amount of a desired stereoisomer as established using conventional analytical methods may be more than 50%, 60%, 70%, 80% or 90%, for example, 92%, 94%, 96%, 98%, 99%, 99.5% or even more.

Each of the stereogenic centers present in said stereoisomers may have the absolute configuration R or the absolute configuration S (according to the rules of Cahn, Ingold and Prelog). Accordingly, the stereoisomers (1R,3R,6R,8R), (1R,3R,6R,8S), (1R,3R,6S,8R), (1R,3S,6R,8R), (1S,3R,6R,8R), (1S,3S,6R,8R), (1S,3R,6S,8R), (1S,3R,6R,8S), (1S,3S,6S,8S), (1S,3S,6S,8R), (1S,3S,6R,8S), (1S,3R,6S,8S), (1R,3S,6S,8S), (1R,3R,6S,8S), (1R,3S,6R,8S) and (1R,3S,6S,8R), wherein the numbers refer to the atoms indicated in formula I above, and the salts thereof, are part of the invention.

A particular embodiment of the invention refers hereby to those compounds of formula I as well as the salts thereof, which have with respect to position 8 the same configuration as shown in formula I*

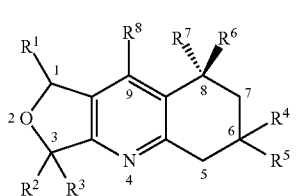

If, for example, in compounds of formula I* $R^6$ has the meaning hydroxyl and $R^7$ has the meaning hydrogen, then the configuration—according to the rules of Cahn, Ingold and Prelog—is S in the 8 position.

The substituents $R^1$ and $R^2$ of compounds of formula I* can be located at the same side of the plane defined by the dihydrofurane ring, then $R^1$ and $R^2$ are arranged in cis configuration relative to each other; or $R^1$ and $R^2$ can be located at the opposite side of the plane defined by the dihydrofurane ring, then $R^1$ and $R^2$ are arranged in trans configuration relative to each other.

For example, when in compounds of formula I* according to this particular embodiment $R^6$ is hydroxyl, $R^7$ is hydrogen, both $R^4$ and $R^5$ are the same (e.g. both are methyl) or form a cycloalkane ring (e.g. cyclopropane, cyclobutane or cyclopentane), $R^2$ is different from hydrogen and $R^3$ is hydrogen, these compounds include four diastereomers (two forms with trans configuration of $R^1$ and $R^2$ to each other, and two forms with cis configuration of $R^1$ and $R^2$ to each other) which can be represented by structural formulae Ia*-Id*, below:

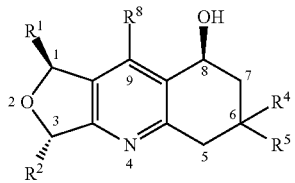
(Ia*)

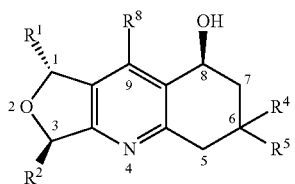
(Ib*)

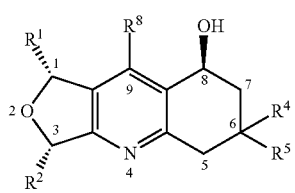
(Ic*)

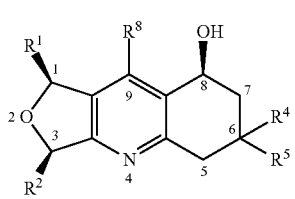
(Id*)

If, for more detailed example, in compounds of formula Ia* $R^1$ is 4-trifluoromethyl-phenyl and $R^2$ is methyl, then the configuration—according to the rules of Cahn, Ingold and Prelog—is S in the 1 position and S in the 3 position, then the stereochemistry in said compounds of formula Ia* is conventionally named as (1S,3S,8S) configuration.

For other example, when in compounds of formula I* according to this particular embodiment $R^6$ is hydroxyl, $R^7$ is hydrogen, both $R^4$ and $R^5$ are the same (e.g. both are methyl) or form a cycloalkane ring (e.g. cyclopropane, cyclobutane or cyclopentane), and both $R^2$ and $R^3$ are the same (e.g. both are methyl) or form a cycloalkane ring (e.g. cyclopentane or cyclohexane), these compounds include two diastereomers which can be represented by structural formulae Ie*-If*, below:

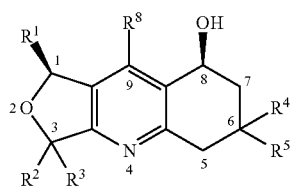
(Ie*)

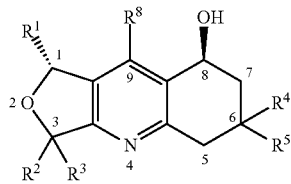
(If*)

If, for more detailed example, in compounds of formula Ie* $R^1$ is 4-trifluoromethyl-phenyl, $R^2$ is methyl and $R^3$ is methyl or $R^2$ and $R^3$ together form a cyclopentane or cyclohexane ring, then the configuration—according to the rules of Cahn, Ingold and Prelog—is S in the 1 position, then the stereochemistry in said compounds of formula Ie* is conventionally named as (1S,8S) configuration.

Another embodiment of the invention refers to those compounds of formula I as well as the salts thereof, which have with respect to position 8 the same configuration as shown in formula I**

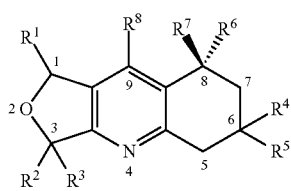
(I**)

If, for example, in compounds of formula I** $R^6$ has the meaning hydroxyl and $R^7$ has the meaning hydrogen, then the configuration—according to the rules of Cahn, Ingold and Prelog—is R in the 8 position.

The substituents $R^1$ and $R^2$ of compounds of formula I** can be located at the same side of the plane defined by the dihydrofurane ring, then $R^1$ and $R^2$ are arranged in cis configuration relative to each other; or $R^1$ and $R^2$ can be located at the opposite side of the plane defined by the dihydrofurane ring, then $R^1$ and $R^2$ are arranged in trans configuration relative to each other.

For example, when in compounds of formula I according to this embodiment $R^6$ is hydroxyl, $R^7$ is hydrogen, both $R^4$ and $R^5$ are the same (e.g. both are methyl) or form a cycloalkane ring (e.g. cyclopropane, cyclobutane or cyclopentane), $R^2$ is different from hydrogen and $R^3$ is hydrogen, these compounds include four diastereomers (two forms with trans configuration of $R^1$ and $R^2$ to each other, and two forms with cis configuration of $R^1$ and $R^2$ to each other) which can be represented by structural formulae Ia-Id**, below:

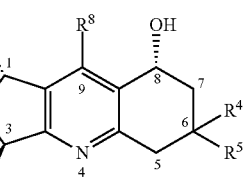
(Ia**)

(Ib**)
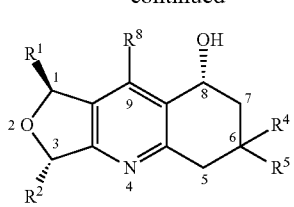

(Ic**)
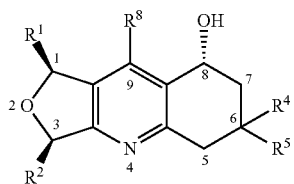

(Id**)
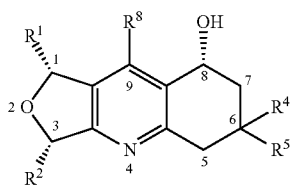

For other example, when in compounds of formula I according to this embodiment R⁶ is hydroxyl, R⁷ is hydrogen, both R⁴ and R⁵ are the same (e.g. both are methyl) or form a cycloalkane ring (e.g. cyclopropane, cyclobutane or cyclopentane), and both R² and R³ are the same (e.g. both are methyl) or form a cycloalkane ring (e.g. cyclopentane or cyclohexane), these compounds include two diastereomers which can be represented by structural formulae Ie-If**, below:

(Ie**)
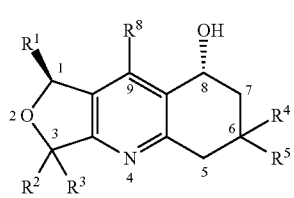

(If**)
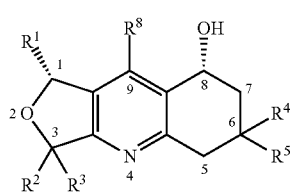

Thus, the compounds of formula I from above examples containing three chiral centers include four diastereomeric racemates (together 8 stereoisomers), two racemates with trans configuration of R¹ and R² relative to each other (one represented by enantiomers of formulae Ia* and Ia** and the other represented by enantiomers of formulae Ib* and Ib**) and two racemates with cis configuration of R¹ and R² relative to each other (one represented by enantiomers of formulae Ic* and Ic** and the other represented by enantiomers of formulae Id* and Id**).

Thus, the compounds of formula I from above examples containing two chiral centers include two diastereomeric racemates (together 4 stereoisomers), one racemate represented by enantiomers of formulae Ie* and Ie** and the other represented by enantiomers of formulae If* and If**.

Among the compounds of formulae I* and I** according to this invention, compounds of formula I* are more worthy to be mentioned.

Particular compounds of the invention are selected from the formulae Ia*, Ib*, Ic* and Id* as shown herein, especially from formula Ia*.

Other particular compounds of the invention are selected from the formulae Ie* and If* as shown herein, especially from formula Ie*.

More particular compounds of the invention are from formula Ia* as shown herein.

Other more particular compounds of the invention are from formula Ie* as shown herein.

The invention further includes all mixtures of the stereoisomers mentioned herein independent of the ratio, including the racemates.

In general, substantially pure stereoisomers can be obtained according to synthetic principles customary to the skilled person, e.g. by separation of corresponding mixtures, by using stereochemically pure starting materials and/or by stereoselective synthesis.

It is known in the art how to prepare optically active forms, such as by resolution of racemic forms or by synthesis, from optically active starting materials and/or by using chiral reagents.

Enantiomerically pure compounds of this invention can be prepared via asymmetric synthesis, for example by preparation and separation of appropriate diastereoisomeric compounds/intermediates which can be separated by known methods (e.g. by chromatographic separation or (fractional) crystallization from a suitable solvent), and/or by using chiral reaction components (e.g. chiral reagents, chiral catalysts, chiral ligands, chiral synthons, chiral building blocks, or the like).

Further, it is known to the person skilled in the art how to prepare enantiomerically pure compounds from the corresponding racemic mixtures, such as e.g. by chromatographic separation of the corresponding racemic compounds on chiral separating columns; or by resolution of racemic compounds using an appropriate resolving agent; e.g. by means of diastereomeric salt formation of the racemic compounds with optically active acids or bases, subsequent resolution of the salts and release of the desired compound from the salt; or by derivatization of the corresponding racemic compounds with chiral auxiliary reagents, subsequent diastereomer separation and removal of the chiral auxiliary group; by kinetic resolution of a racemate (e.g. by enzymatic resolution); by enantioselective (preferential) crystallization (or crystallization by entrainment) from a conglomerate of enantiomorphous crystals under suitable conditions; or by (fractional) crystallization from a suitable solvent in the presence of a chiral auxiliary.

A closer embodiment of the compounds according to aspect A of this invention refers to those compounds of formula I, wherein R¹ is phenyl substituted by R¹¹ and/or R¹² and/or R¹³, or pyridyl substituted by R¹¹, in which
R¹¹ is fluorine, tert-butyl, trifluoromethyl or trifluoromethoxy,
R¹² is fluorine or trifluoromethyl,
R¹³ is fluorine,
R² is hydrogen, methyl, ethyl, propyl or isopropyl,
R³ is hydrogen, methyl or ethyl, or $R^2$ and $R^3$ together and with inclusion of the carbon atom, to which they are attached, form a cyclopentane or cyclohexane ring,
$R^4$ is hydrogen, methyl, isopropyl or isobutyl,
$R^5$ is hydrogen or methyl,
or $R^4$ and $R^5$ together and with inclusion of the carbon atom, to which they are attached, form a cyclopropane, cyclobutane, cyclopentane or cyclohexane ring,
$R^6$ is hydroxyl, fluorine or methoxy,
$R^7$ is hydrogen or methyl,
or $R^6$ and $R^7$ taken together and with the carbon atom, to which they are bonded, form a carbonyl ($>$C$=$O) or oxime ($>$C$=$N—OH) group,
$R^8$ is 1-4C-alkyl, cyclopropyl, cyclobutyl, cyclopentyl, cyclohexyl, cyclopentenyl, cyclohexenyl, 3- to 7-membered heterocycloalkyl, or phenyl substituted by $R^{81}$ and/or $R^{82}$, in which
$R^{81}$ is fluorine, methyl, trifluoromethyl, methoxy or trifluoromethoxy,
$R^{82}$ is fluorine or trifluoromethyl,
the tautomers, the stereoisomers, the mixtures thereof and the salts thereof.

A yet closer embodiment of the compounds according to aspect A of this invention refers to those compounds of formula I, wherein
$R^1$ is phenyl substituted by $R^{11}$ and/or $R^{12}$ and/or $R^{13}$, or pyridyl substituted by $R^{11}$, in which
$R^{11}$ is fluorine, tert-butyl, trifluoromethyl or trifluoromethoxy,
$R^{12}$ is fluorine or trifluoromethyl,
$R^{13}$ is fluorine,
either
$R^2$ is ethyl, propyl or isopropyl, and
$R^3$ is hydrogen,
or
$R^2$ is methyl, and
$R^3$ is hydrogen,
or
$R^2$ is methyl, and
$R^3$ is methyl,
or
$R^2$ is hydrogen, and
$R^3$ is hydrogen,
or $R^2$ and $R^3$ together and with inclusion of the carbon atom, to which they are attached, form a cyclopentane ring,
or $R^2$ and $R^3$ together and with inclusion of the carbon atom, to which they are attached, form a cyclohexane ring,
either
$R^4$ is isopropyl or isobutyl, and
$R^5$ is hydrogen,
or
$R^4$ is methyl, and
$R^5$ is methyl,
or
$R^4$ is hydrogen, and
$R^5$ is hydrogen,
or $R^4$ and $R^5$ together and with inclusion of the carbon atom, to which they are attached, form a cyclopropane, cyclobutane, cyclopentane or cyclohexane ring,
either
$R^6$ is fluorine or methoxy, and
$R^7$ is hydrogen,
or
$R^6$ is hydroxyl, and
$R^7$ is methyl,
or
$R^6$ is hydroxyl, and $R^7$ is hydrogen,
or $R^6$ and $R^7$ taken together and with the carbon atom, to which they are bonded, form a carbonyl ($>$C$=$O) or oxime ($>$C$=$N—OH) group,
$R^8$ is 1-4C-alkyl, cyclopropyl, cyclobutyl, cyclopentyl, cyclohexyl, cyclopentenyl, cyclohexenyl, tetrahydropyranyl, or phenyl substituted by $R^{81}$ and/or $R^{82}$, in which
$R^{81}$ is fluorine, methyl, trifluoromethyl, methoxy or trifluoromethoxy,
$R^{82}$ is fluorine or trifluoromethyl,
the tautomers, the stereoisomers, the mixtures thereof and the salts thereof.

A still yet closer embodiment of the compounds according to aspect A of this invention refers to those compounds of formula I, wherein
$R^1$ is trifluoromethyl-phenyl,
either
$R^2$ is ethyl, and
$R^3$ is hydrogen,
or
$R^2$ is isopropyl, and
$R^3$ is hydrogen,
or
$R^2$ is methyl, and
$R^3$ is hydrogen,
or
$R^2$ is methyl, and
$R^3$ is methyl,
or $R^2$ and $R^3$ together and with inclusion of the carbon atom, to which they are attached, form a cyclopentane ring,
or $R^2$ and $R^3$ together and with inclusion of the carbon atom, to which they are attached, form a cyclohexane ring,
either
$R^4$ is methyl, and
$R^5$ is methyl,
or $R^4$ and $R^5$ together and with inclusion of the carbon atom, to which they are attached, form a cyclopropane ring,
or $R^4$ and $R^5$ together and with inclusion of the carbon atom, to which they are attached, form a cyclobutane ring,
or $R^4$ and $R^5$ together and with inclusion of the carbon atom, to which they are attached, form a cyclopentane ring,
or $R^4$ and $R^5$ together and with inclusion of the carbon atom, to which they are attached, form a cyclohexane ring,
$R^6$ is hydroxyl,
$R^7$ is hydrogen,
$R^8$ is isopropyl, cyclopropyl, cyclobutyl, cyclopentyl, cyclohexyl, tetrahydropyranyl, or fluorophenyl,
the tautomers, the stereoisomers, the mixtures thereof and the salts thereof.

A closer embodiment of the compounds according to aspect B of this invention refers to those compounds of formula I, wherein
$R^1$ is phenyl substituted by $R^{11}$ and/or $R^{12}$ and/or $R^{13}$, or pyridyl substituted by $R^{11}$, in which
$R^{11}$ is fluorine, tert-butyl, trifluoromethyl or trifluoromethoxy,
$R^{12}$ is fluorine or trifluoromethyl,
$R^{13}$ is fluorine,
$R^2$ is hydrogen, methyl, ethyl, propyl or isopropyl,
$R^3$ is hydrogen, methyl or ethyl,
or $R^2$ and $R^3$ together and with inclusion of the carbon atom, to which they are attached, form a cyclopentane or cyclohexane ring,
$R^4$ is hydrogen, methyl, isopropyl or isobutyl,
$R^5$ is hydrogen or methyl, or $R^4$ and $R^5$ together and with inclusion of the carbon atom, to which they are attached, form a cyclopropane, cyclobutane, cyclopentane or cyclohexane ring,
$R^6$ is hydroxyl, fluorine or methoxy,
$R^7$ is hydrogen or methyl,
or $R^6$ and $R^7$ taken together and with the carbon atom, to which they are bonded, form a carbonyl ($>$C$=$O) or oxime ($>$C$=$N—OH) group,
$R^8$ is 1-4C-alkyl, cyclopropyl, cyclobutyl, cyclopentyl, cyclohexyl, or phenyl substituted by $R^{81}$ and/or $R^{82}$, in which
$R^{81}$ is fluorine, methyl, trifluoromethyl, methoxy or trifluoromethoxy,
$R^{82}$ is fluorine or trifluoromethyl,
the tautomers, the stereoisomers thereof, the mixtures thereof and the salts thereof.

A yet closer embodiment of the compounds according to aspect B of this invention refers to those compounds of formula I, wherein
$R^1$ is phenyl substituted by $R^{11}$ and/or $R^{12}$ and/or $R^{13}$, or pyridyl substituted by $R^{11}$, in which
$R^{11}$ is fluorine, tert-butyl, trifluoromethyl or trifluoromethoxy,
$R^{12}$ is fluorine or trifluoromethyl,
$R^{13}$ is fluorine,
either
$R^2$ is ethyl, propyl or isopropyl, and
$R^3$ is hydrogen,
or
$R^2$ is methyl, and
$R^3$ is hydrogen,
or
$R^2$ is methyl, and
$R^3$ is methyl,
or
$R^2$ is hydrogen, and
$R^3$ is hydrogen,
or $R^2$ and $R^3$ together and with inclusion of the carbon atom, to which they are attached, form a cyclopentane ring,
either
$R^4$ is isopropyl or isobutyl, and
$R^5$ is hydrogen,
or
$R^4$ is methyl, and
$R^5$ is methyl,
or
$R^4$ is hydrogen, and
$R^5$ is hydrogen,
or $R^4$ and $R^5$ together and with inclusion of the carbon atom, to which they are attached, form a cyclopropane, cyclobutane, cyclopentane or cyclohexane ring,
either
$R^6$ is fluorine or methoxy, and
$R^7$ is hydrogen,
or
$R^6$ is hydroxyl, and
$R^7$ is methyl,
or
$R^6$ is hydroxyl, and
$R^7$ is hydrogen,
or $R^6$ and $R^7$ taken together and with the carbon atom, to which they are bonded, form a carbonyl ($>$C$=$O) or oxime ($>$C$=$N—OH) group,
$R^8$ is 1-4C-alkyl, cyclopropyl, cyclobutyl, cyclopentyl, cyclohexyl, or phenyl substituted by $R^{81}$ and/or $R^{82}$, in which
$R^{81}$ is fluorine, methyl, trifluoromethyl, methoxy or trifluoromethoxy,
$R^{82}$ is fluorine or trifluoromethyl,
the tautomers, the stereoisomers thereof, the mixtures thereof and the salts thereof.

A still yet closer embodiment of the compounds according to aspect B of this invention refers to those compounds of formula I, wherein
$R^1$ is phenyl substituted by $R^{11}$ and/or $R^{12}$ and/or $R^{13}$, or pyridyl substituted by $R^{11}$, in which
$R^{11}$ is fluorine, tert-butyl, trifluoromethyl or trifluoromethoxy,
$R^{12}$ is fluorine or trifluoromethyl,
$R^{13}$ is fluorine,
either
$R^2$ is ethyl, and
$R^3$ is hydrogen,
or
$R^2$ is isopropyl, and
$R^3$ is hydrogen,
or
$R^2$ is methyl, and
$R^3$ is hydrogen,
or
$R^2$ is methyl, and
$R^3$ is methyl,
either
$R^4$ is methyl, and
$R^5$ is methyl,
or $R^4$ and $R^5$ together and with inclusion of the carbon atom, to which they are attached, form a cyclopropane ring,
or $R^4$ and $R^5$ together and with inclusion of the carbon atom, to which they are attached, form a cyclobutane ring,
or $R^4$ and $R^5$ together and with inclusion of the carbon atom, to which they are attached, form a cyclopentane ring,
or $R^4$ and $R^5$ together and with inclusion of the carbon atom, to which they are attached, form a cyclohexane ring,
$R^6$ is hydroxyl,
$R^7$ is hydrogen,
$R^8$ is cyclopropyl, cyclobutyl, cyclopentyl or cyclohexyl,
the tautomers, the stereoisomers thereof, the mixtures thereof and the salts thereof.

Some further special meanings of individual groups, residues and substituents of the compounds according to this invention are given hereinafter:
A special meaning of $R^1$ is phenyl substituted by $R^{11}$ and/or $R^{12}$ and/or $R^{13}$, in which
$R^{11}$ is halogen, trifluoromethyl, 1-4C-alkyl, 1-4C-alkoxy, or completely or predominantly fluorine-substituted 1-4C-alkoxy,
$R^{12}$ is halogen, trifluoromethyl, 1-4C-alkyl, 1-4C-alkoxy, or completely or predominantly fluorine-substituted 1-4C-alkoxy,
$R^{13}$ is halogen;
more precisely,
$R^1$ is phenyl substituted in meta or para position by $R^{11}$ and/or $R^{12}$ and/or $R^{13}$, in which
$R^{11}$ is fluorine, tert-butyl, trifluoromethyl or trifluoromethoxy,
$R^{12}$ is fluorine or trifluoromethyl,
$R^{13}$ is fluorine;
certain special meanings of $R^1$ include hereby: (trifluoromethyl)phenyl (such as 4-trifluoromethyl-phenyl or 3-trifluoromethyl-phenyl), bis(trifluoromethyl)phenyl (such as 3,5-bis-(trifluoromethyl)-phenyl), (trifluoromethoxy)phenyl (such as 4-trifluoromethoxy-phenyl or 3-trifluoromethoxy-phenyl), fluorophenyl (such as 4-fluoro-phenyl or 3-fluoro-phenyl), difluorophenyl (such as 3,4-difluoro-phenyl or 3,5-difluoro-phenyl), and trifluorophenyl (such as 3,4,5-trifluoro-phenyl), and (tertbutyl)phenyl (such as 4-tertbutyl-phenyl or 3-tertbutyl-phenyl).

Another special meaning of $R^1$ is pyridyl substituted by $R^{11}$ and/or $R^{12}$, in which $R^{11}$ is halogen, trifluoromethyl, 1-4C-alkyl, 1-4C-alkoxy, or completely or predominantly fluorine-substituted 1-4C-alkoxy, $R^{12}$ is halogen, 1-4C-alkyl, or 1-4C-alkoxy;

more precisely, $R^1$ is pyridyl substituted by $R^{11}$, in which $R^{11}$ is fluorine, tert-butyl, trifluoromethyl or trifluoromethoxy;

certain special meanings of $R^1$ include hereby: (trifluoromethyl)pyridyl (such as 5-trifluoromethyl-pyridin-2-yl or 3-trifluoromethyl-pyridin-2-yl).

In a particular embodiment of this invention, $R^1$ is 4-trifluoromethyl-phenyl.

A special meaning of $R^2$ is hydrogen or 1-4C-alkyl (e.g. methyl, ethyl or isopropyl), particularly methyl.

A special meaning of $R^3$ is hydrogen, methyl or ethyl, particularly hydrogen.

Certain special meanings of $R^2$ and $R^3$ include hereby: $R^2$ is hydrogen and $R^3$ is hydrogen, $R^2$ is methyl and $R^3$ is methyl; $R^2$ is methyl and $R^3$ is hydrogen; $R^2$ is ethyl and $R^3$ is hydrogen; and $R^2$ is isopropyl and $R^3$ is hydrogen.

Other special meanings of $R^2$ and $R^3$ include: $R^2$ and $R^3$ together and with inclusion of the carbon, to which they are attached, form a cyclopentane or cyclohexane ring.

In a particular embodiment of this invention, $R^2$ is methyl and $R^3$ is methyl.

In a particular embodiment of this invention, $R^2$ is methyl and $R^3$ is hydrogen.

In a particular embodiment of this invention, $R^2$ and $R^3$ together and with inclusion of the carbon, to which they are attached, form a cyclopentane ring.

In a particular embodiment of this invention, $R^2$ and $R^3$ together and with inclusion of the carbon, to which they are attached, form a cyclohexane ring.

Special meanings of $R^4$ and $R^5$ include: $R^4$ is 1-4C-alkyl (e.g. methyl) and $R^5$ is methyl; $R^4$ is 1-4C-alkyl (e.g. isopropyl or isobutyl) and $R^5$ is hydrogen; and $R^4$ is hydrogen and $R^5$ is hydrogen.

Other special meanings of $R^4$ and $R^5$ include: $R^4$ and $R^5$ together and with inclusion of the carbon atom, to which they are attached, form a cyclopropane ring, a cyclobutane ring, a cyclopentane ring or a cyclohexane ring, particularly a cyclopropane ring, a cyclobutane ring or a cyclopentane ring.

In a particular embodiment of this invention, $R^4$ is methyl and $R^5$ is methyl.

A special meaning of $R^6$ is hydroxyl, 1-4C-alkoxy (e.g. methoxy) or fluorine, particularly hydroxyl.

A special meaning of $R^7$ is hydrogen, or 1-4C-alkyl (e.g. methyl), particularly hydrogen.

Special meanings of $R^6$ and $R^7$ include: $R^6$ is hydroxyl and $R^7$ is hydrogen; $R^6$ is hydroxyl and $R^7$ is methyl, $R^6$ is fluorine and $R^7$ is hydrogen; and $R^6$ is methoxy and $R^7$ is hydrogen.

Other special meanings of $R^6$ and $R^7$ include: $R^6$ and $R^7$ together and with inclusion of the carbon atom, to which they are attached, form a carbonyl group or an oxime group.

In a particular embodiment of this invention, $R^6$ is hydroxyl and $R^7$ is hydrogen.

A special meaning of $R^8$ is 1-4C-alkyl (e.g. propyl or isopropyl).

Another special meaning of $R^8$ is 3-6C-cycloalkyl.

Certain special meanings of $R^8$ include hereby: cyclopropyl, cyclobutyl, cyclopentyl and cyclohexyl.

Another special meaning of $R^8$ is phenyl substituted by $R^{81}$ and/or $R^{82}$, in which $R^{81}$ is halogen, trifluoromethyl, 1-4C-alkyl, 1-4C-alkoxy, or completely or predominantly fluorine-substituted 1-4C-alkoxy, $R^{82}$ is halogen, trifluoromethyl, 1-4C-alkyl, 1-4C-alkoxy, or completely or predominantly fluorine-substituted 1-4C-alkoxy;

more precisely, $R^8$ is phenyl substituted in meta or para position by $R^{81}$ and/or $R^{82}$, in which $R^{81}$ is fluorine, methyl, trifluoromethyl, methoxy or trifluoromethoxy, $R^{82}$ is fluorine or trifluoromethyl;

certain special meanings of $R^8$ include hereby: (trifluoromethyl)phenyl (such as 4-trifluoromethyl-phenyl or 3-trifluoromethyl-phenyl), bis(trifluoromethyl)phenyl (such as 3,5-bis-(trifluoromethyl)-phenyl), (trifluoromethoxy)phenyl (such as 4-trifluoromethoxy-phenyl or 3-trifluoromethoxy-phenyl), fluorophenyl (such as 4-fluoro-phenyl or 3-fluoro-phenyl), difluorophenyl (such as 3,4-difluoro-phenyl or 3,5-difluoro-phenyl), methylphenyl (such as 4-methyl-phenyl or 3-methyl-phenyl), and methoxyphenyl (such as 4-methoxy-phenyl or 3-methoxy-phenyl).

Another special meaning of $R^8$ is 3- to 7-membered heterocycloalkyl.

Certain special meanings of $R^8$ include hereby: tetrahydrofuranyl, tetrahydropyranyl, piperidinyl and pyrrolidinyl.

In a particular embodiment of this invention, $R^8$ is cyclopentyl.

In a particular embodiment of this invention, $R^8$ is cyclohexyl.

In a particular embodiment of this invention, $R^8$ is tetrahydropyran-4-yl.

In another particular embodiment of this invention, $R^1$, $R^2$, $R^4$, $R^5$ and $R^8$ have any of the meanings 1.1 to 1.260 indicated in the Table 1 given below.

In another particular embodiment of this invention, the compound of formula I according to this invention is from any one of the formulae Ie* and If* as shown herein.

In another particular embodiment of this invention, the compound of formula I according to this invention is from any one of the formulae Ia*, Ib*, Ic* and Id* as shown herein.

In a more particular embodiment of this invention, the compound of formula I according to this invention is from formula Ia* as shown herein.

In another more particular embodiment of this invention, the compound of formula I according to this invention is from formula Ie* as shown herein.

It is to be understood that the present invention further includes any possible combinations and subsets of the special meanings defined herein.

As illustrative compounds according to this invention the following compounds of formula Ia*

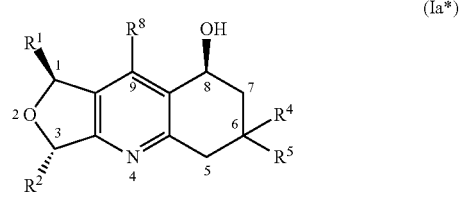

(Ia*)

and the salts thereof may be mentioned by means of the substituent meanings for $R^1$, $R^2$, $R^4$, $R^5$ and $R^8$ in the Table 1 given below.

As other illustrative compounds according to this invention the following compounds of formula Ib*

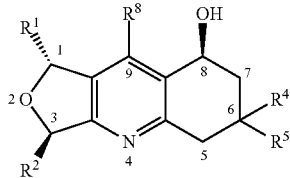

(Ib*)

and the salts thereof may be mentioned by means of the substituent meanings for $R^1$, $R^2$, $R^4$, $R^5$ and $R^8$ in the Table 1 given below.

As other illustrative compounds according to this invention the following compounds of formula Ic*

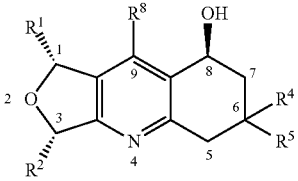

(Ic*)

and the salts thereof may be mentioned by means of the substituent meanings for $R^1$, $R^2$, $R^4$, $R^5$ and $R^8$ in the Table 1 given below.

As other illustrative compounds according to this invention the following compounds of formula Id*

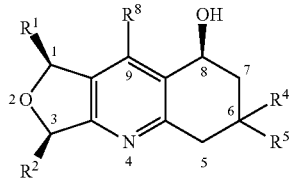

(Id*)

and the salts thereof may be mentioned by means of the substituent meanings for $R^1$, $R^2$, $R^4$, $R^5$ and $R^8$ in the Table 1 given below.

As other illustrative compounds according to this invention the following compounds of formula Ie*

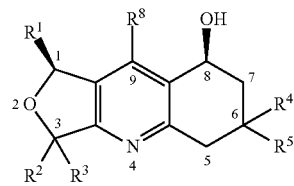

(Ie*)

in which $R^2$ is methyl and $R^3$ is methyl, and the salts thereof, may be mentioned by means of the substituent meanings for $R^1$, $R^4$, $R^5$ and $R^8$ in the Table 1 given below.

As other illustrative compounds according to this invention the following compounds of formula If*

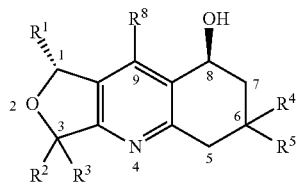

(If*)

in which $R^2$ is methyl and $R^3$ is methyl, and the salts thereof, may be mentioned by means of the substituent meanings for $R^1$, $R^4$, $R^5$ and $R^8$ in the Table 1 given below.

As other illustrative compounds according to this invention the following compounds of formula Ie* in which $R^2$ and $R^3$ together and with inclusion of the carbon, to which they are attached, form a cyclopentane ring, and the salts thereof, may be mentioned by means of the substituent meanings for $R^1$, $R^4$, $R^5$ and $R^8$ in the Table 1 given below.

As other illustrative compounds according to this invention the following compounds of formula If* in which $R^2$ and $R^3$ together and with inclusion of the carbon, to which they are attached, form a cyclopentane ring, and the salts thereof, may be mentioned by means of the substituent meanings for $R^1$, $R^4$, $R^5$ and $R^8$ in the Table 1 given below.

As other illustrative compounds according to this invention the following compounds of formula Ie* in which $R^2$ and $R^3$ together and with inclusion of the carbon, to which they are attached, form a cyclohexane ring, and the salts thereof, may be mentioned by means of the substituent meanings for $R^1$, $R^4$, $R^5$ and $R^8$ in the Table 1 given below.

As other illustrative compounds according to this invention the following compounds of formula If* in which $R^2$ and $R^3$ together and with inclusion of the carbon, to which they are attached, form a cyclohexane ring, and the salts thereof, may be mentioned by means of the substituent meanings for $R^1$, $R^4$, $R^5$ and $R^8$ in the Table 1 given below.

TABLE 1

| No. | $R^1$ | $R^2$ | $R^4$ / $R^5$ | $R^8$ |
|---|---|---|---|---|
| 1.1 | F$_3$C—⟨phenyl⟩— | —CH$_3$ | —C(CH$_3$)$_2$ | cyclopentyl |

TABLE 1-continued

| No. | R¹ | R² | ![R⁴R⁵ group] | R⁸ |
|---|---|---|---|---|
| 1.2 | 4-CF₃-C₆H₄- | —CH₃ | cyclopropyl (spiro) | cyclopentyl |
| 1.3 | 4-CF₃-C₆H₄- | —CH₃ | cyclobutyl (spiro) | cyclopentyl |
| 1.4 | 4-CF₃-C₆H₄- | —CH₃ | cyclopentyl (spiro) | cyclopentyl |
| 1.5 | 3-CF₃-C₆H₄- | —CH₃ | C(CH₃)₂ | cyclopentyl |
| 1.6 | 3-CF₃-C₆H₄- | —CH₃ | cyclopropyl (spiro) | cyclopentyl |
| 1.7 | 3-CF₃-C₆H₄- | —CH₃ | cyclobutyl (spiro) | cyclopentyl |
| 1.8 | 3-CF₃-C₆H₄- | —CH₃ | cyclopentyl (spiro) | cyclopentyl |
| 1.9 | 3,5-(CF₃)₂-C₆H₃- | —CH₃ | C(CH₃)₂ | cyclopentyl |

TABLE 1-continued
| No. | R¹ | R² | 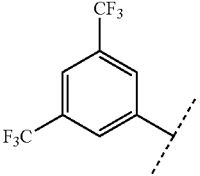 | R⁸ |
|---|---|---|---|---|
| 1.10 | 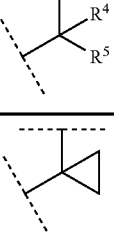 | —CH₃ | 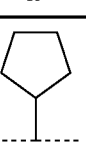 | 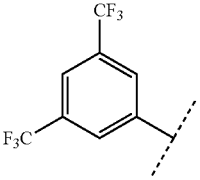 |
| 1.11 | 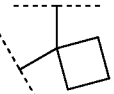 | —CH₃ |  | 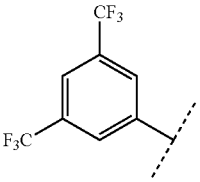 |
| 1.12 |  | —CH₃ |  | 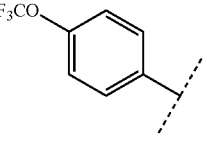 |
| 1.13 | 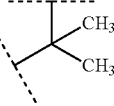 | —CH₃ |  | 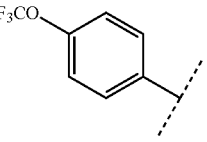 |
| 1.14 | 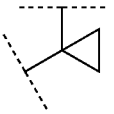 | —CH₃ | 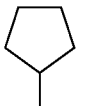 | 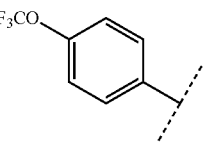 |
| 1.15 |  | —CH₃ |  | 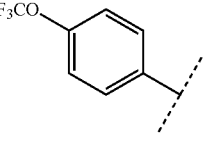 |
| 1.16 |  | —CH₃ |  | 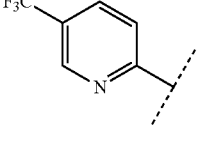 |
| 1.17 | 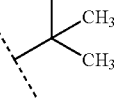 | —CH₃ |  | 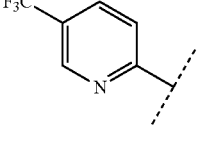 |
| 1.18 | 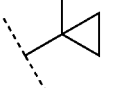 | —CH₃ |  | |

TABLE 1-continued

| No. | R¹ | R² | ⸺C(R⁴)(R⁵)⸺ | R⁸ |
|---|---|---|---|---|
| 1.19 | 5-CF₃-pyridin-2-yl | —CH₃ | cyclobutyl (spiro, methyl) | cyclopentyl |
| 1.20 | 5-CF₃-pyridin-2-yl | —CH₃ | cyclopentyl (spiro, methyl) | cyclopentyl |
| 1.21 | 4-CF₃-phenyl | —CH₃ | —C(CH₃)₂— | cyclohexyl |
| 1.22 | 4-CF₃-phenyl | —CH₃ | cyclopropyl (spiro) | cyclohexyl |
| 1.23 | 4-CF₃-phenyl | —CH₃ | cyclobutyl (spiro) | cyclohexyl |
| 1.24 | 4-CF₃-phenyl | —CH₃ | cyclopentyl (spiro) | cyclohexyl |
| 1.25 | 3-CF₃-phenyl | —CH₃ | —C(CH₃)₂— | cyclohexyl |
| 1.26 | 3-CF₃-phenyl | —CH₃ | cyclopropyl (spiro) | cyclohexyl |
| 1.27 | 3-CF₃-phenyl | —CH₃ | cyclobutyl (spiro) | cyclohexyl |

TABLE 1-continued
| No. | R¹ | R² | $\overset{R^4}{\underset{R^5}{\diagup}}$ | R⁸ |
|---|---|---|---|---|
| 1.28 | 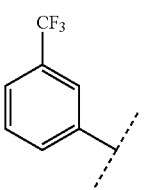 | —CH₃ | 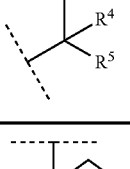 | 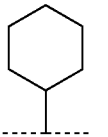 |
| 1.29 | 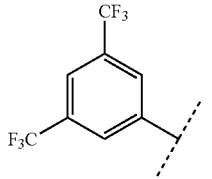 | —CH₃ | 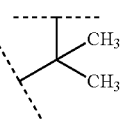 | 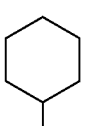 |
| 1.30 | 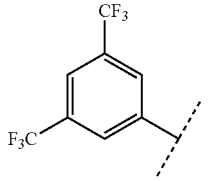 | —CH₃ |  | 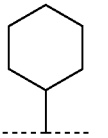 |
| 1.31 | 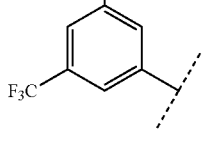 | —CH₃ | 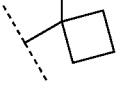 | 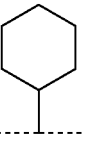 |
| 1.32 | 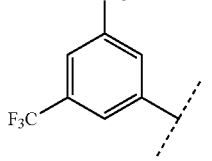 | —CH₃ | 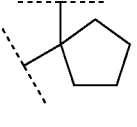 | 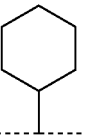 |
| 1.33 | 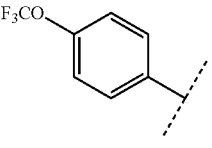 | —CH₃ | 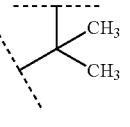 | 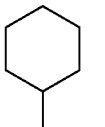 |
| 1.34 | 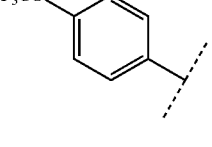 | —CH₃ | 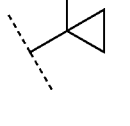 | 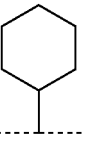 |
| 1.35 | 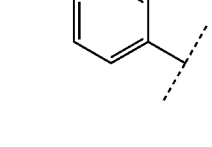 | —CH₃ | 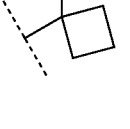 | 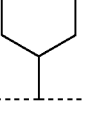 |

TABLE 1-continued

| No. | R¹ | R² | ─C(R⁴)(R⁵)─ | R⁸ |
|---|---|---|---|---|
| 1.36 | 4-F₃CO-C₆H₄-CH₂- | ─CH₃ | 1-cyclopentyl (spiro) | cyclohexyl |
| 1.37 | 5-F₃C-pyridin-2-yl-CH₂- | ─CH₃ | ─C(CH₃)₂─ | cyclohexyl |
| 1.38 | 5-F₃C-pyridin-2-yl-CH₂- | ─CH₃ | 1-cyclopropyl (spiro) | cyclohexyl |
| 1.39 | 5-F₃C-pyridin-2-yl-CH₂- | ─CH₃ | 1-cyclobutyl (spiro) | cyclohexyl |
| 1.40 | 5-F₃C-pyridin-2-yl-CH₂- | ─CH₃ | 1-cyclopentyl (spiro) | cyclohexyl |
| 1.41 | 4-F₃C-C₆H₄-CH₂- | ─CH₃ | ─C(CH₃)₂─ | cyclobutyl |
| 1.42 | 4-F₃C-C₆H₄-CH₂- | ─CH₃ | 1-cyclopropyl (spiro) | cyclobutyl |
| 1.43 | 4-F₃C-C₆H₄-CH₂- | ─CH₃ | 1-cyclobutyl (spiro) | cyclobutyl |
| 1.44 | 4-F₃C-C₆H₄-CH₂- | ─CH₃ | 1-cyclopentyl (spiro) | cyclobutyl |

TABLE 1-continued

| No. | R¹ | R² | ![R4/R5 group] | R⁸ |
|---|---|---|---|---|
| 1.45 | 3-CF₃-phenyl | —CH₃ | C(CH₃)₂ | cyclobutyl |
| 1.46 | 3-CF₃-phenyl | —CH₃ | spiro-cyclopropyl | cyclobutyl |
| 1.47 | 3-CF₃-phenyl | —CH₃ | spiro-cyclobutyl | cyclobutyl |
| 1.48 | 3-CF₃-phenyl | —CH₃ | spiro-cyclopentyl | cyclobutyl |
| 1.49 | 3,5-bis(CF₃)-phenyl | —CH₃ | C(CH₃)₂ | cyclobutyl |
| 1.50 | 3,5-bis(CF₃)-phenyl | —CH₃ | spiro-cyclopropyl | cyclobutyl |
| 1.51 | 3,5-bis(CF₃)-phenyl | —CH₃ | spiro-cyclobutyl | cyclobutyl |

TABLE 1-continued
| No. | R¹ | R² | 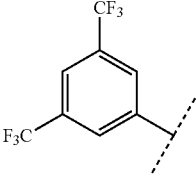 | R⁸ |
|---|---|---|---|---|
| 1.52 | 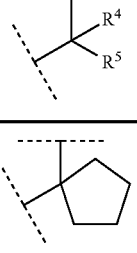 | —CH₃ | 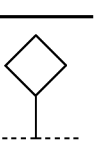 | 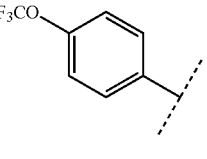 |
| 1.53 | 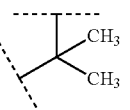 | —CH₃ | 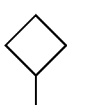 | 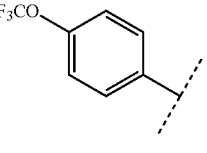 |
| 1.54 | 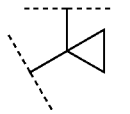 | —CH₃ | 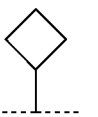 | 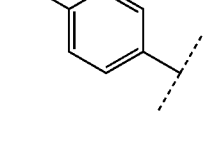 |
| 1.55 | 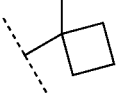 | —CH₃ | 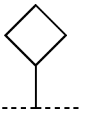 | 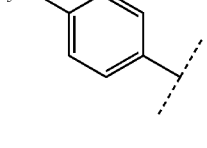 |
| 1.56 | 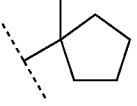 | —CH₃ | 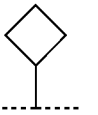 | 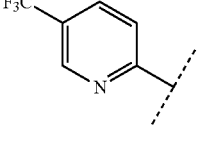 |
| 1.57 | 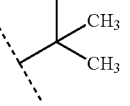 | —CH₃ | 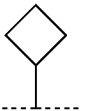 | 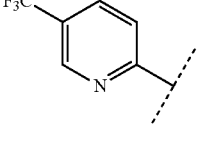 |
| 1.58 | 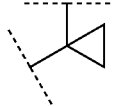 | —CH₃ | 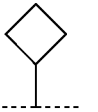 | 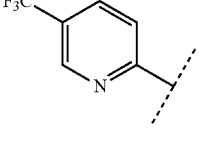 |
| 1.59 | 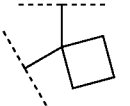 | —CH₃ | 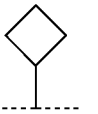 | 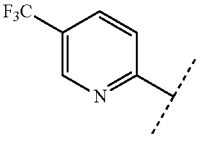 |
| 1.60 | 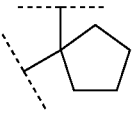 | —CH₃ | 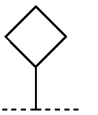 | |

TABLE 1-continued

| No. | R¹ | R² | ![R⁴ R⁵ structure] | R⁸ |
|---|---|---|---|---|
| 1.61 | 4-CF₃-C₆H₄– | –CH₃ | –C(CH₃)₂– (gem-dimethyl) | cyclopropyl |
| 1.62 | 4-CF₃-C₆H₄– | –CH₃ | spiro-cyclopropyl | cyclopropyl |
| 1.63 | 4-CF₃-C₆H₄– | –CH₃ | spiro-cyclobutyl | cyclopropyl |
| 1.64 | 4-CF₃-C₆H₄– | –CH₃ | spiro-cyclopentyl | cyclopropyl |
| 1.65 | 3-CF₃-C₆H₄– | –CH₃ | –C(CH₃)₂– (gem-dimethyl) | cyclopropyl |
| 1.66 | 3-CF₃-C₆H₄– | –CH₃ | spiro-cyclopropyl | cyclopropyl |
| 1.67 | 3-CF₃-C₆H₄– | –CH₃ | spiro-cyclobutyl | cyclopropyl |
| 1.68 | 3-CF₃-C₆H₄– | –CH₃ | spiro-cyclopentyl | cyclopropyl |

TABLE 1-continued

| No. | R¹ | R² | ![R⁴/R⁵ group] | R⁸ |
|---|---|---|---|---|
| 1.69 | 3,5-bis(CF₃)phenyl | —CH₃ | C(CH₃)₂ | cyclopropyl |
| 1.70 | 3,5-bis(CF₃)phenyl | —CH₃ | spiro-cyclopropyl | cyclopropyl |
| 1.71 | 3,5-bis(CF₃)phenyl | —CH₃ | spiro-cyclobutyl | cyclopropyl |
| 1.72 | 3,5-bis(CF₃)phenyl | —CH₃ | spiro-cyclopentyl | cyclopropyl |
| 1.73 | 4-F₃CO-phenyl | —CH₃ | C(CH₃)₂ | cyclopropyl |
| 1.74 | 4-F₃CO-phenyl | —CH₃ | spiro-cyclopropyl | cyclopropyl |
| 1.75 | 4-F₃CO-phenyl | —CH₃ | spiro-cyclobutyl | cyclopropyl |
| 1.76 | 4-F₃CO-phenyl | —CH₃ | spiro-cyclopentyl | cyclopropyl |
| 1.77 | 5-CF₃-pyridin-2-yl | —CH₃ | C(CH₃)₂ | cyclopropyl |

TABLE 1-continued
| No. | R¹ | R² | 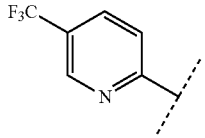 | R⁸ |
|---|---|---|---|---|
| 1.78 | 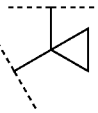 | —CH₃ | 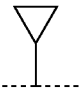 | 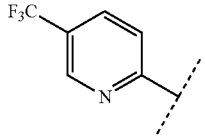 |
| 1.79 | 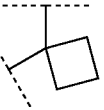 | —CH₃ | 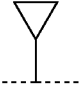 | 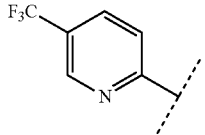 |
| 1.80 | 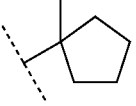 | —CH₃ | 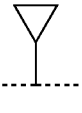 | 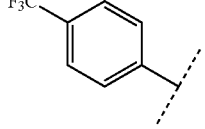 |
| 1.81 | 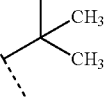 | —CH₂CH₃ | 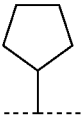 | 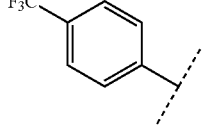 |
| 1.82 | 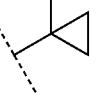 | —CH₂CH₃ | 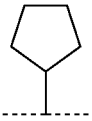 | 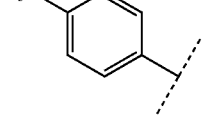 |
| 1.83 | 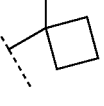 | —CH₂CH₃ | 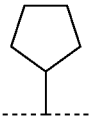 | 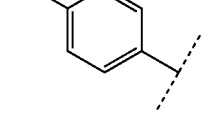 |
| 1.84 | 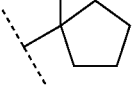 | —CH₂CH₃ | 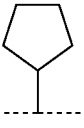 | 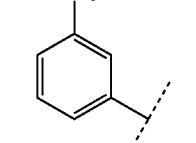 |
| 1.85 | 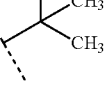 | —CH₂CH₃ | 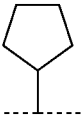 | 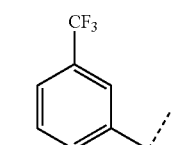 |
| 1.86 | 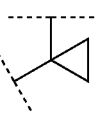 | —CH₂CH₃ | 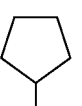 | |

TABLE 1-continued

| No. | R¹ | R² | ![R⁴/R⁵ group] | R⁸ |
|---|---|---|---|---|
| 1.87 | 3-CF₃-phenyl | —CH₂CH₃ | cyclobutyl-spiro | cyclopentyl |
| 1.88 | 3-CF₃-phenyl | —CH₂CH₃ | cyclopentyl-spiro | cyclopentyl |
| 1.89 | 3,5-(CF₃)₂-phenyl | —CH₂CH₃ | C(CH₃)₂ | cyclopentyl |
| 1.90 | 3,5-(CF₃)₂-phenyl | —CH₂CH₃ | cyclopropyl-spiro | cyclopentyl |
| 1.91 | 3,5-(CF₃)₂-phenyl | —CH₂CH₃ | cyclobutyl-spiro | cyclopentyl |
| 1.92 | 3,5-(CF₃)₂-phenyl | —CH₂CH₃ | cyclopentyl-spiro | cyclopentyl |
| 1.93 | 4-F₃CO-phenyl | —CH₂CH₃ | C(CH₃)₂ | cyclopentyl |
| 1.94 | 4-F₃CO-phenyl | —CH₂CH₃ | cyclopropyl-spiro | cyclopentyl |

TABLE 1-continued

| No. | R¹ | R² | ![R⁴/R⁵ group] | R⁸ |
|---|---|---|---|---|
| 1.95 | F₃CO-C₆H₄- | —CH₂CH₃ | spiro-cyclobutyl | cyclopentyl |
| 1.96 | F₃CO-C₆H₄- | —CH₂CH₃ | spiro-cyclopentyl | cyclopentyl |
| 1.97 | 5-F₃C-pyridin-2-yl | —CH₂CH₃ | C(CH₃)₂ | cyclopentyl |
| 1.98 | 5-F₃C-pyridin-2-yl | —CH₂CH₃ | spiro-cyclopropyl | cyclopentyl |
| 1.99 | 5-F₃C-pyridin-2-yl | —CH₂CH₃ | spiro-cyclobutyl | cyclopentyl |
| 1.100 | 5-F₃C-pyridin-2-yl | —CH₂CH₃ | spiro-cyclopentyl | cyclopentyl |
| 1.101 | F₃C-C₆H₄- | —CH₂CH₃ | C(CH₃)₂ | cyclohexyl |
| 1.102 | F₃C-C₆H₄- | —CH₂CH₃ | spiro-cyclopropyl | cyclohexyl |
| 1.103 | F₃C-C₆H₄- | —CH₂CH₃ | spiro-cyclobutyl | cyclohexyl |
| 1.104 | F₃C-C₆H₄- | —CH₂CH₃ | spiro-cyclopentyl | cyclohexyl |

TABLE 1-continued
| No. | R¹ | R² | 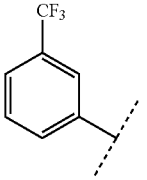 | R⁸ |
|---|---|---|---|---|
| 1.105 | 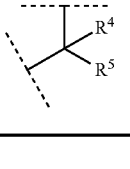 | —CH$_2$CH$_3$ | 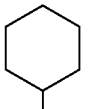 | 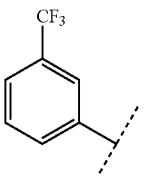 |
| 1.106 | 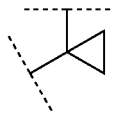 | —CH$_2$CH$_3$ | 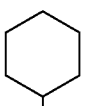 | 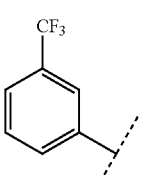 |
| 1.107 | 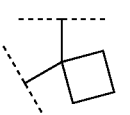 | —CH$_2$CH$_3$ | 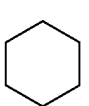 | 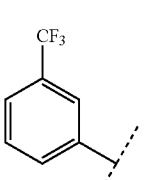 |
| 1.108 |  | —CH$_2$CH$_3$ | 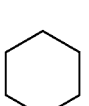 | 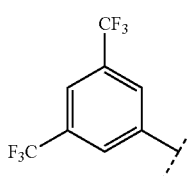 |
| 1.109 | 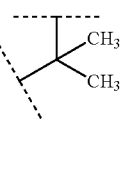 | —CH$_2$CH$_3$ | 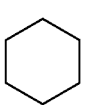 | 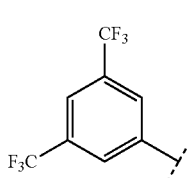 |
| 1.110 | 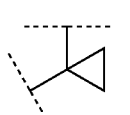 | —CH$_2$CH$_3$ | 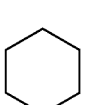 | 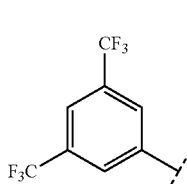 |
| 1.111 | 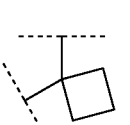 | —CH$_2$CH$_3$ | 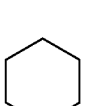 | |

TABLE 1-continued

| No. | R¹ | R² | ![CR⁴R⁵] | R⁸ |
|---|---|---|---|---|
| 1.112 | 3,5-bis(CF₃)phenyl-CH₂- 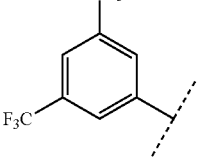 | —CH₂CH₃ | cyclopentyl 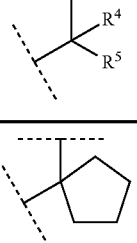 | cyclohexyl 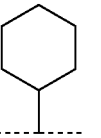 |
| 1.113 | 4-F₃CO-phenyl-CH₂- 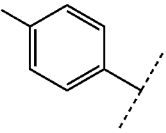 | —CH₂CH₃ | —C(CH₃)₂— 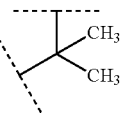 | cyclohexyl 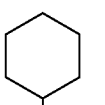 |
| 1.114 | 4-F₃CO-phenyl-CH₂- 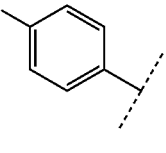 | —CH₂CH₃ | cyclopropyl 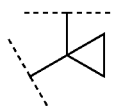 | cyclohexyl 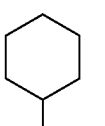 |
| 1.115 | 4-F₃CO-phenyl-CH₂- 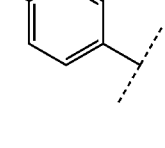 | —CH₂CH₃ | cyclobutyl 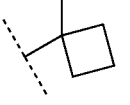 | cyclohexyl 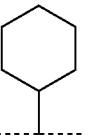 |
| 1.116 | 4-F₃CO-phenyl-CH₂- 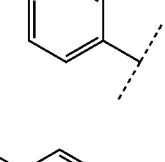 | —CH₂CH₃ | cyclopentyl 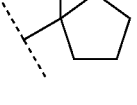 | cyclohexyl 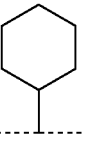 |
| 1.117 | 5-F₃C-pyridin-2-yl-CH₂- 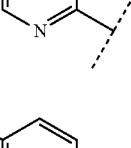 | —CH₂CH₃ | —C(CH₃)₂— 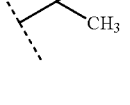 | cyclohexyl 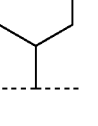 |
| 1.118 | 5-F₃C-pyridin-2-yl-CH₂- 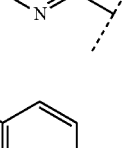 | —CH₂CH₃ | cyclopropyl  | cyclohexyl 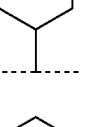 |
| 1.119 | 5-F₃C-pyridin-2-yl-CH₂- 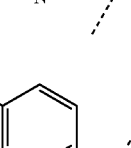 | —CH₂CH₃ | cyclobutyl 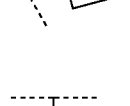 | cyclohexyl 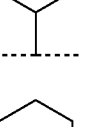 |
| 1.120 | 5-F₃C-pyridin-2-yl-CH₂- 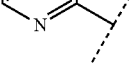 | —CH₂CH₃ | cyclopentyl 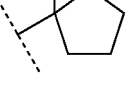 | cyclohexyl 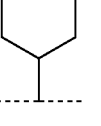 |

TABLE 1-continued

| No. | R¹ | R² | ![R⁴R⁵ group] | R⁸ |
|---|---|---|---|---|
| 1.121 | 4-(F₃C)-C₆H₄- | —CH₂CH₃ | —C(CH₃)₂— | cyclobutyl |
| 1.122 | 4-(F₃C)-C₆H₄- | —CH₂CH₃ | 1,1-cyclopropylidene | cyclobutyl |
| 1.123 | 4-(F₃C)-C₆H₄- | —CH₂CH₃ | 1,1-cyclobutylidene | cyclobutyl |
| 1.124 | 4-(F₃C)-C₆H₄- | —CH₂CH₃ | 1,1-cyclopentylidene | cyclobutyl |
| 1.125 | 3-(CF₃)-C₆H₄- | —CH₂CH₃ | —C(CH₃)₂— | cyclobutyl |
| 1.126 | 3-(CF₃)-C₆H₄- | —CH₂CH₃ | 1,1-cyclopropylidene | cyclobutyl |
| 1.127 | 3-(CF₃)-C₆H₄- | —CH₂CH₃ | 1,1-cyclobutylidene | cyclobutyl |
| 1.128 | 3-(CF₃)-C₆H₄- | —CH₂CH₃ | 1,1-cyclopentylidene | cyclobutyl |

TABLE 1-continued

| No. | R¹ | R² | ⋯⋯C(R⁴)(R⁵)⋯ | R⁸ |
|---|---|---|---|---|
| 1.129 | 3,5-bis(CF₃)phenyl | —CH₂CH₃ | —C(CH₃)₂— | cyclobutyl |
| 1.130 | 3,5-bis(CF₃)phenyl | —CH₂CH₃ | 1,1-cyclopropyl (spiro) | cyclobutyl |
| 1.131 | 3,5-bis(CF₃)phenyl | —CH₂CH₃ | 1,1-cyclobutyl (spiro) | cyclobutyl |
| 1.132 | 3,5-bis(CF₃)phenyl | —CH₂CH₃ | 1,1-cyclopentyl (spiro) | cyclobutyl |
| 1.133 | 4-(F₃CO)phenyl | —CH₂CH₃ | —C(CH₃)₂— | cyclobutyl |
| 1.134 | 4-(F₃CO)phenyl | —CH₂CH₃ | 1,1-cyclopropyl (spiro) | cyclobutyl |
| 1.135 | 4-(F₃CO)phenyl | —CH₂CH₃ | 1,1-cyclobutyl (spiro) | cyclobutyl |
| 1.136 | 4-(F₃CO)phenyl | —CH₂CH₃ | 1,1-cyclopentyl (spiro) | cyclobutyl |
| 1.137 | 5-(CF₃)pyridin-2-yl | —CH₂CH₃ | —C(CH₃)₂— | cyclobutyl |

TABLE 1-continued

| No. | R¹ | R² | $\overset{R^4}{\underset{R^5}{\diagup}}$ | R⁸ |
|---|---|---|---|---|
| 1.138 | 5-CF₃-pyridin-2-yl | —CH₂CH₃ | spiro-cyclopropyl | cyclobutyl |
| 1.139 | 5-CF₃-pyridin-2-yl | —CH₂CH₃ | spiro-cyclobutyl | cyclobutyl |
| 1.140 | 5-CF₃-pyridin-2-yl | —CH₂CH₃ | spiro-cyclopentyl | cyclobutyl |
| 1.141 | 4-CF₃-phenyl | —CH₂CH₃ | C(CH₃)₂ | cyclopropyl |
| 1.142 | 4-CF₃-phenyl | —CH₂CH₃ | spiro-cyclopropyl | cyclopropyl |
| 1.143 | 4-CF₃-phenyl | —CH₂CH₃ | spiro-cyclobutyl | cyclopropyl |
| 1.144 | 4-CF₃-phenyl | —CH₂CH₃ | spiro-cyclopentyl | cyclopropyl |
| 1.145 | 3-CF₃-phenyl | —CH₂CH₃ | C(CH₃)₂ | cyclopropyl |
| 1.146 | 3-CF₃-phenyl | —CH₂CH₃ | spiro-cyclopropyl | cyclopropyl |

TABLE 1-continued

| No. | R¹ | R² | $\begin{array}{c}R^4\\R^5\end{array}$ | R⁸ |
|---|---|---|---|---|
| 1.147 | 3-CF₃-C₆H₄- | —CH₂CH₃ | spiro-cyclobutyl | cyclopropyl |
| 1.148 | 3-CF₃-C₆H₄- | —CH₂CH₃ | spiro-cyclopentyl | cyclopropyl |
| 1.149 | 3,5-(CF₃)₂-C₆H₃- | —CH₂CH₃ | C(CH₃)₂ | cyclopropyl |
| 1.150 | 3,5-(CF₃)₂-C₆H₃- | —CH₂CH₃ | spiro-cyclopropyl | cyclopropyl |
| 1.151 | 3,5-(CF₃)₂-C₆H₃- | —CH₂CH₃ | spiro-cyclobutyl | cyclopropyl |
| 1.152 | 3,5-(CF₃)₂-C₆H₃- | —CH₂CH₃ | spiro-cyclopentyl | cyclopropyl |
| 1.153 | 4-F₃CO-C₆H₄- | —CH₂CH₃ | C(CH₃)₂ | cyclopropyl |
| 1.154 | 4-F₃CO-C₆H₄- | —CH₂CH₃ | spiro-cyclopropyl | cyclopropyl |

TABLE 1-continued

| No. | R¹ | R² | ![](R⁴/R⁵) | R⁸ |
|---|---|---|---|---|
| 1.155 | F₃CO-C₆H₄- | —CH₂CH₃ | spiro[2.3] (cyclopropane-cyclobutane) | cyclopropyl |
| 1.156 | F₃CO-C₆H₄- | —CH₂CH₃ | spiro[2.4] (cyclopropane-cyclopentane) | cyclopropyl |
| 1.157 | F₃C-(2-pyridyl, 5-CF₃) | —CH₂CH₃ | —C(CH₃)₂— | cyclopropyl |
| 1.158 | F₃C-(2-pyridyl, 5-CF₃) | —CH₂CH₃ | spirocyclopropane | cyclopropyl |
| 1.159 | F₃C-(2-pyridyl, 5-CF₃) | —CH₂CH₃ | spiro[2.3] | cyclopropyl |
| 1.160 | F₃C-(2-pyridyl, 5-CF₃) | —CH₂CH₃ | spiro[2.4] | cyclopropyl |
| 1.161 | F₃C-C₆H₄- | —CH(CH₃)₂ (H₃C-CH-CH₃) | —C(CH₃)₂— | cyclopentyl |
| 1.162 | F₃C-C₆H₄- | —CH(CH₃)₂ | spirocyclopropane | cyclopentyl |
| 1.163 | F₃C-C₆H₄- | —CH(CH₃)₂ | spiro[2.3] | cyclopentyl |
| 1.164 | F₃C-C₆H₄- | —CH(CH₃)₂ | spiro[2.4] | cyclopentyl |

TABLE 1-continued
| No. | R¹ | R² | $\begin{array}{c}\text{---}R^4\\ \phantom{---}R^5\end{array}$ | R⁸ |
|---|---|---|---|---|
| 1.165 | 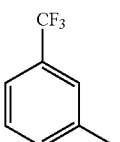 | 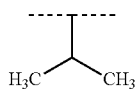 |  |  |
| 1.166 | 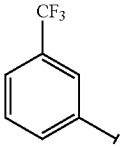 | 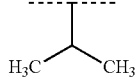 |  |  |
| 1.167 | 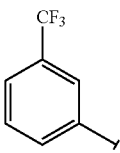 | 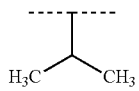 |  |  |
| 1.168 | 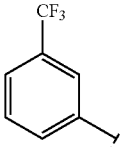 | 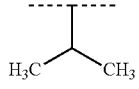 |  |  |
| 1.169 | 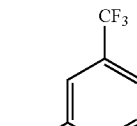 | 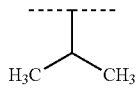 |  |  |
| 1.170 | 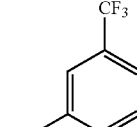 | 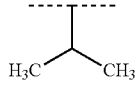 |  |  |
| 1.171 | 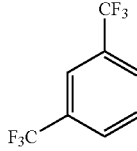 | 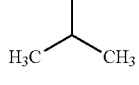 |  |  |

TABLE 1-continued

| No. | R¹ | R² | ![R⁴/R⁵ group] | R⁸ |
|---|---|---|---|---|
| 1.172 | 3,5-bis(CF₃)-phenyl- | -CH(CH₃)₂ | spiro[4.4] (cyclopentane-spiro) | cyclopentyl |
| 1.173 | 4-F₃CO-phenyl- | -CH(CH₃)₂ | -C(CH₃)₂- | cyclopentyl |
| 1.174 | 4-F₃CO-phenyl- | -CH(CH₃)₂ | spirocyclopropyl | cyclopentyl |
| 1.175 | 4-F₃CO-phenyl- | -CH(CH₃)₂ | spirocyclobutyl | cyclopentyl |
| 1.176 | 4-F₃CO-phenyl- | -CH(CH₃)₂ | spirocyclopentyl | cyclopentyl |
| 1.177 | 5-CF₃-pyridin-2-yl- | -CH(CH₃)₂ | -C(CH₃)₂- | cyclopentyl |
| 1.178 | 5-CF₃-pyridin-2-yl- | -CH(CH₃)₂ | spirocyclopropyl | cyclopentyl |
| 1.179 | 5-CF₃-pyridin-2-yl- | -CH(CH₃)₂ | spirocyclobutyl | cyclopentyl |
| 1.180 | 5-CF₃-pyridin-2-yl- | -CH(CH₃)₂ | spirocyclopentyl | cyclopentyl |

TABLE 1-continued
| No. | R¹ | R² | $\overset{R^4}{\underset{R^5}{\diagup}}$ | R⁸ |
|---|---|---|---|---|
| 1.181 | 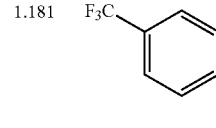 | 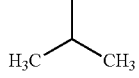 | 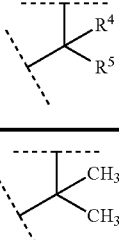 | 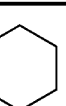 |
| 1.182 | 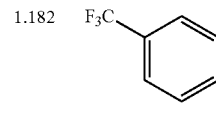 | 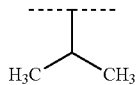 | 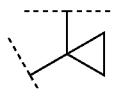 |  |
| 1.183 | 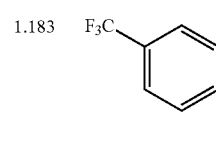 | 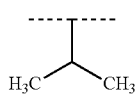 |  |  |
| 1.184 | 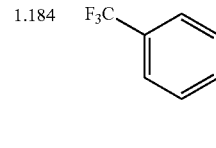 | 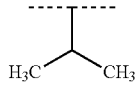 |  |  |
| 1.185 | 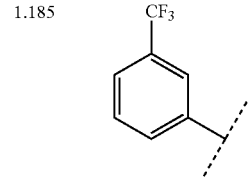 | 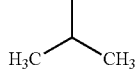 | 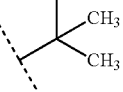 |  |
| 1.186 | 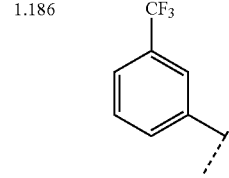 | 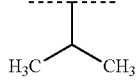 | 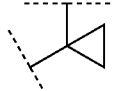 |  |
| 1.187 | 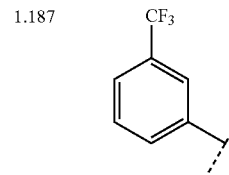 | 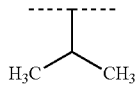 | 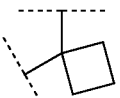 |  |
| 1.188 | 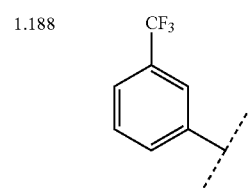 | 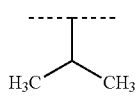 |  |  |

TABLE 1-continued

| No. | R¹ | R² | ![R⁴/R⁵ group] | R⁸ |
|---|---|---|---|---|
| 1.189 | 3,5-bis(CF₃)-phenyl-CH< | H₃C-CH(CH₃)- | -C(CH₃)₂- | cyclohexyl |
| 1.190 | 3,5-bis(CF₃)-phenyl-CH< | H₃C-CH(CH₃)- | spiro-cyclopropyl | cyclohexyl |
| 1.191 | 3,5-bis(CF₃)-phenyl-CH< | H₃C-CH(CH₃)- | spiro-cyclobutyl | cyclohexyl |
| 1.192 | 3,5-bis(CF₃)-phenyl-CH< | H₃C-CH(CH₃)- | spiro-cyclopentyl | cyclohexyl |
| 1.193 | 4-(F₃CO)-phenyl-CH< | H₃C-CH(CH₃)- | -C(CH₃)₂- | cyclohexyl |
| 1.194 | 4-(F₃CO)-phenyl-CH< | H₃C-CH(CH₃)- | spiro-cyclopropyl | cyclohexyl |
| 1.195 | 4-(F₃CO)-phenyl-CH< | H₃C-CH(CH₃)- | spiro-cyclobutyl | cyclohexyl |
| 1.196 | 4-(F₃CO)-phenyl-CH< | H₃C-CH(CH₃)- | spiro-cyclopentyl | cyclohexyl |
| 1.197 | 5-(F₃C)-pyridin-2-yl-CH< | H₃C-CH(CH₃)- | -C(CH₃)₂- | cyclohexyl |

TABLE 1-continued

| No. | R¹ | R² | ![R⁴/R⁵ group] | R⁸ |
|---|---|---|---|---|
| 1.198 | 5-CF₃-pyridin-2-yl | CH(CH₃)₂ | cyclopropyl (spiro) | cyclohexyl |
| 1.199 | 5-CF₃-pyridin-2-yl | CH(CH₃)₂ | cyclobutyl (spiro) | cyclohexyl |
| 1.200 | 5-CF₃-pyridin-2-yl | CH(CH₃)₂ | cyclopentyl (spiro) | cyclohexyl |
| 1.201 | 4-CF₃-phenyl | CH(CH₃)₂ | C(CH₃)₂ | cyclobutyl |
| 1.202 | 4-CF₃-phenyl | CH(CH₃)₂ | cyclopropyl (spiro) | cyclobutyl |
| 1.203 | 4-CF₃-phenyl | CH(CH₃)₂ | cyclobutyl (spiro) | cyclobutyl |
| 1.204 | 4-CF₃-phenyl | CH(CH₃)₂ | cyclopentyl (spiro) | cyclobutyl |
| 1.205 | 3-CF₃-phenyl | CH(CH₃)₂ | C(CH₃)₂ | cyclobutyl |
| 1.206 | 3-CF₃-phenyl | CH(CH₃)₂ | cyclopropyl (spiro) | cyclobutyl |

TABLE 1-continued

| No. | R¹ | R² | ![R⁴/R⁵ group] | R⁸ |
|---|---|---|---|---|
| 1.207 | 3-CF₃-phenyl | CH(CH₃)₂ | spiro[3.3] cyclobutane | cyclobutyl |
| 1.208 | 3-CF₃-phenyl | CH(CH₃)₂ | spiro[3.4] (cyclobutane/cyclopentane) | cyclobutyl |
| 1.209 | 3,5-bis(CF₃)-phenyl | CH(CH₃)₂ | C(CH₃)₂ | cyclobutyl |
| 1.210 | 3,5-bis(CF₃)-phenyl | CH(CH₃)₂ | spiro cyclopropane | cyclobutyl |
| 1.211 | 3,5-bis(CF₃)-phenyl | CH(CH₃)₂ | spiro[3.3] cyclobutane | cyclobutyl |
| 1.212 | 3,5-bis(CF₃)-phenyl | CH(CH₃)₂ | spiro[3.4] (cyclobutane/cyclopentane) | cyclobutyl |
| 1.213 | 4-OCF₃-phenyl | CH(CH₃)₂ | C(CH₃)₂ | cyclobutyl |
| 1.214 | 4-OCF₃-phenyl | CH(CH₃)₂ | spiro cyclopropane | cyclobutyl |

TABLE 1-continued
| No. | R¹ | R² |  | R⁸ |
|---|---|---|---|---|
| 1.215 | 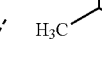 |  |  |  |
| 1.216 |  |  |  |  |
| 1.217 |  |  |  |  |
| 1.218 |  |  |  |  |
| 1.219 | 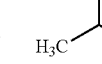 |  | 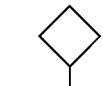 |  |
| 1.220 |  | 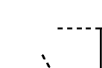 |  |  |
| 1.221 |  |  | 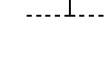 |  |
| 1.222 | 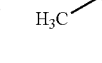 |  | 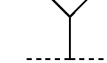 |  |
| 1.223 |  |  |  |  |
| 1.224 |  |  |  | |

TABLE 1-continued

| No. | R¹ | R² | ![R⁴/R⁵ group] | R⁸ |
|-----|-----|-----|-----|-----|
| 1.225 | 3-CF₃-C₆H₄-CH₂- | (CH₃)₂CH-CH₂- | -C(CH₃)₂-CH₃ | cyclopropyl |
| 1.226 | 3-CF₃-C₆H₄-CH₂- | (CH₃)₂CH-CH₂- | 1-methylcyclopropyl (spiro) | cyclopropyl |
| 1.227 | 3-CF₃-C₆H₄-CH₂- | (CH₃)₂CH-CH₂- | 1-methylcyclobutyl (spiro) | cyclopropyl |
| 1.228 | 3-CF₃-C₆H₄-CH₂- | (CH₃)₂CH-CH₂- | 1-methylcyclopentyl (spiro) | cyclopropyl |
| 1.229 | 3,5-(CF₃)₂-C₆H₃-CH₂- | (CH₃)₂CH-CH₂- | -C(CH₃)₂-CH₃ | cyclopropyl |
| 1.230 | 3,5-(CF₃)₂-C₆H₃-CH₂- | (CH₃)₂CH-CH₂- | 1-methylcyclopropyl (spiro) | cyclopropyl |
| 1.231 | 3,5-(CF₃)₂-C₆H₃-CH₂- | (CH₃)₂CH-CH₂- | 1-methylcyclobutyl (spiro) | cyclopropyl |
| 1.232 | 3,5-(CF₃)₂-C₆H₃-CH₂- | (CH₃)₂CH-CH₂- | 1-methylcyclopentyl (spiro) | cyclopropyl |

TABLE 1-continued

| No. | R¹ | R² | [R⁴/R⁵ group] | R⁸ |
|---|---|---|---|---|
| 1.233 | 4-F₃CO-C₆H₄- | -CH(CH₃)₂ | -C(CH₃)₂- (gem-dimethyl) | cyclopropyl |
| 1.234 | 4-F₃CO-C₆H₄- | -CH(CH₃)₂ | spiro-cyclopropyl | cyclopropyl |
| 1.235 | 4-F₃CO-C₆H₄- | -CH(CH₃)₂ | spiro-cyclobutyl | cyclopropyl |
| 1.236 | 4-F₃CO-C₆H₄- | -CH(CH₃)₂ | spiro-cyclopentyl | cyclopropyl |
| 1.237 | 5-F₃C-pyridin-2-yl | -CH(CH₃)₂ | -C(CH₃)₂- | cyclopropyl |
| 1.238 | 5-F₃C-pyridin-2-yl | -CH(CH₃)₂ | spiro-cyclopropyl | cyclopropyl |
| 1.239 | 5-F₃C-pyridin-2-yl | -CH(CH₃)₂ | spiro-cyclobutyl | cyclopropyl |
| 1.240 | 5-F₃C-pyridin-2-yl | -CH(CH₃)₂ | spiro-cyclopentyl | cyclopropyl |
| 1.241 | 4-F₃C-C₆H₄- | -CH(CH₃)₂ | -C(CH₃)₂- | tetrahydropyran-4-yl |

TABLE 1-continued

| No. | R¹ | R² | —C(R⁴)(R⁵)— | R⁸ |
|---|---|---|---|---|
| 1.242 | 4-F₃C-C₆H₄- | -CH(CH₃)₂ | 1-cyclopropyl (spiro) | tetrahydropyran-4-yl |
| 1.243 | 4-F₃C-C₆H₄- | -CH(CH₃)₂ | 1-cyclobutyl (spiro) | tetrahydropyran-4-yl |
| 1.244 | 4-F₃C-C₆H₄- | -CH(CH₃)₂ | 1-cyclopentyl (spiro) | tetrahydropyran-4-yl |
| 1.245 | 3-F₃C-C₆H₄- | -CH(CH₃)₂ | -C(CH₃)₂- | tetrahydropyran-4-yl |
| 1.246 | 3-F₃C-C₆H₄- | -CH(CH₃)₂ | 1-cyclopropyl (spiro) | tetrahydropyran-4-yl |
| 1.247 | 3-F₃C-C₆H₄- | -CH(CH₃)₂ | 1-cyclobutyl (spiro) | tetrahydropyran-4-yl |
| 1.248 | 3-F₃C-C₆H₄- | -CH(CH₃)₂ | 1-cyclopentyl (spiro) | tetrahydropyran-4-yl |
| 1.249 | 3,5-(F₃C)₂-C₆H₃- | -CH(CH₃)₂ | -C(CH₃)₂- | tetrahydropyran-4-yl |

TABLE 1-continued

| No. | R¹ | R² | ![R⁴R⁵] | R⁸ |
|---|---|---|---|---|
| 1.250 | 3,5-bis(CF₃)phenyl-CH₂- | -CH(CH₃)₂ | spiro[2.2]cyclopropyl | tetrahydropyran-4-yl |
| 1.251 | 3,5-bis(CF₃)phenyl-CH₂- | -CH(CH₃)₂ | spiro[3.3]cyclobutyl | tetrahydropyran-4-yl |
| 1.252 | 3,5-bis(CF₃)phenyl-CH₂- | -CH(CH₃)₂ | spiro[4.4]cyclopentyl | tetrahydropyran-4-yl |
| 1.253 | 4-(F₃CO)phenyl-CH₂- | -CH(CH₃)₂ | -C(CH₃)₂- | tetrahydropyran-4-yl |
| 1.254 | 4-(F₃CO)phenyl-CH₂- | -CH(CH₃)₂ | spiro[2.2]cyclopropyl | tetrahydropyran-4-yl |
| 1.255 | 4-(F₃CO)phenyl-CH₂- | -CH(CH₃)₂ | spiro[3.3]cyclobutyl | tetrahydropyran-4-yl |
| 1.256 | 4-(F₃CO)phenyl-CH₂- | -CH(CH₃)₂ | spiro[4.4]cyclopentyl | tetrahydropyran-4-yl |
| 1.257 | 5-(F₃C)pyridin-2-yl-CH₂- | -CH(CH₃)₂ | -C(CH₃)₂- | tetrahydropyran-4-yl |
| 1.258 | 5-(F₃C)pyridin-2-yl-CH₂- | -CH(CH₃)₂ | spiro[2.2]cyclopropyl | tetrahydropyran-4-yl |

TABLE 1-continued

| No. | R¹ | R² | (R⁴,R⁵ group) | R⁸ |
|---|---|---|---|---|
| 1.259 | 5-CF₃-pyridin-2-yl-methyl | isopropyl (H₃C-CH-CH₃) | 1,1-cyclobutyl spiro | tetrahydropyran-4-yl |
| 1.260 | 5-CF₃-pyridin-2-yl-methyl | isopropyl (H₃C-CH-CH₃) | 1,1-cyclopentyl spiro | tetrahydropyran-4-yl |

The compounds according to the invention may be obtained using methods of synthesis known in principle. Preferably the compounds are obtained by the following methods according to the invention which are described in more detail hereinafter.

The synthesis of compounds of formula I, wherein $R^1$-$R^8$ are defined as hereinbefore, can be carried out according to the invention related process a) shown in scheme 1 starting from compounds of formula II and III.

Scheme 1 (Process a)):

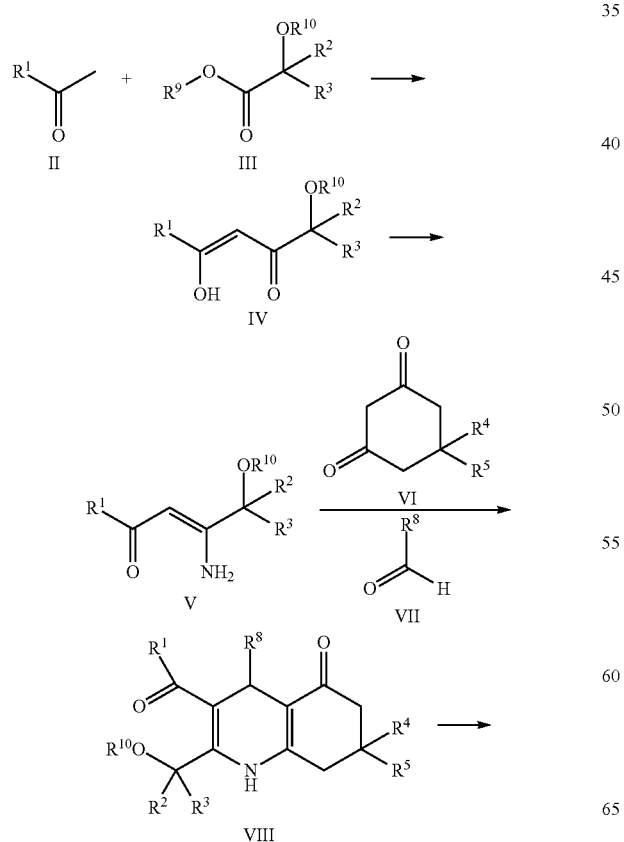

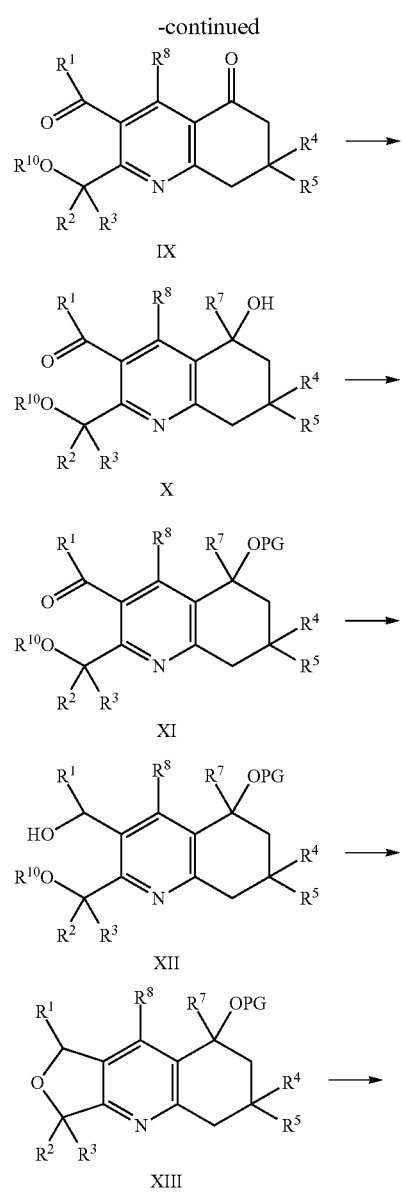

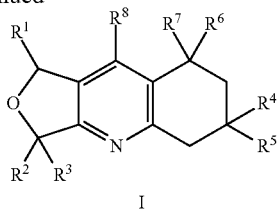

I

First step is the condensation of acetophenones of formula II with α-alkoxy-substituted esters of formula III, wherein $R^9$ and $R^{19}$ denote independently 1-3C-alkyl. This reaction is carried out in aprotic solvents like diethylether, tetrahydrofurane, dioxane or toluene in the presence of a base like potassium tert.-butoxide, sodium tert.-butoxide, potassium hydride, sodium hydride, lithium hexamethyldisilazide, sodium hexamethyldisilazide or potassium hexamethyldisilazide optionally in the presence of a crown ether like 15-crown-5(1,4,7,10,13-pentaoxacyclopentadecan) or 18-crown-6 (1,4,7,10,13,16-hexaoxacyclooctadecan) at temperatures between 0° C. and 180° C., but preferably between room temperature and 120° C. and yields the β-diketones of formula IV.

The β-diketones of formula IV can be transformed into the enaminoketones of formula V by reaction with ammonia or ammonium acetate in a solvent like for example methanol or ethanol at temperatures between 0° C. and 180° C., but preferably between room temperature and 120° C.

Condensation of the enaminoketones of formula V with the cyclic β-diketones of general formula VI and the aldehydes of formula VII in aprotic solvents like e.g. diethylether, diisopropylether, tetrahydrofurane, dioxane, dimethylformamide, acetonitril or toluene under the presence of an acid like for example acetic acid, trifluoroacetic acid, hydrochloric acid, sulphuric acid or pyridinium-para-toluenesulfonate at temperatures between 0° C. and 180° C., but preferably between room temperature and 120° C. yields the dihydropyridines of formula VIII.

The dihydropyridines of formula VIII can be oxidised to the pyridines of general formula IX by a suitable oxidating agent, such as e.g. 2,3-dichloro-5,6-dicyano-p-benzoquinone (DDQ) or ammonium cer-(IV)-nitrate in a solvent like e.g. dichloromethane, 1,2-dichloroethane, toluene, tetrahydrofurane, dioxane, dimethylfromamid or acetonitrile at temperatures between −20° C. and 120° C., but preferably between 0° C. and 80° C.

Reaction of compounds of formula IX with a hydride donating reagent like e.g. borane-tetrahydrofurane-complex, borane-dimethylsulfide-complex, borane-dimethylaniline-complex, borane-diethylaniline-complex, sodium borohydride, lithium borohydride, lithium aluminium hydride in a solvent like for example diethylether, tetrahydrofurane, dioxane or toluene at temperatures between −78° C. and 100° C., but preferably between −50° C. and 80° C., optionally in the presence of a chiral ligand as for example (1R,2S)-(+)-cis-1-Amino-2-indanol, (1S,2R)-(+)-cis-1-Amino-2-indanol, (R)-1-Methyl-3,3-diphenyl-tetrahydro-pyrrolo[1,2-c][1,3,2]oxazaborole or (S)-1-Methyl-3,3-diphenyl-tetrahydro-pyrrolo[1,2-c][1,3,2]oxazaborole gives the alcohols of formula X, wherein $R^7$ denotes H. The reduction in the presence of chiral ligands results in enantiomerically enriched compounds of formula X. For example the reduction with borane reagents like e.g. borane-tetrahydrofurane-complex, borane-dimethylsulfide-complex, borane-dimethylaniline-complex or borane-diethylaniline-complex in the presence of (1R,2S)-(+)-cis-1-Amino-2-indanole gives compounds of formula X with S-configuration at the newly formed stereocenter as is known from the literature (see Tetrahedron: Asymmetry 1995, 6, 301-306; Synthesis 1998, 937-961 or Angew. Chem. 1999, 111, 3574-3576).

Likewise, alkylation reaction of compounds of formula IX with a suitable alkyl metal compound, such as e.g. 1-4C-dialkylzinc-, 1-4C-alkylmagnesium halogenide-, or 1-4C-alkyllithium-reagent, particularly 1-3C-dialkylzinc-, 1-3C-alkylmagnesium halogenide-, or 1-3C-alkyllithium-reagent, in a solvent like e.g. hexane, cyclohexane, toluene, diethylether, tetrahydrofurane or dioxane, optionally in the presence of a chiral ligand as for example (R)-1-methyl-3,3-diphenyl-tetrahydro-pyrrolo[1,2-c][1,3,2]oxazaborole, (R)-1-methyl-3,3-diphenyl-tetrahydro-pyrrolo[1,2-c][1,3,2]oxazaborole, (−)-3-exo-dimethylamino-isoborneol, (+)-3-exo-dimethylamino-isoborneol or ligands as described in J. Am. Chem. Soc. 2002, 124, 10970-10971 or Tetrahedron 1998, 54, 5651-5666 at temperatures between −50° C. and 100° C., but preferably between −20° C. and 70° C., gives the corresponding alcohols of formula X, wherein $R^7$ denotes 1-4C-alkyl, particularly 1-3C-alkyl.

The alcohol group in compounds of formula X can be temporarily protected with a suitable protecting group, e.g. as a tert.-butyldimethylsilylether by the reaction with tert.-butyldimethylsilylchloride in a solvent like e.g. dimethylformamide or acetonitrile in the presence of imidazole at temperatures between −20° C. and 120° C., but preferably between 0° C. and 80° C., to give the protected derivatives of formula XI, in which PG stands for this suitable protecting group. This protection can also be carried out by reacting compounds of formula X with tert.-butyldimethylsilyl-trifluormethansulfonat in the presence of a base like for example pyridine or 2,6-lutidine in a solvent like e.g. dichloromethane, diethylether, tetrahydrofurane, dioxane or toluene at temperatures between −50° C. and 100° C. but preferably between −30° C. and 50° C. Alternatively any other suitable protecting group as described e.g. in "Protective Groups in Organic Synthesis", $2^{nd}$ edition, Greene T. W., Wuts P. G. M.; Wiley-Interscience: New York, 1991 or in "Protective Groups", Kocienski P. J.; Thieme: New York, 1994 can be used.

Reduction of the keto group in compounds of formula XI with a hydride donating reagent like e.g. lithium borohydride or lithium aluminium hydride in a solvent like for example diethylether, tetrahydrofurane, dioxane or toluene at temperatures between −40° C. and 120° C., but preferably between −10° C. and 80° C. gives the alcohols of formula XII.

These alcohols of formula XII can be cyclised to compounds of formula XIII by reaction with diethylamino-sulfurtrifluoride (DAST) or bis-(2-methoxyethyl)-amino-sulfurtrifluoride (BAST) in a aprotic solvent as for example dichloromethane, 1,2-dichloroethane, diethylether, tetrahydrofurane, acetonitrile or toluene, optionally in the presence of an iodide source as e.g. tetrabutylammonium iodide, caesium iodide, potassium iodide or sodium iodide, at temperatures between −78° C. and 100° C., but preferably between −50° C. and 60° C.

Deprotection of compounds of formula XIII, wherein PG denotes tert.-butyldimethylsilyl, preferably with a fluoride reagent like for example tetrabutylammonium fluoride or caesium fluoride or with an acid like for example trifluoroacetic acid, hydrochloric acid or sulphuric acid in a solvent like e.g. dichloromethane, 1,2-dichloroethane, diethylether, tetrahydrofurane, dioxane, acetonitrile or toluene at temperatures between −50° C. and 120° C., but preferably between −20° C. and 80° C. gives compounds of formula I, wherein $R^6$ denotes hydroxyl. Alternatively any other protecting group introduced before can be cleaved by suitable methods as described in the literature e.g. in "Protective Groups in Organic Synthesis", 2$^{nd}$ edition, Greene T. W., Wuts P. G. M.; Wiley-Interscience: New York, 1991 or in "Protective Groups", Kocienski P. J.; Thieme: New York, 1994.

In an alternative variant of above synthesis, the alcohols of formula XII can be also obtained from the corresponding aldehydes which are reacted with suitable R$^1$-metal reagents, such as e.g. R$^1$-magnesium halogenide- or R$^1$-lithium-reagent, in an aprotic solvent like e.g. diethylether, tetrahydrofurane, dioxane or toluene at temperatures between −78° C. and 80° C., but preferably between −50° C. and 40° C., e.g. via a Grignard reaction. The aldehydes used in this reaction are of formula XI, in which R$^1$ is hydrogen, and can be obtained from the corresponding carboxylic acids or acid esters, preferably from the ethyl esters which are of formula XI, in which R$^1$ is ethoxy, either by direct reduction to the aldehydes, or, preferably over two steps, by reduction to the primary alcohols (e.g. with the aid of a suitable hydride donating reagent such as LiAlH$_4$), which are then oxidized to the aldehydes (e.g. with the aid of a suitable oxidizing reagent such as Dess-Martin Periodinan). The carboxylic acid ethyl esters used in this reaction are of formula XI, in which R$^1$ is ethoxy, and can be obtained analogously or similarly to the reactions shown in scheme 1 (process a) starting from corresponding compounds of formula IV, in which R$^1$ is ethoxy. The compounds of formula IV, in which R$^1$ is ethoxy, can be obtained from corresponding ester compounds of formula III or their acids by aldol or claisen condensation, e.g. with malonic acid ethyl ester.

Compounds of formula I can be converted into further compounds of formula I, for example as follows:

Compounds of formula I, wherein R$^7$ denotes H and R$^6$ denotes hydroxyl can be oxidised to ketones of formula I, wherein R$^6$ and R$^7$ together denote carbonyl. This transformation can be carried out by a suitable oxidation agent, such as e.g. by oxidation with Dess-Martin-Periodinan (J. Chem. Soc. 1983, 48, 4156), by Swern oxidation (J. Org. Chem. 1976, 41, 957), or with pyridinium chlorochromate (PCC) or pyridinium dichromate in dichloromethane.

Compounds of formula I, wherein R$^6$ and R$^7$ together denote carbonyl can be transformed in compounds of formula I, wherein R$^6$ and R$^7$ together denote oxime, by an oxime formation reaction e.g. with hydroxylammonium chloride in methanol or ethanol in the presence of a base like e.g. sodium bicarbonate, sodium carbonate, potassium carbonate or caesium carbonate at temperatures between −10° C. and 150° C., but preferably between 0° C. and 120° C.

Starting from compounds of formula I, wherein R$^6$ denotes hydroxyl, compounds of formula I, wherein R$^6$ denotes F, can be prepared by fluorination reaction with a suitable fluorination agent, such as e.g. diethylamino-sulfur-trifluoride (DAST) or bis-(2-methoxyethyl)-amino-sulfur-trifluoride (BAST) in a aprotic solvent as for example dichloromethane, 1,2-dichloroethane, diethylether, tetrahydrofurane, acetonitrile or toluene at temperatures between −78° C. and 100° C., but preferably between −50° C. and 60° C.

Starting compounds of formulae II, III, VI and VII are known or can be obtained analogously or similarly to known procedures.

The synthesis of compounds of formula I, in which R$^1$ and R$^4$-R$^8$ are defined as hereinbefore and R$^2$ and R$^3$ denote both methyl, (i.e. compounds of formula I' as shown in scheme 2) can also be carried out according to the invention related process b) shown in scheme 2 starting from compounds of formulae XIV and VII.

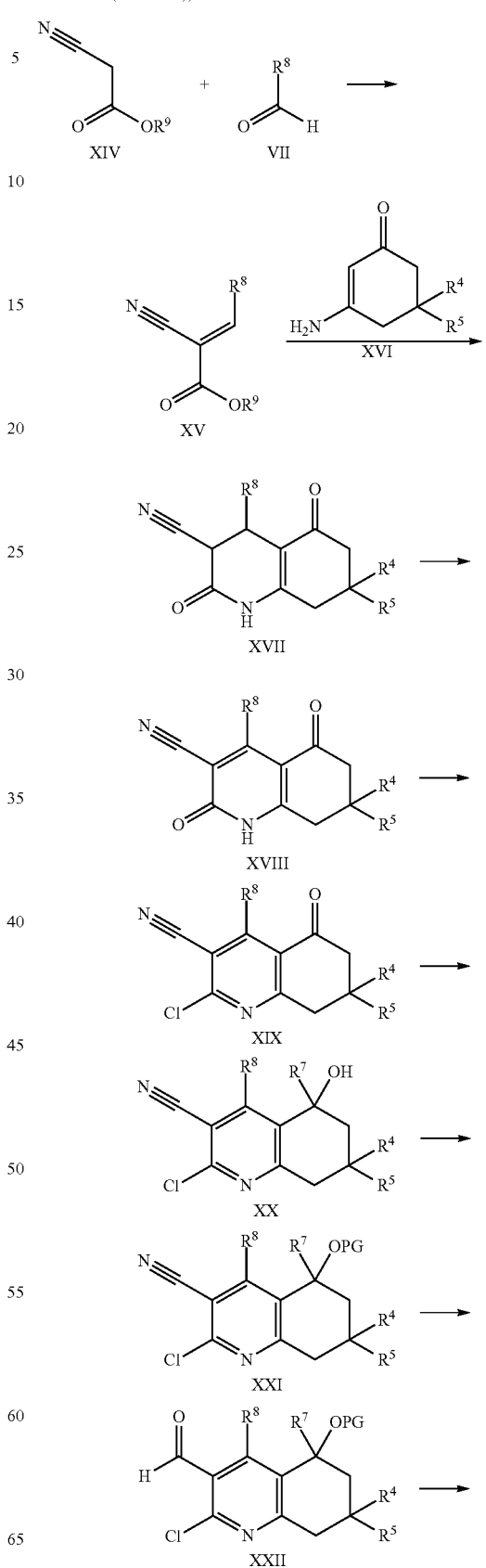

Scheme 2 (Process b)):

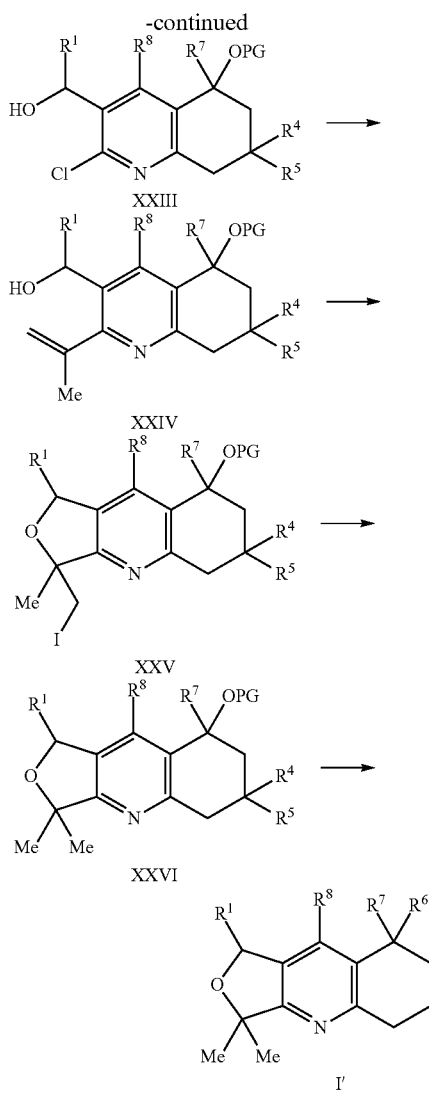

optionally in the presence of water as a cosolvent at temperatures between 0° C. and 180° C., but preferably between room temperature and 120° C.

Bicyclic pyridines of formula XIX can be prepared from bicyclic pyridones of formula XVIII by chlorination reaction with phosphorpentachloride, phosphoroxychloride or thionylchloride in dichloromethane, 1,2-dichloroethane or toluene optionally in the presence of dimethylformamide at temperatures between 0° C. and 180° C., but preferably between room temperature and 120° C.

Reaction of compounds of formula XIX with a hydride donating reagent like e.g. borane-tetrahydrofurane-complex, borane-dimethylsulfide-complex, borane-dimethylaniline-complex, borane-diethylaniline-complex, sodium borohydride, lithium borohydride, lithium aluminium hydride in a solvent like for example diethylether, tetrahydrofurane, dioxane or toluene at temperatures between −78° C. and 100° C., but preferably between −50° C. and 80° C., optionally in the presence of a chiral ligand as for example (1R,2S)-(+)-cis-1-Amino-2-indanol, (1S,2R)-(+)-cis-1-Amino-2-indanol, (R)-1-Methyl-3,3-diphenyl-tetrahydro-pyrrolo[1,2-c][1,3,2]oxazaborole or (S)-1-Methyl-3,3-diphenyl-tetrahydro-pyrrolo[1,2-c][1,3,2]oxazaborole gives the alcohols of formula XX, wherein $R^7$ denotes H.

Likewise, reaction of compounds of formula XIX with a suitable alkyl metal compound, such as e.g. 1-4C-dialkylzinc-, 1-4C-alkylmagnesium halogenide-, or 1-4C-alkyllithium-reagent, particularly 1-3C-dialkylzinc-, 1-3C-alkylmagnesium halogenide-, or 1-3C-alkyllithium-reagent, in a solvent like e.g. hexane, cyclohexane, toluene, diethylether, tetrahydrofurane or dioxane, optionally in the presence of a chiral ligand as for example (R)-1-methyl-3,3-diphenyl-tetrahydro-pyrrolo[1,2-c][1,3,2]oxazaborole, (R)-1-methyl-3,3-diphenyl-tetrahydro-pyrrolo[1,2-c][1,3,2]oxazaborole, (−)-3-exo-dimethylamino-isoborneol, (+)-3-exo-dimethylamino-isoborneol or ligands as described in *J. Am. Chem. Soc.* 2002, 124, 10970-10971 or *Tetrahedron* 1998, 54, 5651-5666 at temperatures between −50° C. and 100° C., but preferably between −20° C. and 70° C. gives the alcohols of formula XX, wherein $R^7$ denotes 1-4C-alkyl, particularly 1-3C-alkyl.

The alcohol group in compounds of formula XX can be temporarily protected with a suitable protecting group, e.g. as a tert.-butyldimethylsilylether by the reaction with tert.-butyldimethylsilylchloride in a solvent like e.g. dimethylformamide or acetonitrile in the presence of imidazole at temperatures between −20° C. and 120° C., but preferably between 0° C. and 80° C. to give the protected derivatives of formula XXI, in which PG stands for this suitable protecting group. This protection can also be carried out by reacting compounds of formula X with tert.-butyldimethylsilyl-trifluormethansulfonat in the presence of a base like for example pyridine or 2,6-lutidine in a solvent like e.g. dichloromethane, diethylether, tetrahydrofurane, dioxane or toluene at temperatures between −50° C. and 100° C. but preferably between −30° C. and 50° C. Alternatively any other suitable protecting group as described in "*Protective Groups in Organic Synthesis*", 2nd edition, Greene T. W., Wuts P. G. M.; Wiley-Interscience: New York, 1991 or in "*Protective Groups*", Kocienski P. J.; Thieme: New York, 1994 can be used.

The nitriles of formula XXI can be reduced to the aldehydes of formula XXII with a suitable reducing agent, such as e.g. diisobutylamuminium hydride in an aprotic solvent like e.g. dichloromethane, tetrahydrofurane, dioxane or toluene at temperatures between −78° C. and 100° C., but preferably between −30° C. and 50° C.

Knoevenagel condensation between cyanoacetic acid esters of formula XIV, wherein $R^9$ denotes 1-3C-alkyl and aldehydes of formula VII gives acrylic acid esters of formula XV. This reaction proceeds in an aprotic solvent like e.g. acetonitrile, dimethylformamide, tetrahydrofurane or dioxane in the presence of a base like e.g. piperidine, pyrrolidine, triethylamine or N,N-diisopropyl-N-ethyl-amine and in the presence of an acid like e.g. acetic acid or trifluoroacetic acid at temperatures between 0° C. and 150° C., but preferably between room temperature and 100° C.

Cyclization reaction of acrylic acid esters of formula XV with cyclic enaminoketones of formula XVI in a solvent like e.g. acetonitrile, dimethylformamide, tetrahydrofurane, dioxane or toluene in the presence of an acid like e.g. acetic acid or trifluoroacetic acid at temperatures between 0° C. and 200° C., but preferably between room temperature and 150° C. gives the bicyclic dihydropyridones of formula XVII.

These bicyclic dihydropyridones of formula XVII can be oxidised to the bicyclic pyridones of formula XVIII with a suitable oxidating agent, such as e.g. ammonium-cer-(IV)-nitrate or 2,3-dichloro-5,6-dicyano-p-benzoquinone (DDQ) in an organic solvent like e.g. acetonitrile, dimethylformamide, tetrahydrofurane, dioxane, dichloromethane or toluene Aldehydes of formula XXII are transformed to the alcohols of formula XXIII by reaction with a suitable $R^1$-metal reagent, such as e.g. $R^1$-magnesium halogenide- or $R^1$-lithium-reagent, in an aprotic solvent like e.g. diethylether, tetrahydrofurane, dioxane or toluene at temperatures between −78° C. and 80° C., but preferably between −50° C. and 40° C.

Subsequent reaction of alcohols of formula XXIII with prop-1-en-2-yl-boronic acid (which is prepared as described in J. Am. Chem. Soc. 2003, 125, 11148-49) or potassium prop-1-en-yl-trifluoroborate (which is prepared as described in J. Am. Chem. Soc. 2003, 125, 11148-49) according to a Suzuki reaction, e.g. in toluene, dimethylformamide, acetonitrile, dioxane or tetrahydrofurane or mixtures of toluene and tetrahydrofurane in the presence of a base as for example aqueous sodium carbonate, aqueous potassium carbonate, aqueous caesium carbonate, silver carbonate triethylamine or N,N-diisopropyl-N-ethyl-amine and in the presence of a catalyst like tetrakis-triphenylphosphine-palladium-(0), bis-tri-tert.-butylphosphine-palladium-(0), 1,1'-bis-(diphenylphosphino)-ferrocene-dichloro-palladium-(II) or bis-[1,2-bis-(diphenylphosphino)-ethane]-palladium-(0) at temperatures between 0° C. and 180° C., but preferably between room temperature and 120° C., gives compounds of formula XXIV. In this reaction also cyclopent-1-enyl-boronic acid can be used instead of prop-1-en-2-yl-boronic acid or potassium prop-1-en-yl-trifluoroborate. By this and after analogous reactions as described for compounds of formula XXIV in this process b) compounds of formula I', in which the two methyl groups of the dihydrofurane ring together with the carbon to which they are connected denote a cyclopentane ring, are obtained.

Alternatively compounds of formula XXIV can be prepared from compounds of formula XXIII in three steps. First step is the oxidation of the alcohol to the ketone which can be carried out with Dess-Martin-Periodinan (J. Chem. Soc. 1983, 48, 4156), by Swern oxidation (J. Org. Chem. 1976, 41, 957), or with pyridinium chlorochromate (PCC) or pyridinium dichromate in dichloromethane. Second step is the Suzuki reaction with prop-1-en-2-yl-boronic acid. This reaction proceeds in toluene, dimethylformamide, acetonitrile, dioxane or tetrahydrofurane or mixtures of toluene and tetrahydrofurane in the presence of a base such as for example aqueous sodium carbonate, aqueous potassium carbonate, aqueous caesium carbonate, silver carbonate, triethylamine or N,N-diisopropyl-N-ethyl-amine and in the presence of a catalyst like tetrakis-triphenylphosphine-palladium-(0), bis-tri-tert.-butylphosphine-palladium-(0), 1,1'-bis-(diphenylphosphino)-ferrocene-dichloro-palladium-(II) or bis-[1,2-bis-(diphenylphosphino)-ethane]-palladium-(0) at temperatures between 0° C. and 180° C., but preferably between room temperature and 120° C. Third step is the reduction of the ketone to the alcohols of formula XXIV with a hydride donating reagent like e.g. lithium borohydride or lithium aluminium hydride in a solvent like for example diethylether, tetrahydrofurane, dioxane or toluene at temperatures between −40° C. and 120° C., but preferably between −10° C. and 80° C. In the Suzuki reaction here also cyclopent-1-enyl-boronic acid or cyclohex-1-enyl-boronic acid or their respective trifluoroborates can be used instead of prop-1-en-2-yl-boronic acid or potassium prop-1-en-yl-trifluoroborate. By this and after analogous reactions as described for compounds of formula XXIV in this process b) compounds of formula I'-a, in which the two methyl groups of the dihydrofurane ring together with the carbon to which they are connected denote a cyclopentane or cyclohexane ring, are obtained as depicted in Scheme 3 (Process c)).

Scheme 3 (Process c)):

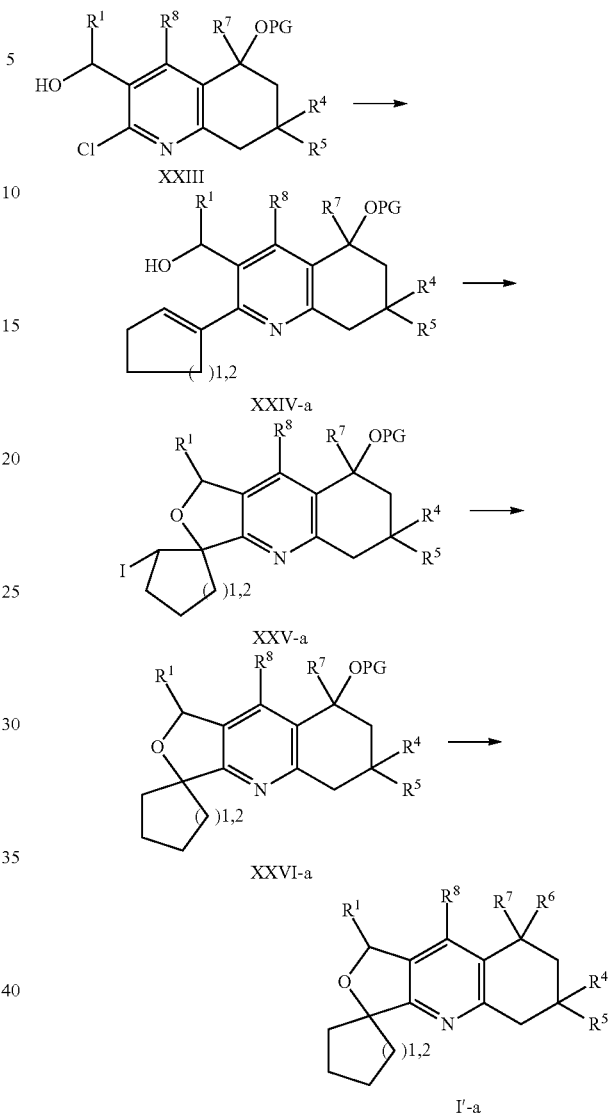

Compounds of formula XXIV are then reacted with iodine or N-iodosuccinimide in acetonitrile, dimethylformamide, tetrahydrofurane or dioxane in the presence of a base like e.g. sodium bicarbonate, sodium carbonate, potassium carbonate, triethylamine or N,N-diisopropyl-N-ethyl-amine and in the presence of silver-(I)-oxide, silver-(I)-nitrate or silver-(I)-trifluoroacetate at temperatures between −40° C. and 100° C., but preferably between −10° C. and 60° C. to yield the compounds of formula XXV.

These compounds of formula XXV are reduced to the compounds of formula XXVI with a suitable reducing agent, such as e.g. tris-trimethylsilylsilane or tributyltin hydride in the presence of a radical starter like azo-bis-isobutyronitrile or dibenzoylperoxide in carbontetrachloride, benzene or toluene at temperatures between 80° C. and 150° C. Alternatively compounds of formula XXV can be reduced to compounds of formula XXVI by hydrogenation in the presence of a catalyst as for example palladium on charcoal or palladiumhydroxide on charcoal in a solvent like e.g. methanol, ethanol, tetrahydrofurane or dioxane but preferably methanol. This reaction can be carried out in the presence of a base like for example triethylamine or N,N-diisopropyl-N-ethyl-amine at temperatures between −20° C. and 100° C. but preferably between 0° C. and 80° C.

Deprotection of compounds of formula XXVI, wherein PG denotes tert.-butyldimethylsilyl, preferably with a fluoride reagent like for example tetrabutylammonium fluoride or caesium fluoride or with an acid like for example trifluoroacetic acid, hydrochloric acid or sulphuric acid in a solvent like e.g. dichloromethane, 1,2-dichloroethane, diethylether, tetrahydrofurane, dioxane, acetonitrile or toluene at temperatures between −50° C. and 120° C., but preferably between −20° C. and 80° C. gives compounds of formula I', wherein $R^6$ denotes hydroxyl. Alternatively any other protecting group introduced before can be cleaved by suitable methods as described in the literature e.g. in "*Protective Groups in Organic Synthesis*", $2^{nd}$ edition, Greene T. W., Wuts P. G. M.; Wiley-Interscience: New York, 1991 or in "*Protective Groups*", Kocienski P. J.; Thieme: New York, 1994.

Compounds of formula I' can be converted into further compounds of formula I', for example as follows:

Compounds of formula I', wherein $R^7$ denotes H and $R^6$ denotes hydroxyl can be oxidised to ketones of formula I', wherein $R^6$ and $R^7$ together denote carbonyl. This transformation can be carried by a suitable oxidation agent, such as e.g. by oxidation with Dess-Martin-Periodinan (*J. Chem. Soc.* 1983, 48, 4156), by Swern oxidation (*J. Org. Chem.* 1976, 41, 957), or with pyridinium chlorochromate (PCC) or pyridinium dichromate in dichloromethane.

Compounds of formula I', wherein $R^6$ and $R^7$ together denote carbonyl can be transformed in compounds of formula I', wherein $R^6$ and $R^7$ together denote oxime, by oxime formation reaction e.g. with hydroxylammonium chloride in methanol or ethanol in the presence of a base like e.g. sodium bicarbonate, sodium carbonate, potassium carbonate or caesium carbonate at temperatures between −10° C. and 150° C., but preferably between 0° C. and 120° C.

Starting from compounds of formula I', wherein $R^6$ denotes hydroxyl, compounds of formula I', wherein $R^6$ denotes F, can be prepared by fluorination reaction with a suitable fluorination agent, such as e.g. diethylamino-sulfur-trifluoride (DAST) or bis-(2-methoxyethyl)-amino-sulfur-trifluoride (BAST) in a aprotic solvent as for example dichloromethane, 1,2-dichloroethane, diethylether, tetrahydrofurane, acetonitrile or toluene at temperatures between −78° C. and 100° C., but preferably between −50° C. and 60° C.

Starting compounds of formulae XIV and XVI are known or can be obtained analogously or similarly to known procedures.

Besides the strategies presented a host of additional approaches can be envisaged. Therefore, the preceding strategies are in no way meant to restrict the possible synthetic pathways to access the compounds of the invention but are only supposed to show a few routes by way of example.

It is moreover known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in "Protective Groups in Organic Synthesis" by T. Greene and P. Wuts (John Wiley & Sons, Inc. 1999, 3rd Ed.) or in "Protecting Groups (Thieme Foundations Organic Chemistry Series N Group" by P. Kocienski (Thieme Medical Publishers, 2000).

In the reactions described hereinbefore, any reactive groups present such as carboxy-, carbonyl-, hydroxy-, amino-, alkylamino- or imino-groups may be protected during the reaction by conventional protecting groups which are cleaved again after the reaction.

For example, a protecting group for a carboxy group may be the methyl-, ethyl-, tert.-butyl- or benzyl-group.

For example, a protecting group for a carbonyl group may be an acetal or ketal like the 1,3-dioxolane- or the 1,3-dioxane-group.

For example, a protecting group for a hydroxy group may be a trimethylsilyl-, tert.-butyldimethylsilyl-, acetyl-, trityl-, benzyl- or tetrahydropyranyl-group.

Protecting groups for an amino, alkylamino or imino group may be, for example, a formyl, acetyl, trifluoroacetyl, ethoxycarbonyl, tert.butoxycarbonyl, benzyloxycarbonyl, benzyl, methoxybenzyl or 2,4-dimethoxybenzyl group.

The cleavage of a carboxymethyl- or a carboxyethyl-group can for example be carried out hydrolytically in an aqueous solvent, e.g. in water, methanol/water, isopropanol/water, acetic acid/water, tetrahydrofuran/water or dioxane/water, in the presence of an acid such as trifluoroacetic acid, hydrochloric acid or sulphuric acid or in the presence of an alkali base as for example lithium hydroxide, sodium hydroxide or potassium hydroxide, but preferably sodium hydroxide, or aprotically in the presence of e.g. iodotrimethylsilane, at temperatures between 0 and 120° C., preferably at temperatures between 10 and 100° C.

An acetal or ketal can be cleaved with acetic acid, trifluoroacetic acid, hydrochloric acid, sulphuric acid or pyridiumium-p-toluene sulfonate in mixtures with water or in organic solvents like for example dichloromethane, 1,2-dichloroethane, tetrahydrofurane, dioxane, toluene or acetone at temperatures between −20° C. and 150° C., but preferably between 0° C. and 120° C.

A benzyl, methoxybenzyl or benzyloxycarbonyl group is advantageously cleaved hydrogenolytically, e.g. with hydrogen in the presence of a catalyst such as palladium/charcoal in a suitable solvent such as methanol, ethanol, ethyl acetatetetrahydrofurane, dioxane or glacial acetic acid, optionally with the addition of an acid such as hydrochloric acid at temperatures between 0 and 100° C., but preferably at ambient temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid or by treating with iodotrimethylsilane optionally using a solvent such as dichloromethane, dioxane, methanol or diethylether.

A trimethylsilyl- or tert.-butyldimethylsilyl-group is cleaved with a fluoride reagent like for example tetrabutylammonium fluoride or caesium fluoride or with an acid like for example trifluoroacetic acid, hydrochloric acid or sulphuric acid in a solvent like e.g. dichloromethane, 1,2-dichloroethane, diethylether, tetrahydrofurane, dioxane, acetonitrile or toluene at temperatures between −50° C. and 120° C., but preferably between −20° C. and 80° C.

The present invention also relates to intermediates (including their salts, stereoisomers and salts of these stereoisomers), methods and processes which are disclosed herein and which are useful in synthesizing final compounds according to this invention. Thus, the present invention also relates to processes disclosed herein for preparing compounds according to this invention, which processes may be performed as described herein. Said processes may comprise one or more steps of converting and/or reacting the mentioned intermediates with the appropriate reaction partners, suitably under conditions as disclosed herein.

Moreover, the compounds of general formula I or intermediates in the synthesis of compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I or intermediates in the synthesis of compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I or intermediates in the synthesis of compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column chromatography on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyl-tartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-methyloxycarbonyl.

For compounds according to structural formula I in which $R^1$ is 4-trifluoromethyl-phenyl, $R^2$ is methyl, $R^3$ is hydrogen, $R^4$ is methyl, $R^5$ is methyl, $R^6$ is hydroxyl, $R^7$ is hydrogen and $R^8$ is cyclopentyl, it has been discovered that the diastereomer described as Diastereomer 3 in the following examples (Example 1 (2)) exhibit higher CETP inhibitory potency as compared to the other diastereomers.

Thus, it is expected that any stereoisomer corresponding in absolute stereochemical configuration to that stereoisomer which is described as Diastereomer 3 of Example 1 (2) in the following examples will exhibit similar higher potency as compared to the other stereoisomers.

It has been found for the structure of Diastereomer 3 of Example 1 (2) that the substituents bound in positions 1 and 3 are trans relatively to each other, and, when the configuration in position 8 is assigned to S configuration, the configuration in position 1 is S and the configuration in position 3 is S.

Hence, for compounds according to structural formula I in which $R^1$ is 4-trifluoromethyl-phenyl, $R^2$ is methyl, $R^3$ is hydrogen, $R^4$ is methyl, $R^5$ is methyl, $R^6$ is hydroxyl, $R^7$ is hydrogen and $R^8$ is cyclopentyl, it has been further discovered that, when the configuration in position 8 is assigned to S, the trans (1S,3S) diastereomer exhibit higher CETP inhibitory potency as compared to the other diastereomers.

Thus, it is expected that any stereoisomer corresponding in absolute stereochemical configuration to this (1S,3S,8S) stereoisomer, i.e. compounds of structural formula Ia* according to the present invention, will exhibit similar higher potency as compared to the other stereoisomers.

For compounds according to structural formula I in which $R^1$ is 4-trifluoromethyl-phenyl, $R^2$ is methyl, $R^3$ is methyl, $R^4$ is methyl, $R^5$ is methyl, $R^6$ is hydroxyl, $R^7$ is hydrogen and $R^8$ is cyclopentyl, it has been discovered that the diastereomer described as Example 1 (5) in the following examples exhibit higher CETP inhibitory potency as compared to the other diastereomer.

Thus, it is expected that any stereoisomer corresponding in absolute stereochemical configuration to that stereoisomer which is described as Example 1 (5) in the following examples will exhibit similar higher potency as compared to the other stereoisomers.

Moreover, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid. Corresponding processes are known for the skilled person.

When one of the final steps (e.g. removing an acid- or base-labile protecting group from a suitable precursor) or purification is carried out under the presence of an inorganic or organic acid (e.g. hydrochloric, trifluoroacetic, acetic or formic acid or the like) or a base, the compounds of formula I may be obtained—depending on their individual chemical nature and the individual nature of the acid or base used—as free compound or containing said acid or base in an stoichiometric or non-stoichiometric quantity (e.g. as a salt). The acid/base contained can be analyzed according to art-known procedures, e.g. by titration or NMR, and, optionally, removed according to procedures familiar to the skilled person.

Optionally, salts of the compounds of the formula I may be converted into the free compounds. Corresponding processes are known to the skilled person, e.g. via neutralization.

Salts can be obtained by reacting the free compounds with the desired acids or bases, e.g. by dissolving the free compound in a suitable solvent (e.g. a ketone, such as acetone, methyl ethyl ketone or methyl isobutyl ketone, an ether, such as diethyl ether, diisopropyl ether, tetrahydrofuran or dioxane, a chlorinated hydrocarbon, such as methylene chloride or chloroform, a low-molecular-weight aliphatic alcohol, such as methanol, ethanol or isopropanol, or an ester, such as ethyl acetate) which contains the desired acid or base, or to which the desired acid or base is then added. The salts can be obtained by filtering, reprecipitating, precipitating with a nonsolvent for the addition salt or by evaporating the solvent. Salts obtained can be converted to another, e.g. reaction with an appropriate acid or base or by means of a suitable ion exchanger. Likewise, salts obtained can be converted into the free compounds, which can in turn be converted into salts, by alkalization or by acidification. In this manner, physiologically unacceptable salts can be converted into physiologically acceptable salts.

The substances according to the invention are isolated and purified in a manner known per se, for example by distilling off the solvent under reduced pressure and recrystallizing the residue obtained from a suitable solvent or subjecting it to one of the customary purification methods, such as, for example, column chromatography on a suitable support material.

The compounds according to the invention are advantageously obtainable using the methods described in the examples that follow, which may also be combined for this purpose with methods known to the skilled person from his/her expert knowledge. Likewise, further compounds according to this invention, whose preparation are not explicitly described in the following examples, can be prepared analogously or similarly to the examples.

Any or all of the compounds according to the present invention which are mentioned as final compounds in the following examples, including the salts, stereoisomers and salts of the stereoisomers thereof, are a particularly interesting subject within the present invention.

As already mentioned, the compounds of general formula I according to the invention and the physiologically acceptable salts thereof have valuable pharmacological properties, particularly an inhibitory effect on the enzyme cholesterol ester transfer protein (CETP).

The biological properties of the new compounds may be investigated as follows:

CETP Scintillation Proximity Assay

Compounds of the present invention inhibit CETP-dependent cholesterol ester transfer from HDL to LDL as described here. Recombinant human CETP is partially purified from medium conditioned by CETP expressing CHO cells. In a 96 well homogeneous assay format CETP transfers $^3$H-labelled cholesteryl esters from human HDL donor particles to biotin labelled LDL particles. Following over night incubation at room temperature the reaction is stopped by addition of streptavidin-coupled scintillation proximity assay (SPA) beads. These beads captured the biotinylated acceptor particles and the radioactivity is measured. The assay system is purchased and performed according to the manufacturer's recommendations (GE Healthcare).

Inhibitory activity of compounds is determined as percentage of positive control activity containing CETP together with donor and acceptor particles. Background activity is determined by adding buffer instead of CETP. Serial dilution of compound in buffer containing 10% DMSO is performed in order to determine the $IC_{50}$ values.

Representative compounds according to this invention may for example have $IC_{50}$ values for CETP inhibitory activity below 20000 nM. Advantageous compounds of this invention may for example have $IC_{50}$ values below 5000 nM, preferably below 2000 nM, more preferably below 1000 nM.

Thus, for example, Example 1, Example 1 (1), Diastereomer 3 of Example 1 (2) as well as Diastereomer 4 of Example 1 (2) have all $IC_{50}$ values below 2000 nM. In particular, Diastereomer 3 of Example 1 (2) has an $IC_{50}$ value below 1000 nM.

For other example, Diastereomer 1 and 2 of Example 1 (3) show $IC_{50}$ values below 20000 nM.

For other example, Example 1 (4) shows an $IC_{50}$ value below 5000 nM, Example 1 (5) shows an $IC_{50}$ value below 1000 nM, and Example 1 (6) shows an $IC_{50}$ below 20000 nM.

For other example, Example 1 (7) has an $IC_{50}$ value below 1000 nM.

For other example, Examples 1 (8), 2 and 1 (10) to 1 (13) show $IC_{50}$ values below 5000 nM.

In particular, Examples 1 (8) and 1 (10) have $IC_{50}$ values below 1000 nM.

For other example, Examples 1 (9) and 1 (14) to 1 (16) have $IC_{50}$ values below 20000 nM.

The compounds of formula I and their physiologically acceptable salts according to the present invention have valuable pharmacological properties which make them commercially applicable. Thus, for example, these compounds can act as inhibitors of CETP and are expected to be commercially applicable in the therapy of diseases responsive to the inhibition of CETP, such as e.g. any of those diseases mentioned herein.

In the context of their properties, functions and usabilities mentioned herein, the compounds according to the present invention may be distinguished by valuable and desirable effects related therewith, such as e.g. by high efficacy, high selectivity, low toxicity, superior bioavailability in general (such as e.g. good enteral absorption), superior therapeutic window, absence of significant side effects, and/or further beneficial effects related with their therapeutic, pharmacological and/or pharmaceutical suitability.

In view of their ability to inhibit enzyme cholesterol ester transfer protein (CETP), the compounds of general formula I according to the invention and the corresponding physiologically acceptable salts thereof are theoretically suitable for the treatment and/or prevention of all those conditions or diseases which may be affected by the inhibition of the cholesterol ester transfer protein (CETP) activity. Therefore, compounds according to the invention are particularly suitable for the treatment and/or prevention of cardiovascular and/or related disorders, in particular atherosclerosis, peripheral vascular disease, dyslipidemia, hyperbeta-lipoproteinemia, hypercholesterolemia, hypertriglyceridemia, familial hypercholesterolemia, angina, ischemia, cardiac ischemia, stroke, myocardial infarction, reperfusion injury, angioplastic restenosis, hypertension, vascular complications of diabetes, prevention of diabetes, insulin resistance, obesity or endotoxemia.

The compounds of formula I and their pharmaceutically acceptable salts can be used as medicaments, e.g. in the form of pharmaceutical compositions for enteral, parenteral or topical administration. They can be administered in any of the generally accepted modes of administration available in the art, e.g., perorally, e.g. in the form of tablets, coated tablets, dragees, hard and soft gelatine capsules, solutions, emulsions or suspensions, rectally, e.g. in the form of suppositories, parenterally (including intravenously), e.g. in the form of injection solutions or infusion solutions, or topically, e.g. in the form of ointments, creams or oils. Among the possible modes of administration, oral and intravenous delivery are preferred.

The pharmaceutical compositions according to this invention contain at least one of the compounds of the invention (=active compound), e.g. in a total amount of from 0.1 to 99.9 wt %, 5 to 95 wt %, or 20 to 80 wt %, optionally together with pharmaceutically acceptable auxiliaries.

The person skilled in the art is familiar with pharmaceutically acceptable auxiliaries, such as e.g. excipients, diluents, vehicles, carriers, additives and/or adjuvants which are known to be suitable for preparing pharmaceutical compositions, on account of his/her expert knowledge.

As pharmaceutically acceptable auxiliaries, usually any auxiliaries known to be appropriate for pharmaceutical compositions come into consideration. Examples thereof include, but are not limited to, solvents, excipients, diluents, dispersants, emulsifiers, solubilizers, gel formers, ointment bases, antioxidants, preservatives, stabilizers, carriers, fillers, binders, thickeners, complexing agents, disintegrating agents, buffers, pH regulators (e.g. to obtain neutral, alkaline or acidic formulations), permeation promoters, polymers, lubricants, coating agents, propellants, tonicity adjusting agents, surfactants, colorants, flavorings, sweeteners and dyes.

In general, suitable carrier materials are not only inorganic carrier materials, but also organic carrier materials. Thus, e.g., lactose, corn starch or derivatives thereof, talc, stearic acid or its salts can be used as carrier materials for tablets, coated tablets, dragees and hard gelatine capsules. Suitable carrier materials for soft gelatine capsules are, e.g., vegetable oils, waxes, fats and semi-solid and liquid polyols. Suitable carrier materials for the production of solutions and syrups are, e.g., water, polyols, sucrose, invert sugar and the like. Suitable carrier materials for injection solutions are, e.g., water, alcohols, polyols, glycerol and vegetable oils. Suitable carrier materials for suppositories are, e.g., natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

In particular, auxiliaries of a type appropriate to the desired pharmaceutical composition, formulation or preparation and the desired mode of administration are used.

The pharmaceutical compositions according to this invention can be prepared by processes which are known per se and familiar to the person skilled in the art, e.g. by incorporating the described compounds of formula I or their pharmaceutically acceptable salts (optionally combined with other active substances) optionally together with one or more conventional carriers (e.g. solid or liquid carriers) and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into conventional galenic preparations such as plain or coated tablets, capsules, powders, suspensions or suppositories.

The dosage of the compounds of the invention (=active compounds) can vary within wide limits depending on the compound which is to be administered, the nature and gravity of the disease to be treated or prevented, the age and the individual condition of the patient and the mode and frequency of administration, and will, of course, be fitted to the individual requirements in each particular case. Usually, a dosage of the compounds of the invention (=active compounds) in the order of magnitude customary for CETP inhibitors comes into consideration. Expediently, the dosage may be from 0.1 ng/ml to 10 mg/ml, preferably 1 ng/ml to 10 mg/ml, by intravenous route, and 0.1 to 2000 mg, preferably 1 to 100 mg, by oral route, in each case administered 1 to 4 times a day. Depending on the dosage it may be convenient to administer the daily dosage in several dosage units.

The compounds according to the invention may also be used in conjunction with other active substances, particularly for the treatment and/or prevention of the diseases, disorders and conditions mentioned above.

Other active substances which are suitable for such a combination include for example those which potentiate the therapeutic effect of a cholesterol ester transfer protein (CETP) inhibitor according to the invention with respect to one of the indications mentioned and/or which allow the dosage of a cholesterol ester transfer protein (CETP) inhibitor according to the invention to be reduced.

Therapeutic agents which are suitable for such a combination include particularly one or more lipid modulating agents. Lipid modulating agents comprise HMG CoA reductase inhibitors (e.g. simvastatin, atorvastatin), fibrates (e.g. bezafibrate, fenofibrate), PPAR (α, γ or α/γ) agonists or modulators, ACAT inhibitors (e.g. avasimibe), MTP inhibitors, squalene cyclase and squalene synthase inhibitors, LXR agonists or modulators, bile acid-binding substances such (e.g. cholestyramine), cholesterol absorption inhibitors (e.g. ezetimibe), niacin, PCSK9 inhibitors, bile acid reuptake inhibitors and lipase inhibitors.

Other therapeutic agents which are suitable for such a combination include one or more antidiabetic agents as for example metformin, alpha-glucosidase inhibitors (e.g. acarbose, voglibose), PPAR (α, γ or α/γ) agonists or modulators, DPPIV inhibitors (e.g. Sitagliptin, Vildagliptin), SGLT 2 inhibitors (e.g. dapagliflozin, sergliflozin), GLP-1 and GLP-1 analogues (e.g. exendin-4), insulin or insulin analogues, sulphonylureas (e.g. glibenclamide, tolbutamide, glimepiride), thiazolidinediones (e.g. rosiglitazone, pioglitazone), nateglinide, repaglinide, glucose-6-phosphatase inhibitors, fructose-1,6-bisphosphatase inhibitors, glycogen phosphorylase inhibitors, glucagon receptor antagonists, inhibitors of phosphoenol pyruvate carboxykinase, glycogen synthase kinase or pyruvate dehydrokinase and glucokinase activators.

Also suitable for such a combination are one or more antiobesity agents including for example sibutramine, tetrahydrolipostatin, leptin, leptin mimetics, antagonists of the cannabinoid) receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure or chronic heart failure such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, tasosartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

The therapeutic agents mentioned herein above as combination partners of the compounds according to this invention are meant to include pharmaceutically acceptable derivatives thereof, such as e.g. their pharmaceutically acceptable salts. The person skilled in the art is aware on the base of his/her expert knowledge of the kind, total daily dosage(s) and administration form(s) of the additional therapeutic agent(s) coadministered. Said total daily dosage(s) can vary within a wide range. Usually, the dosage for the combination partners mentioned above is 1/5 of the lowest dose normally recommended up to 1/1 of the normally recommended dose.

In practicing the present invention, the compounds according to this invention may be administered in combination therapy separately, sequentially, simultaneously, concurrently or chronologically staggered with one or more additional active substances, such as e.g. any of the therapeutic agents mentioned herein above as a combination partner.

In this context, the present invention further relates to a combination comprising a first active ingredient, which is at least one compound according to this invention, and a second active ingredient, which is at least one of the active substances described above as a combination partner, for separate, sequential, simultaneous, concurrent or chronologically staggered use in therapy, particularly for treatment and/or prevention of cardiovascular disorders, such as e.g. any of those mentioned herein.

Further, this invention relates to the use of a compound according to this invention combined with at least one of the active substances described above as a combination partner, for preparing a pharmaceutical composition which is suitable for the treatment or prevention of diseases or conditions which may be affected by the inhibition of the cholesterol ester transfer protein (CETP) activity, particularly cardiovascular disorders, more particularly one of the diseases, disorders or conditions listed above.

Further, this invention relates to a pharmaceutical composition which comprises a compound according to the invention and at least one of the active substances described above as combination partners, optionally together with one or more inert carriers and/or diluents.

The term "combination" according to this invention may be present as a fixed combination, a non-fixed combination, a free combination or a kit-of-parts.

A "fixed combination" is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration. Another example of a "fixed combination" is a pharmaceutical combination wherein the said first active ingredient and the said second active ingredient are present in one unit without being in admixture.

A "kit-of-parts" is defined as a combination wherein the said first active ingredient and the said second active ingredient are present in more than one unit. One example of a "kit-of-parts" is a combination wherein the said first active ingredient and the said second active ingredient are present separately. The components of the kit-of-parts may be administered separately, sequentially, simultaneously, concurrently or chronologically staggered.

The first and second active ingredient of a kit-of-parts according to this invention may be provided as separate formulations (i.e. independently of one another), which are subsequently brought together for simultaneous, concurrent, sequential, separate or chronologically staggered use in combination therapy; or packaged and presented together as separate components of a combination pack for simultaneous, concurrent, sequential, separate or chronologically staggered use in combination therapy.

The type of pharmaceutical formulation of the first and second active ingredient of a kit-of-parts according to this invention can be similar, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to this invention may together comprise a therapeutically effective amount, particularly for the treatment and/or prevention of the diseases, disorders and conditions mentioned above.

Other features and advantages of the present invention will become apparent from the following examples. The following examples serve to illustrate, by way of example, the principles of the invention without restricting it.

EXAMPLES

HPLC Methods:
Method 1: Column: Daicel AD-H, 250×4.6 mm, 5 μm, 10° C.; Eluent: Hexane ((+0.2% Diethylamine)/Methanol:Ethanol (50:50): 95/5, 1 ml/min; UV-Detection: 300 nm Method 2: Column: Merck Cromolith Speed ROD, RP18e, 50×4.6 mm; 1.5 ml/min; UV-Detection: 230 nm/254 nm; Eluent A: Water (0.1% Formic acid), Eluent B: Acetonitrile (0.1% Formic acid)

| Gradient: | |
| --- | --- |
| Time (min.) | % Eluent B |
| 0.00 | 10 |
| 4.50 | 90 |
| 5.00 | 90 |
| 5.50 | 10 |

Method 3: Column: Agilent Zorbax Bonus RP, 50×2.1 mm, 3.5 μm; 1.2 ml/min; UV-Detection: 230 nm/254 nm; Eluent A: Water (0.1% Formic acid), Eluent B: Acetonitrile (0.1% Formic acid)

| Gradient: | |
| --- | --- |
| Time (min.) | % Eluent B |
| 0.00 | 10 |
| 4.50 | 99 |
| 5.00 | 99 |
| 5.50 | 10 |

Method 4: Column: Agilent Zorbax Bonus RP, 50×2.1 mm, 3.5 μm; 1.2 ml/min; UV-Detection: 230 nm/254 nm; Eluent A: Water (0.1% Formic acid), Eluent B: Acetonitrile (0.1% Formic acid)

| Gradient: | |
| --- | --- |
| Time (min.) | % Eluent B |
| 0.00 | 10 |
| 1.00 | 75 |
| 1.30 | 75 |
| 2.30 | 99 |
| 4.44 | 99 |
| 5.00 | 10 |

Method 5: Column: YMC-Pack Pro 18, 50×4.6 mm, 3 μm; 1.2 ml/min; UV-Detection: 230 nm/254 nm; Eluent A: Water (0.1% Formic acid), Eluent B: Acetonitrile (0.1% Formic acid)

| Gradient: | |
| --- | --- |
| Time (min.) | % Eluent B |
| 0.00 | 5 |
| 0.75 | 5 |
| 1.00 | 50 |
| 5.25 | 98 |
| 5.75 | 98 |
| 6.05 | 5 |
| 6.55 | 5 |

Method 6: Column: Waters Xterra MS-C8, 50×4.6 mm, 3.5 μm; 1.3 ml/min; UV-Detection: 230 nm/254 nm; Eluent A: Water (0.1% Trifluoacetic acid)+10% Acetonitrile, Eluent B: Acetonitrile

| Gradient: | |
|---|---|
| Time (min.) | % Eluent B |
| 0.00 | 20 |
| 3.25 | 90 |
| 4.00 | 90 |
| 4.10 | 20 |
| 4.30 | 20 |

Method 7: Column: Waters Xterra MS-C8, 50×4.6 mm, 3.5 µm; 1.3 ml/min; UV-Detection: 230 nm/254 nm; Eluent A: Water (0.1% Trifluoacetic acid)+10% Acetonitrile, Eluent B: Acetonitrile

| Gradient: | |
|---|---|
| Time (min.) | % Eluent B |
| 0.00 | 0 |
| 3.25 | 90 |
| 4.00 | 90 |
| 4.10 | 0 |
| 4.30 | 0 |

Method 8: Column: Waters Simmetry Shield RP8, 150×4.6 mm, 5 µm; 0.85 ml/min; UV-Detection: 230 nm/254 nm; Eluent A: Water (0.1% Formic acid)+5% Acetonitrile, Eluent B: Acetonitrile+5% Water (0.1% Formic acid)

| Gradient: | |
|---|---|
| Time (min.) | % Eluent B |
| 0.00 | 30 |
| 1.50 | 50 |
| 8.50 | 100 |
| 13.00 | 100 |
| 14.00 | 30 |
| 15.00 | 30 |

Method 9: Column: Simmetry Shield RP8, 150×4.6 mm, 5 µm; 0.85 ml/min; UV-Detection: 254 nm; Eluent A: 90% Water+10% Acetonitrile (0.1% Formic acid), Eluent B: 90% Acetonitrile+10% Water (0.1% Formic acid)

| Gradient: | |
|---|---|
| Time (min.) | % Eluent B |
| 0.00 | 30 |
| 1.50 | 50 |
| 8.50 | 100 |
| 13.50 | 100 |
| 15.00 | 30 |

Method 10: Column: Simmetry Shield RP8, 150×4.6 mm, 5 µm; 0.85 ml/min; UV-Detection: 254 nm; Eluent A: 90% Water+10% Acetonitrile (0.1% Formic acid), Eluent B: 90% Acetonitrile+10% Water (0.1% Formic acid)

| Gradient: | |
|---|---|
| Time (min.) | % Eluent B |
| 0.00 | 30 |
| 1.50 | 50 |
| 8.50 | 100 |
| 17.50 | 100 |
| 19.00 | 30 |

Method 11: HPLC apparatus type: Waters Alliance 2695, Waters 2996 diode array etector; column: Varian Microsorb 100 C18, 30×4.6 mm, 3.0 µm; 3.5 ml/min; UV-detection: 210-380 nm; eluent A: water+0.13% TFA, eluent B: acetonitrile;

| Gradient: | |
|---|---|
| Time (min.) | % Eluent B |
| 0.00 | 5 |
| 0.18 | 5 |
| 2.00 | 98 |
| 3.00 | 98 |
| 3.1 | 5 |
| 3.3 | 5 |
| 3.5 | 5 |

Preparation of the Starting Compounds

Example I

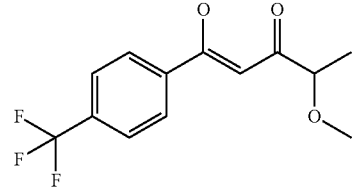 [SMILES: COC(C)C(=O)/C=C(\O)c1ccc(C(F)(F)F)cc1]

1-Hydroxy-4-methoxy-1-(4-trifluoromethyl-phenyl)-pent-1-en-3-one 10.14 g Potassium-tert.-butoxide and 225 mg 1,4,7,10,13,16-hexaoxacyclooctadecan are dissolved in 80 ml tetrahydrofurane. Then a solution of 10.0 g 1-(4-Trifluoromethyl-phenyl)-ethanone in 40 ml of tetrahydrofurane and a solution of 12.6 g racemic 2-Methoxy-propionic acid methyl ester in 40 ml of tetrahydrofurane are simultaneously added dropwise. After completion of addition the mixture is heated for four hours to reflux, cooled to 0° C. and hydrolyzed by dropwise addition of 50 ml of a 4 M solution of hydrochloric acid. The residue is partitioned between water and ethylacetate and the phases are separated. The aqueous phase is twice extracted with ethylacetate and the combined organic phases are washed with brine. After drying with magnesium sulphate the solvents are evaporated in vacuo. The residue is chromatographed on silica gel (cyclohexane/ethylacetate 95:5 to 85:15).

Yield: 10.0 g (69% of theory)
Mass spectrometry (ESI$^+$): m/z=275 [M+H]$^+$
HPLC (Method 3): Retention time=3.49 min.

Analogously to example I the following compounds are obtained:

(1) 4-Hydroxy-1-methoxy-4-(4-trifluoromethyl-phenyl)-but-3-en-2-one

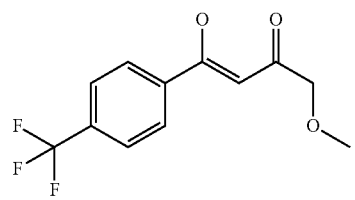 [SMILES: COCC(=O)/C=C(\O)c1ccc(C(F)(F)F)cc1]

Mass spectrometry (ESI⁻): m/z=259 [M−H]⁻
R$_f$-value: 0.30 (silica gel, petrole ether/ethylacetate 19:1)

(2) 4-Methoxy-1-(3-(trifluoromethyl)phenyl)pentane-1,3-dione

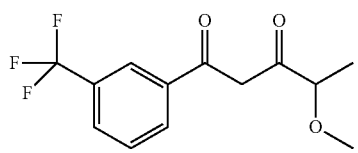 [SMILES: COC(C)C(=O)CC(=O)c1cccc(C(F)(F)F)c1]

Mass spectrometry (ESI⁻): m/z=275 [M−H]⁻

Example II

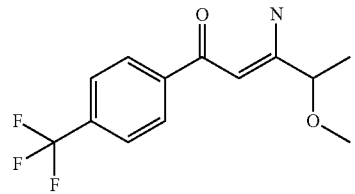 [SMILES: COC(C)/C(N)=C/C(=O)c1ccc(C(F)(F)F)cc1]

3-Amino-4-methoxy-1-(4-trifluoromethyl-phenyl)-pent-2-en-1-one 10.0 g 1-Hydroxy-4-methoxy-1-(4-trifluoromethyl-phenyl)-pent-1-en-3-one are dissolved in 100 ml ethanole. 4.7 g of Ammonium acetate are added and the mixture is heated for four hours to reflux. Then the solvent is evaporated in vacuo, the residue is partitioned between saturated aqueous sodium bicarbonate solution and dichloromethane. The phases are separated and the aqueous phase is twice extracted with dichloromethane. The combined organic phases are dried with magnesium sulphate, the solvents are evaporated in vacuo and the residue is chromatographed on silica gel (cyclohexane/ethylacetate 90:10 to 50:50).

Yield: 8.0 g (80% of theory)
Mass spectrometry (ESI⁺): m/z=274 [M+H]⁺
HPLC (Method 3): Retention time=2.98 min.

Analogously to example II the following compounds are obtained:

(1) 3-Amino-4-methoxy-1-(4-trifluoromethyl-phenyl)but-2-en-1-one

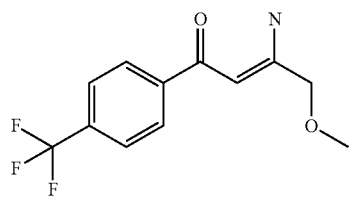 [SMILES: COC/C(N)=C/C(=O)c1ccc(C(F)(F)F)cc1]

Mass spectrometry (ESI⁺): m/z=260 [M+H]⁺

(2) 3-Amino-4-methoxy-1-(3-(trifluoromethyl)phenyl)pent-2-en-1-one

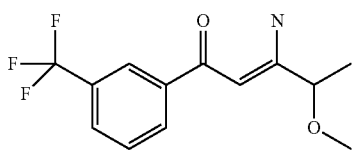 [SMILES: COC(C)/C(N)=C/C(=O)c1cccc(C(F)(F)F)c1]

Mass spectrometry (ESI⁺): m/z=274 [M+H]⁺

Example III

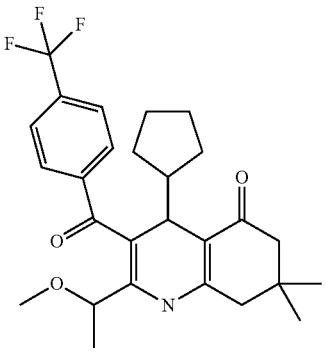 [SMILES: COC(C)C1=C(C(=O)c2ccc(C(F)(F)F)cc2)C(C2CCCC2)C2=C(CC(C)(C)CC2=O)N1]

4-Cyclopentyl-2-(1-methoxy-ethyl)-7,7-dimethyl-3-(4-trifluoromethyl-benzoyl)-4,6,7,8-tetrahydro-1H-quinolin-5-one 8.0 g 3-Amino-4-methoxy-1-(4-trifluoromethyl-phenyl)-pent-2-en-1-one are dissolved in 150 ml of diisopropylether, 2.2 ml trifluoroacetic acid and 4.1 g 5,5-dimethyl-cyclohexane-1,3-dione are successively added and the mixture is stirred for 10 minutes at room temperature. Then 3.75 ml cyclopentanecarbaldehyde are added and the mixture is heated for 15 hours to reflux at a dean-stark trap. After cooling to room temperature the solvents are evaporated in vacuo. The residue is chromatographed on silica gel (cyclohexane/ethylacetate 95:5 to 60:40). The product thus obtained is triturated with diisopropylether.

Yield: 4.7 g (34% of theory)
Mass spectrometry (ESI⁺): m/z=476 [M+H]⁺
HPLC (Method 3): Retention time=3.96 min.

Analogously to example III the following compounds are obtained:

(1) 4-Cyclopentyl-2-methoxymethyl-7,7-dimethyl-3-(4-trifluoromethyl-benzoyl)-4,6,7,8-tetrahydro-1H-quinolin-5-one

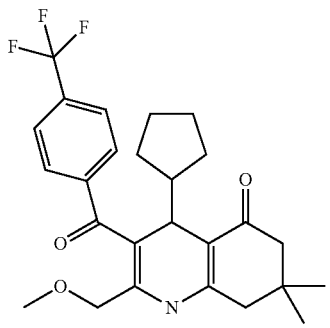 [SMILES: COCC1=C(C(=O)c2ccc(C(F)(F)F)cc2)C(C2CCCC2)C2=C(CC(C)(C)CC2=O)N1]

Mass spectrometry (ESI⁺): m/z=462 [M+H]⁺
HPLC (Method 2): Retention time=4.65 min.

(2) 4-Cyclohexyl-2-(1-methoxy-ethyl)-7,7-dimethyl-3-(4-trifluoromethyl-benzoyl)-4,6,7,8-tetrahydro-1H-quinolin-5-one

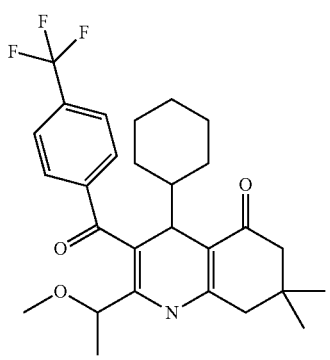 [SMILES: COC(C)C1=C(C(=O)c2ccc(C(F)(F)F)cc2)C(C2CCCCC2)C2=C(CC(C)(C)CC2=O)N1]

Mass spectrometry (ESI⁺): m/z=490 [M+H]⁺
HPLC (Method 6): Retention time=3.16 min.

(3) 2-(1-Methoxyethyl)-7,7-dimethyl-4-(tetrahydro-2H-pyran-4-yl)-3-(4-(trifluoromethyl)-benzoyl)-4,6,7,8-tetrahydroquinolin-5(1H)-one

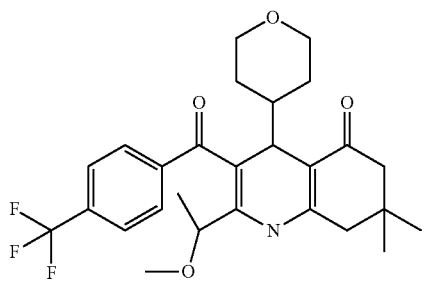 [SMILES: COC(C)C1=C(C(=O)c2ccc(C(F)(F)F)cc2)C(C2CCOCC2)C2=C(CC(C)(C)CC2=O)N1]

Mass spectrometry (ESI⁺): m/z=492 [M+H]⁺
$R_f$-value: 0.25 (silica gel, n-hexane/acetone 7:3)

(4) Benzyl-4-(2-(1-methoxyethyl)-7,7-dimethyl-5-oxo-3-(4-(trifluoromethyl)benzoyl)-1,4,5,6,7,8-hexahydroquinolin-4-yl)piperidine-1-carboxylate

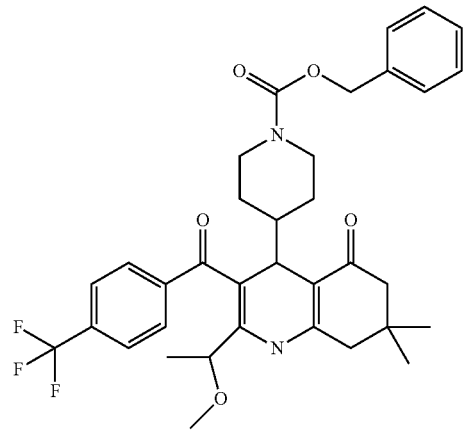 [SMILES: COC(C)C1=C(C(=O)c2ccc(C(F)(F)F)cc2)C(C2CCN(C(=O)OCc3ccccc3)CC2)C2=C(CC(C)(C)CC2=O)N1]

Mass spectrometry (ESI⁺): m/z=625 [M+H]⁺

(5) 4-Cyclopentyl-2-(1-methoxyethyl)-7,7-dimethyl-3-(3-(trifluoromethyl)benzoyl)-4,6,7,8-tetrahydroquinolin-5(1H)-one

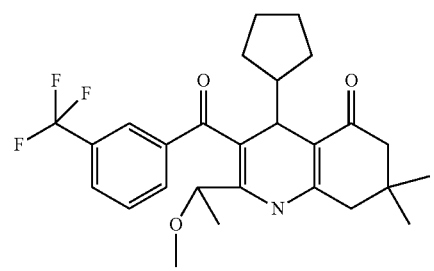 [SMILES: COC(C)C1=C(C(=O)c2cccc(C(F)(F)F)c2)C(C2CCCC2)C2=C(CC(C)(C)CC2=O)N1]

Mass spectrometry (ESI⁺): m/z=476 [M+H]⁺

(6) 4-Isopropyl-2-(1-methoxyethyl)-7,7-dimethyl-3-(4-(trifluoromethyl)benzoyl)-4,6,7,8-tetrahydroquinolin-5(1H)-one

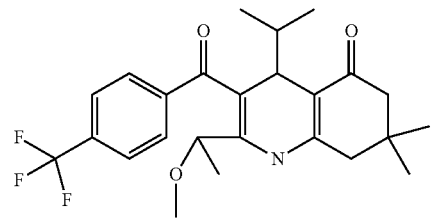 [SMILES: COC(C)C1=C(C(=O)c2ccc(C(F)(F)F)cc2)C(C(C)C)C2=C(CC(C)(C)CC2=O)N1]

Mass spectrometry (ESI⁺): m/z=450 [M+H]⁺
$R_f$-value: 0.14 (silica gel, n-hexane/acetone 4:1)

(7) 4-Cyclohexyl-2-(1-methoxy-ethyl)-7,7-dimethyl-5-oxo-1,4,5,6,7,8-hexahydro-quinoline-3-carboxylic acid ethyl ester

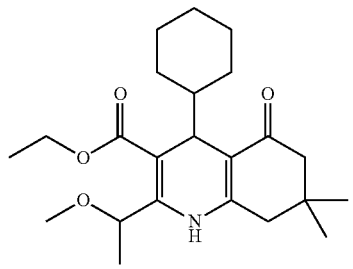 [SMILES: CCOC(=O)C1=C(C(C)OC)NC2=C(C(=O)CC(C)(C)C2)C1C1CCCCC1]

Mass spectrometry (ESI⁺): m/z=390 [M+H]⁺

Example IV

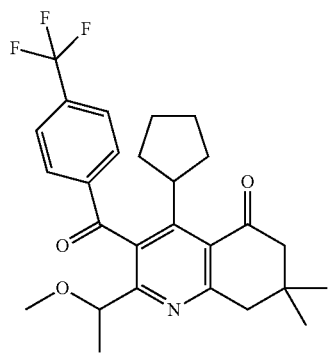 [SMILES: COC(C)c1nc2c(c(C3CCCC3)c1C(=O)c1ccc(C(F)(F)F)cc1)C(=O)CC(C)(C)C2]

4-Cyclopentyl-2-(1-methoxy-ethyl)-7,7-dimethyl-3-(4-trifluoromethyl-benzoyl)-7,8-dihydro-6H-quinolin-5-one 4.7 g 4-Cyclopentyl-2-(1-methoxy-ethyl)-7,7-dimethyl-3-(4-trifluoromethyl-benzoyl)-4,6,7,8-tetrahydro-1H-quinolin-5-one are dissolved in 100 ml dichloromethane, cooled to 0° C. and 2.5 g 2,3-dichloro-5,6-dicyano-p-benzoquinone are added portionwise. The temperature is raised during 3 hours to room temperature. Then the volume is reduced to approximately 60 ml by evaporation in vacuo, the mixture is filtered and the filter cake is washed 5 times with 50 ml of dichloromethane. The combined organic phases are evaporated in vacuo and the residue is chromatographed on silica gel (cyclohexane/ethylacetate 90:10 to 50:50). The product thus obtained is dissolved in cyclohexane/ethylacetate 70:30 and treated with charcoal. The mixture is filtered and the charcoal is washed 3 times with 100 ml cyclohexane/ethylacetate 70:30. The combined organic phases are evaporated in vacuo.

Yield: 3.6 g (76% of theory)
Mass spectrometry (ESI⁺): m/z=474 [M+H]⁺
HPLC (Method 3): Retention time=4.19 min.

Analogously to example IV the following compounds are obtained:

(1) 4-Cyclopentyl-2-methoxymethyl-7,7-dimethyl-3-(4-trifluoromethyl-benzoyl)-7,8-dihydro-6H-quinolin-5-one

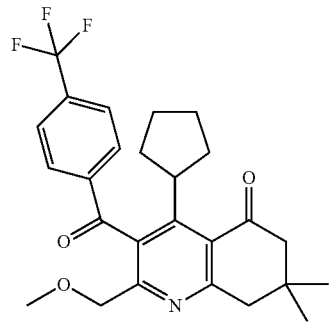 [SMILES: COCc1nc2c(c(C3CCCC3)c1C(=O)c1ccc(C(F)(F)F)cc1)C(=O)CC(C)(C)C2]

Mass spectrometry (ESI⁺): m/z=460 [M+H]⁺
R$_f$-value: 0.64 (silica gel, petrole ether/ethylacetate 4:1)

(2) 4-Cyclohexyl-2-(1-methoxy-ethyl)-7,7-dimethyl-3-(4-trifluoromethyl-benzoyl)-7,8-dihydro-6H-quinolin-5-one

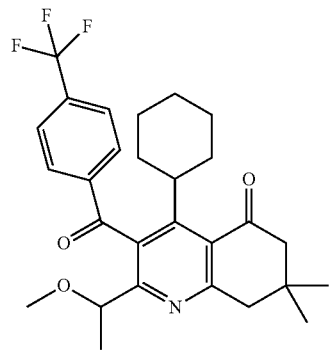 [SMILES: COC(C)c1nc2c(c(C3CCCCC3)c1C(=O)c1ccc(C(F)(F)F)cc1)C(=O)CC(C)(C)C2]

Mass spectrometry (ESI⁺): m/z=488 [M+H]⁺
HPLC (Method 7): Retention time=3.70 min.

(3) 4-(4-Fluorophenyl)-2-(1-methoxyethyl)-7,7-dimethyl-3-(4-(trifluoromethyl)benzoyl)-7,8-dihydroquinolin-5(6H)-one

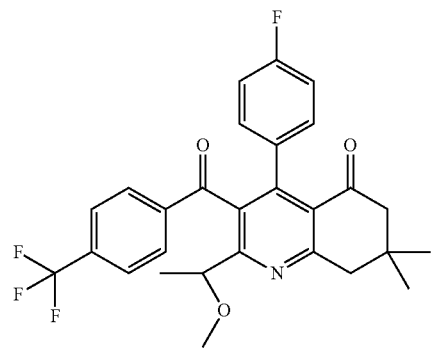 [SMILES: COC(C)c1nc2c(c(-c3ccc(F)cc3)c1C(=O)c1ccc(C(F)(F)F)cc1)C(=O)CC(C)(C)C2]

Mass spectrometry (ESI⁺): m/z=500 [M+H]⁺
HPLC (Method 9): Retention time=10.39 min.

(4) 2-(1-Methoxyethyl)-7,7-dimethyl-4-(tetrahydro-2H-pyran-4-yl)-3-(4-(trifluoromethyl)benzoyl)-7,8-dihydroquinolin-5(6H)-one

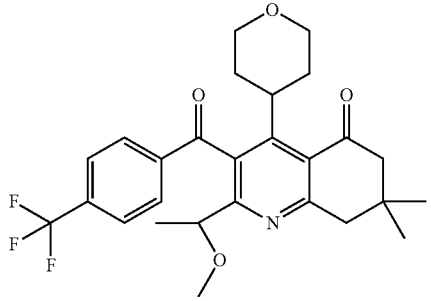 [SMILES: COC(C)c1nc2c(c(C3CCOCC3)c1C(=O)c1ccc(C(F)(F)F)cc1)C(=O)CC(C)(C)C2]

Mass spectrometry (ESI⁺): m/z=490 [M+H]⁺
HPLC (Method 9): Retention time=9.74 min.

(5) Benzyl-4-(2-(1-methoxyethyl)-7,7-dimethyl-5-oxo-3-(4-(trifluoromethyl)benzoyl)-5,6,7,8-tetrahydroquinolin-4-yl)piperidine-1-carboxylate

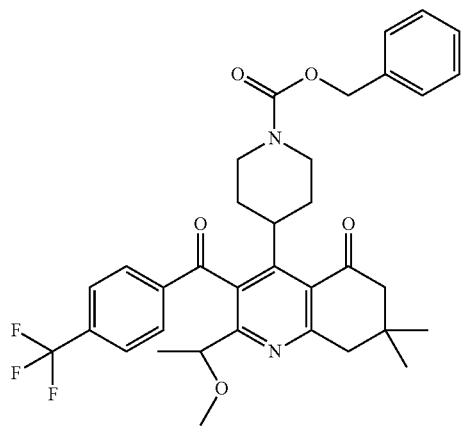 [SMILES: COC(C)c1nc2c(c(C3CCN(C(=O)OCc4ccccc4)CC3)c1C(=O)c1ccc(C(F)(F)F)cc1)C(=O)CC(C)(C)C2]

Mass spectrometry (ESI⁺): m/z=623 [M+H]⁺

(6) 4-Cyclopentyl-2-(1-methoxyethyl)-7,7-dimethyl-3-(3-(trifluoromethyl)benzoyl)-7,8-dihydroquinolin-5(6H)-one

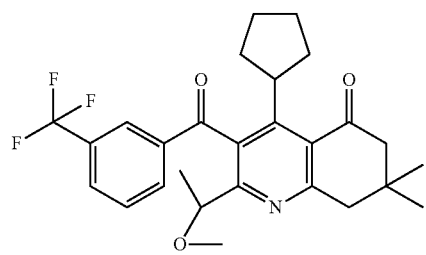 [SMILES: COC(C)c1nc2c(c(C3CCCC3)c1C(=O)c1cccc(C(F)(F)F)c1)C(=O)CC(C)(C)C2]

Mass spectrometry (ESI⁺): m/z=474 [M+H]⁺

(7) 4-Isopropyl-2-(1-methoxyethyl)-7,7-dimethyl-3-(4-(trifluoromethyl)benzoyl)-7,8-dihydroquinolin-5(6H)-one

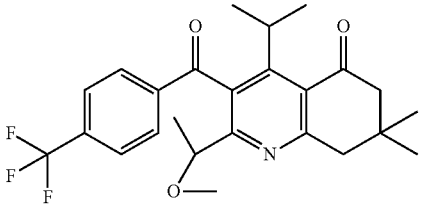 [SMILES: COC(C)c1nc2c(c(C(C)C)c1C(=O)c1ccc(C(F)(F)F)cc1)C(=O)CC(C)(C)C2]

Mass spectrometry (ESI⁺): m/z=450 [M+H]⁺

(8) 4-Cyclohexyl-2-(1-methoxy-ethyl)-7,7-dimethyl-5-oxo-5,6,7,8-tetrahydro-quinoline-3-carboxylic acid ethyl ester

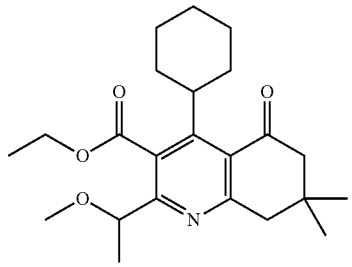 [SMILES: CCOC(=O)c1c(C(C)OC)nc2c(c1C1CCCCC1)C(=O)CC(C)(C)C2]

Mass spectrometry (ESI⁺): m/z=388 [M+H]⁺

Example V

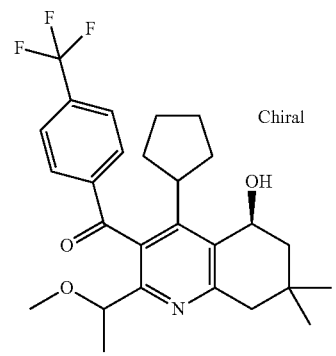 [SMILES: COC(C)c1nc2c(c(C3CCCC3)c1C(=O)c1ccc(C(F)(F)F)cc1)[C@@H](O)CC(C)(C)C2]

5-(S)-[4-Cyclopentyl-5-hydroxy-2-(1-methoxy-ethyl)-7,7-dimethyl-5,6,7,8-tetrahydro-quinolin-3-yl]-(4-trifluoromethyl-phenyl)-methanone (Diastereomer 1) and

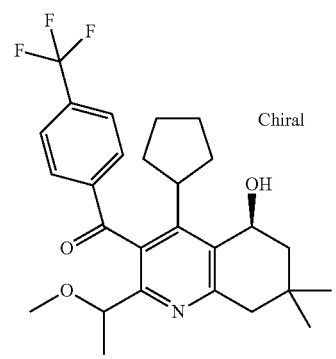 [SMILES: COC(C)c1nc2c(c(C3CCCC3)c1C(=O)c1ccc(C(F)(F)F)cc1)[C@@H](O)CC(C)(C)C2]

5-(S)-[4-Cyclopentyl-5-hydroxy-2-(1-methoxy-ethyl)-7,7-dimethyl-5,6,7,8-tetrahydro-quinolin-3-yl]-(4-trifluoromethyl-phenyl)-methanone (Diastereomer 2)

90 mg (1R,2S)-(+)-cis-1-Amino-2-indanol are dissolved in 200 ml tetrahydrofurane and to this solution are dropwise added 5.4 ml of a borane-diethylaniline-complex. After completion of gas evolution the solution is cooled to 0° C. and 3.6 g 4-Cyclopentyl-2-(1-methoxy-ethyl)-7,7-dimethyl-3-(4-trifluoromethyl-benzoyl)-7,8-dihydro-6H-quinolin-5-one in 50 ml tetrahydrofurane are added dropwise. The temperature is raised during 28 hours to room temperature, 20 ml methanol are added dropwise and the mixture is stirred for additional 10 minutes. The solvents are evaporated in vacuo and the residue is partitioned between water and ethylacetate. The aqueous phase is extracted twice with ethylacetate and the combined organic phases are washed with brine. After drying with magnesium sulphate the solvents are evaporated in vacuo and the residue is chromatographed on silica gel (cyclohexane/ethylacetate 95:5 to 75:25) giving partial separation of the diastereomers.

Diastereomer 1 (elutes first from silica gel column):
Yield: 850 mg (24% of theory)
and
Diastereomer 2 (elutes second from silica gel column):
Yield: 600 mg (17% of theory)
Diastereomer 1 and Diastereomer 2 give retention times of 5.06 and 5.16 min. by HPLC Method 5.

Analogously to example V the following compounds are obtained:

(1) 5-(S)-(4-Cyclopentyl-5-hydroxy-2-methoxymethyl-7,7-dimethyl-5,6,7,8-tetrahydro-quinolin-3-yl)-(4-trifluoromethyl-phenyl)-methanone

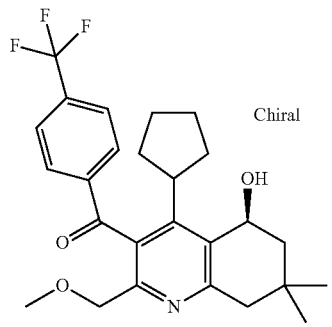 [SMILES: COCc1nc2c(c(C3CCCC3)c1C(=O)c1ccc(C(F)(F)F)cc1)[C@@H](O)CC(C)(C)C2]

Mass spectrometry (ESI$^+$): m/z=462 [M+H]$^+$
R$_f$-value: 0.42 (silica gel, petrole ether/ethylacetate 2:1)

(2) 5-(S)-[4-Cyclohexyl-5-hydroxy-2-(1-methoxy-ethyl)-7,7-dimethyl-5,6,7,8-tetrahydro-quinolin-3-yl]-(4-trifluoromethyl-phenyl)-methanone (Diastereomer 1)

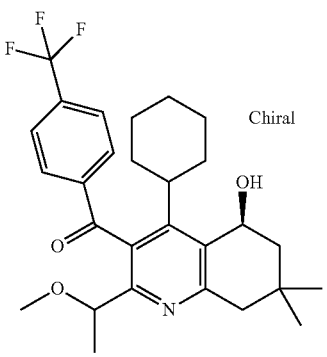 [SMILES: COC(C)c1nc2c(c(C3CCCCC3)c1C(=O)c1ccc(C(F)(F)F)cc1)[C@@H](O)CC(C)(C)C2]

and

P 5-(S)-[4-Cyclohexyl-5-hydroxy-2-(1-methoxy-ethyl)-7,7-dimethyl-5,6,7,8-tetrahydro-quinolin-3-yl]-(4-trifluoromethyl-phenyl)-methanone (Diastereomer 2)

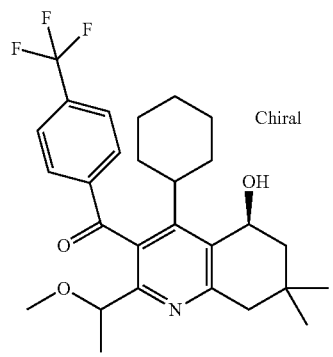 [SMILES: COC(C)c1nc2c(c(C3CCCCC3)c1C(=O)c1ccc(C(F)(F)F)cc1)[C@@H](O)CC(C)(C)C2]

The compounds are obtained starting from 4-Cyclohexyl-2-(1-methoxy-ethyl)-7,7-dimethyl-3-(4-trifluoromethyl-benzoyl)-7,8-dihydro-6H-quinolin-5-one (example IV (2))

The compounds are obtained as a mixture of diastereomers which is used directly in the next step (example VI (3)).

Mass spectrometry (ESI$^+$): m/z=490 [M+H]$^+$

HPLC (Method 7): Retention time=3.70 min.

(3) ((5S)-4-(4-Fluorophenyl)-5-hydroxy-2-(1-methoxyethyl)-7,7-dimethyl-5,6,7,8-tetrahydroquinolin-3-yl)-(4-(trifluoromethyl)phenyl)methanone (Diastereomer 1)

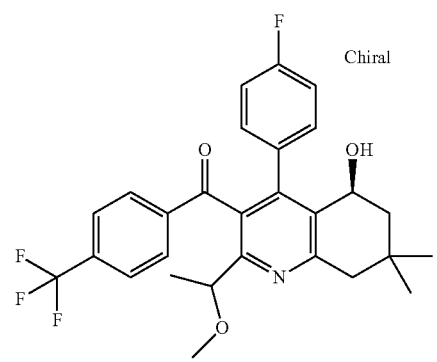 [SMILES: COC(C)c1nc2c(c(-c3ccc(F)cc3)c1C(=O)c1ccc(C(F)(F)F)cc1)[C@@H](O)CC(C)(C)C2]

Mass spectrometry (ESI$^+$): m/z=502 [M+H]$^+$
HPLC (Method 9): Retention time=9.41 min.

and ((5S)-4-(4-Fluorophenyl)-5-hydroxy-2-(1-methoxyethyl)-7,7-dimethyl-5,6,7,8-tetrahydroquinolin-3-yl)-(4-(trifluoromethyl)phenyl)methanone (Diastereomer 2)

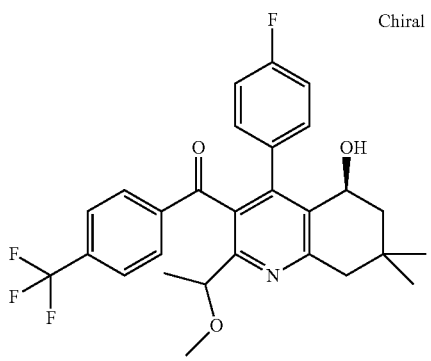 [SMILES: COC(C)c1nc2c(c(-c3ccc(F)cc3)c1C(=O)c1ccc(C(F)(F)F)cc1)[C@@H](O)CC(C)(C)C2]

Mass spectrometry (ESI⁺): m/z=502 [M+H]⁺

HPLC (Method 9): Retention time=9.59 min.

The compounds are obtained starting from 4-(4-Fluorophenyl)-2-(1-methoxyethyl)-7,7-dimethyl-3-(4-(trifluoromethyl)benzoyl)-7,8-dihydroquinolin-5(6H)-one (example IV (3)) The compounds are obtained as a mixture of diastereomers which is used directly in the next step (example VI (4)).

(4) ((5S)-5-Hydroxy-2-(1-methoxyethyl)-7,7-dimethyl-4-(tetrahydro-2H-pyran-4-yl)-5,6,7,8-tetrahydroquinolin-3-yl)-(4-(trifluoromethyl)phenyl)methanone

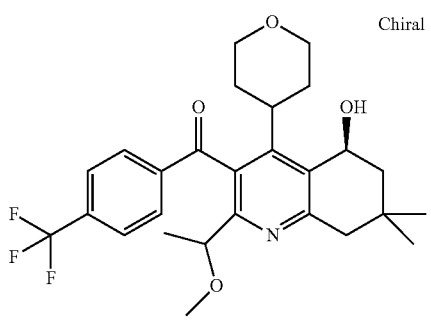 [SMILES: COC(C)c1nc2c(c(C3CCOCC3)c1C(=O)c1ccc(C(F)(F)F)cc1)[C@@H](O)CC(C)(C)C2]

Mass spectrometry (ESI⁺): m/z=492 [M+H]⁺

(5) Benzyl-4-((5S)-5-hydroxy-2-(1-methoxyethyl)-7,7-dimethyl-3-(4-(trifluoromethyl)benzoyl)-5,6,7,8-tetrahydroquinolin-4-yl)piperidine-1-carboxylate

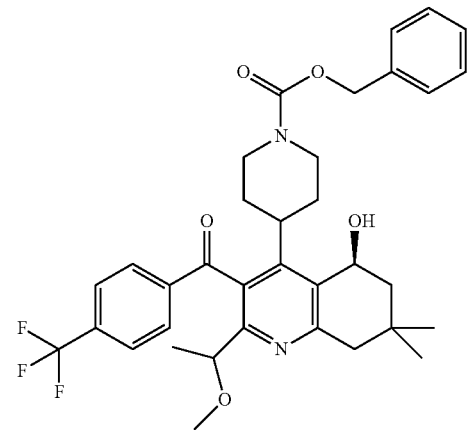 [SMILES: COC(C)c1nc2c(c(C3CCN(C(=O)OCc4ccccc4)CC3)c1C(=O)c1ccc(C(F)(F)F)cc1)[C@@H](O)CC(C)(C)C2]

Mass spectrometry (ESI⁺): m/z=625 [M+H]⁺

(6) ((5S)-4-Cyclopentyl-5-hydroxy-2-(1-methoxyethyl)-7,7-dimethyl-5,6,7,8-tetrahydroquinolin-3-yl)-(3-(trifluoromethyl)phenyl)methanone (Mixture of Diastereomer 1 and Diastereomer 2

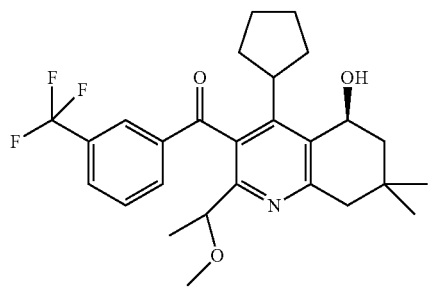 [SMILES: COC(C)c1nc2c(c(C3CCCC3)c1C(=O)c1cccc(C(F)(F)F)c1)[C@@H](O)CC(C)(C)C2]

Mass spectrometry (ESI⁺): m/z=476 [M+H]⁺

The compounds are obtained starting from 4-Cyclopentyl-2-(1-methoxyethyl)-7,7-dimethyl-3-(3-(trifluoromethyl)benzoyl)-7,8-dihydroquinolin-5(6H)-one (example IV (6)). The compounds are obtained as a mixture of diastereomers which is used directly in the next step (example VI (7)).

Diastereomer 1 and Diastereomer 2 give retention times of 10.16 and 10.26 min. by HPLC Method 9.

(7) ((5S)-5-Hydroxy-4-isopropyl-2-(1-methoxy-ethyl)-7,7-dimethyl-5,6,7,8-tetrahydroquinolin-3-yl)-(4-(trifluoromethyl)phenyl)methanone

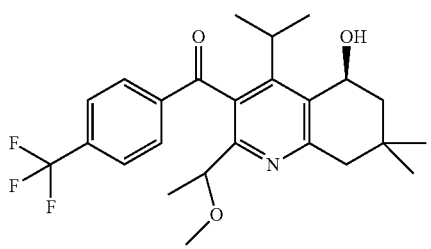 [SMILES: COC(C)c1nc2c(c(C(C)C)c1C(=O)c1ccc(C(F)(F)F)cc1)[C@@H](O)CC(C)(C)C2]

Mass spectrometry (ESI⁺): m/z=448 [M+H]⁺
$R_f$-value: 0.26 (silica gel, n-hexane/ethylacetate 4:1)

Example VI 5-(S)-[5-(tert-Butyl-dimethyl-silanyloxy)-4-cyclopentyl-2-(1-methoxy-ethyl)-7,7-dimethyl-5,6,7,8-tetrahydro-quinolin-3-yl]-(4-trifluoromethyl-phenyl)-methanone (Diastereomer 1)

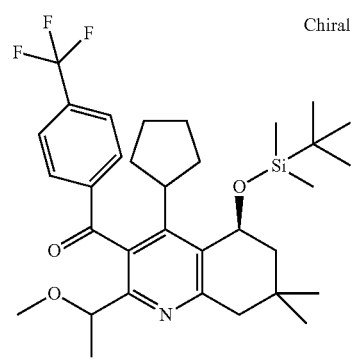 [SMILES: COC(C)c1nc2c(c(C3CCCC3)c1C(=O)c1ccc(C(F)(F)F)cc1)[C@@H](O[Si](C)(C)C(C)(C)C)CC(C)(C)C2]

840 mg 5-(S)-[4-Cyclopentyl-5-hydroxy-2-(1-methoxy-ethyl)-7,7-dimethyl-5,6,7,8-tetrahydro-quinolin-3-yl]-(4-trifluoromethyl-phenyl)-methanone (Diastereomer 1) are dissolved in 20 ml toluene, 823 µl 2,6-lutidine are added and the solution is cooled to −18° C. 811 µl Trifluoromethanesulfonic acid-tert.-butyldimethylsilylester are added dropwise and the mixture is stirred for further 20 minutes at −18° C. Then it is warmed to 0° C. and stirred for 1 hour whereafter the mixture is partitioned between saturated aqueous ammonium chloride solution and ethylacetate. The aqueous phase is twice extracted with ethylacetate and the combined organic phases are washed with brine. After drying with magnesium sulphate the solvents are evaporated in vacuo and the residue is chromatographed on silica gel (cyclohexane/ethylacetate 95:5 to 80:20).

Yield: 897 mg (86% of theory)
Mass spectrometry (ESI⁺): m/z=590 [M+H]⁺

Analogously to example VI the following compounds are obtained:

(1) 5-(S)-[5-(tert-Butyl-dimethyl-silanyloxy)-4-cyclopentyl-2-(1-methoxy-ethyl)-7,7-dimethyl-5,6,7,8-tetrahydro-quinolin-3-yl]-(4-trifluoromethyl-phenyl)-methanone (Diastereomer 2)

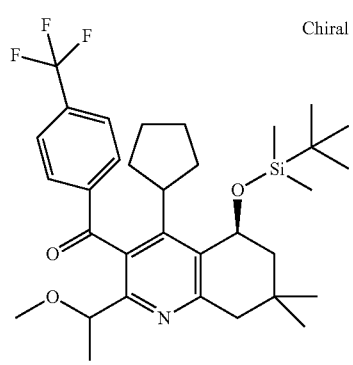 [SMILES: COC(C)c1nc2c(c(C3CCCC3)c1C(=O)c1ccc(C(F)(F)F)cc1)[C@@H](O[Si](C)(C)C(C)(C)C)CC(C)(C)C2]

Obtained starting from 5-(S)-[4-Cyclopentyl-5-hydroxy-2-(1-methoxy-ethyl)-7,7-dimethyl-5,6,7,8-tetrahydro-quinolin-3-yl]-(4-trifluoromethyl-phenyl)-methanone (Diastereomer 2)

Mass spectrometry (ESI⁺): m/z=590 [M+H]⁺

(2) 5-(S)-[5-(tert-Butyl-dimethyl-silanyloxy)-4-cyclopentyl-2-methoxymethyl-7,7-dimethyl-5,6,7,8-tetrahydro-quinolin-3-yl]-(4-trifluoromethyl-phenyl)-methanone

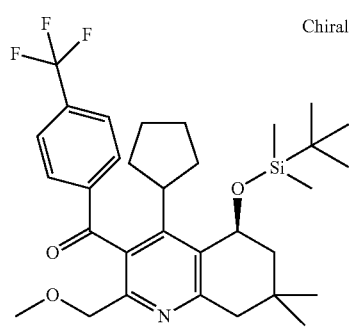 [SMILES: COCc1nc2c(c(C3CCCC3)c1C(=O)c1ccc(C(F)(F)F)cc1)[C@@H](O[Si](C)(C)C(C)(C)C)CC(C)(C)C2]

Mass spectrometry (ESI⁺): m/z=576 [M+H]⁺
$R_f$-value: 0.84 (silica gel, petrole ether/ethylacetate 4:1)

117

(3) 5-(S)-[5-(tert-Butyl-dimethyl-silanyloxy)-4-cyclohexyl-2-(1-methoxy-ethyl)-7,7-dimethyl-5,6,7,8-tetrahydro-quinolin-3-yl]-(4-trifluoromethyl-phenyl)-methanone (Diastereomer 1)

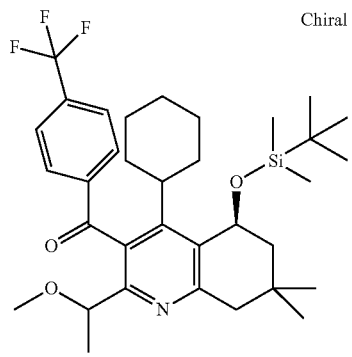 [SMILES: COC(C)c1nc2c(c(C3CCCCC3)c1C(=O)c1ccc(C(F)(F)F)cc1)[C@@H](O[Si](C)(C)C(C)(C)C)CC(C)(C)C2]

and 5-(S)-[5-(tert-Butyl-dimethyl-silanyloxy)-4-cyclohexyl-2-(1-methoxy-ethyl)-7,7-dimethyl-5,6,7,8-tetrahydro-quinolin-3-yl]-(4-trifluoromethyl-phenyl)-methanone (Diastereomer 2)

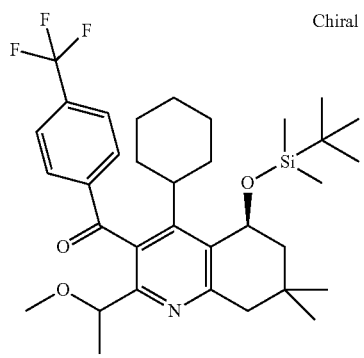 [SMILES: COC(C)c1nc2c(c(C3CCCCC3)c1C(=O)c1ccc(C(F)(F)F)cc1)[C@@H](O[Si](C)(C)C(C)(C)C)CC(C)(C)C2]

The compounds are obtained starting from 5-(S)-[4-Cyclohexyl-5-hydroxy-2-(1-methoxy-ethyl)-7,7-dimethyl-5,6,7,8-tetrahydro-quinolin-3-yl]-(4-trifluoromethyl-phenyl)-methanone (example V (2)).

The compounds are obtained as a mixture of diastereomers which is directly used in the next step (example VII (3)).

Rf value: 0.74 (hexane/ethylacetate 7:3)

Mass spectrometry (ESI+): m/z=604 [M+H]+

Diastereomer 1 and Diastereomer 2 give retention times of 9.91 and 10.11 min. by HPLC Method 8.

118

(4) ((5S)-5-(tert-Butyldimethylsilyloxy)-4-(4-fluorophenyl)-2-(1-methoxyethyl)-7,7-dimethyl-5,6,7,8-tetrahydroquinolin-3-yl)-(4-(trifluoromethyl)phenyl)methanone (Diastereomer 1)

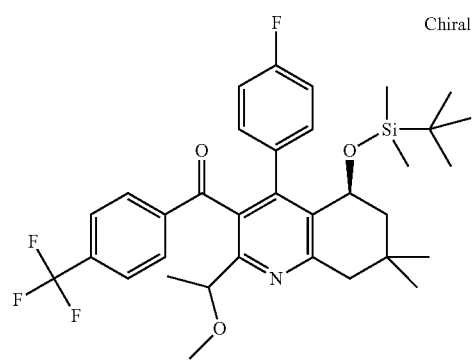 [SMILES: COC(C)c1nc2c(c(-c3ccc(F)cc3)c1C(=O)c1ccc(C(F)(F)F)cc1)[C@@H](O[Si](C)(C)C(C)(C)C)CC(C)(C)C2]

and ((5S)-5-(tert-Butyldimethylsilyloxy)-4-(4-fluorophenyl)-2-(1-methoxyethyl)-7,7-dimethyl-5,6,7,8-tetrahydroquinolin-3-yl)-(4-(trifluoromethyl)phenyl)methanone (Diastereomer 2)

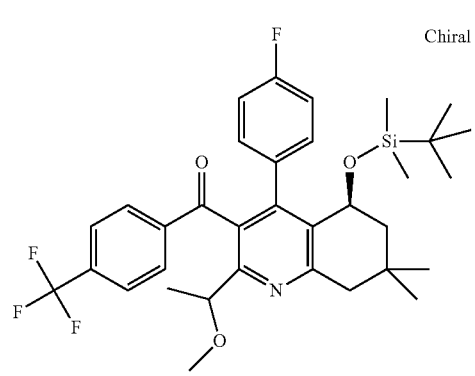 [SMILES: COC(C)c1nc2c(c(-c3ccc(F)cc3)c1C(=O)c1ccc(C(F)(F)F)cc1)[C@@H](O[Si](C)(C)C(C)(C)C)CC(C)(C)C2]

The compounds are obtained starting from ((5S)-4-(4-Fluorophenyl)-5-hydroxy-2-(1-methoxyethyl)-7,7-dimethyl-5,6,7,8-tetrahydroquinolin-3-yl)-(4-(trifluoromethyl)phenyl)methanone (example V (3)). The compounds are obtained as pure diastereomers. Diastereomer 2 is used in example VII (4) and Diastereomer 2 is used in example VII (8).

Mass spectrometry (ESI+): m/z=616 [M+H]+

Diastereomer 1 and Diastereomer 2 give retention times of 14.84 and 14.02 min. by HPLC Method 10.

(5) ((5S)-5-(tert-Butyldimethylsilyloxy)-2-(1-methoxyethyl)-7,7-dimethyl-4-(tetrahydro-2H-pyran-4-yl)-5,6,7,8-tetrahydroquinolin-3-yl)-(4-(trifluoromethyl)phenyl)methanone

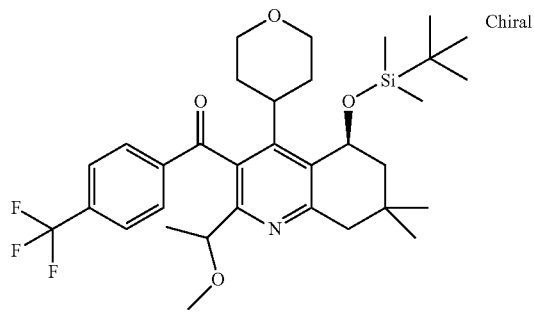 [SMILES: COC(C)c1nc2c(c(C3CCOCC3)c1C(=O)c1ccc(C(F)(F)F)cc1)[C@@H](O[Si](C)(C)C(C)(C)C)CC(C)(C)C2]

Mass spectrometry (ESI$^+$): m/z=606 [M+H]$^+$
R$_f$-value: 0.6 (silica gel, n-hexane/ethylacetate 8:2)

(6) Benzyl 4-((5S)-5-(tert-butyldimethylsilyloxy)-2-(1-methoxyethyl)-7,7-dimethyl-3-(4-(trifluoromethyl)benzoyl)-5,6,7,8-tetrahydroquinolin-4-yl)piperidine-1-carboxylate

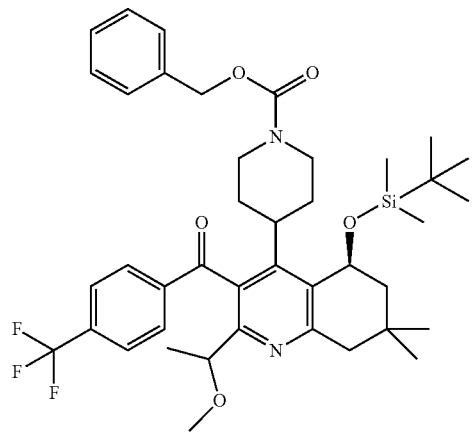 [SMILES: COC(C)c1nc2c(c(C3CCN(C(=O)OCc4ccccc4)CC3)c1C(=O)c1ccc(C(F)(F)F)cc1)[C@@H](O[Si](C)(C)C(C)(C)C)CC(C)(C)C2]

Mass spectrometry (ESI$^+$): m/z=739 [M+H]$^+$
HPLC (Method 10): Retention time=14.22 min.

(7) ((5S)-5-(tert-butyldimethylsilyloxy)-4-cyclopentyl-2-(1-methoxyethyl)-7,7-dimethyl-5,6,7,8-tetrahydroquinolin-3-yl)-(3-(trifluoromethyl)phenyl)methanone

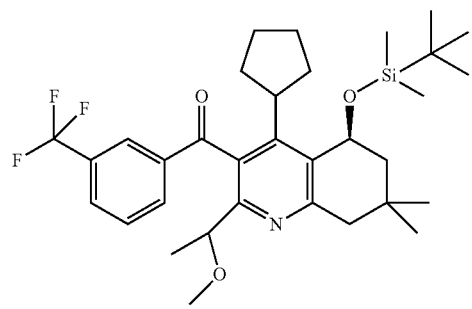 [SMILES: COC(C)c1nc2c(c(C3CCCC3)c1C(=O)c1cccc(C(F)(F)F)c1)[C@@H](O[Si](C)(C)C(C)(C)C)CC(C)(C)C2]

Mass spectrometry (ESI$^+$): m/z=590 [M+H]$^+$
HPLC (Method 9): Retention time=15.5 min.

(8) ((5S)-5-(tert-Butyldimethylsilyloxy)-4-isopropyl-2-(1-methoxyethyl)-7,7-dimethyl-5,6,7,8-tetrahydroquinolin-3-yl)-(4-(trifluoromethyl)phenyl)methanone (Diastereomer 1)

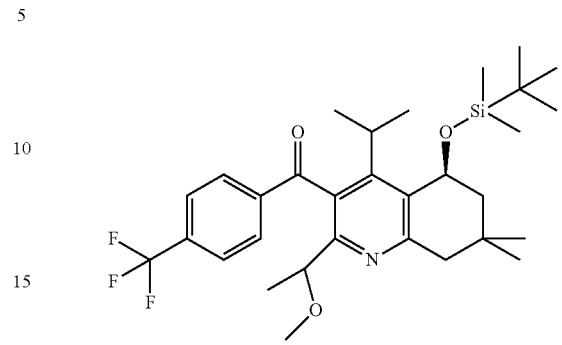

and ((5S)-5-(tert-Butyldimethylsilyloxy)-4-isopropyl-2-(1-methoxyethyl)-7,7-dimethyl-5,6,7,8-tetrahydroquinolin-3-yl)-(4-(trifluoromethyl)phenyl)methanone (Diastereomer 2)

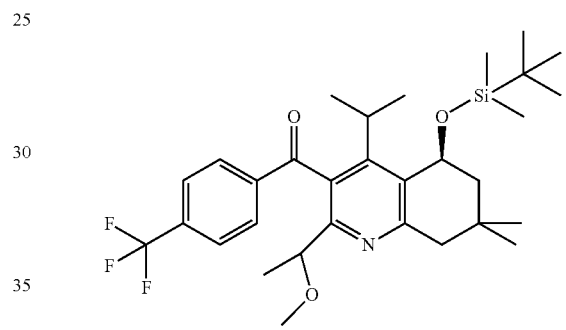

The compounds are obtained starting from ((5S)-5-Hydroxy-4-isopropyl-2-(1-methoxyethyl)-7,7-dimethyl-5,6,7,8-tetrahydroquinolin-3-yl)-(4-(trifluoromethyl)phenyl)methanone. (example V (7)). The compounds are obtained as a mixture of diastereomers which is directly used in the next step (example VII (7)).

Rf value: 0.12 (cyclohexane/ethylacetate 95:5) Diastereomer 1
Rf value: 0.14 (cyclohexane/ethylacetate 95:5) Diastereomer 2
Mass spectrometry (ESI$^+$): m/z=564 [M+H]$^+$
Diastereomer 1 and Diastereomer 2 give retention times of 14.95 and 14.72 min. by HPLC Method 10.

Example VII

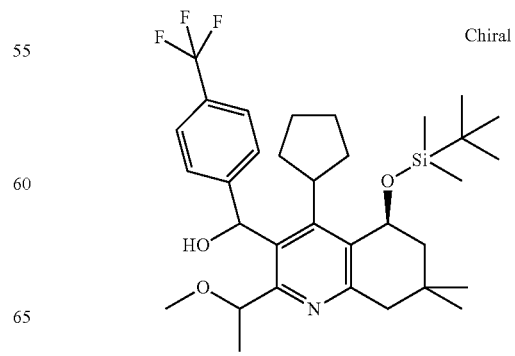

5-(S)-[5-(tert-Butyl-dimethyl-silanyloxy)-4-cyclo-
pentyl-2-(1-methoxy-ethyl)-7,7-dimethyl-5,6,7,8-
tetrahydro-quinolin-3-yl]-trifluoromethyl-phenyl)-
methanol (Diastereomer 1)

and

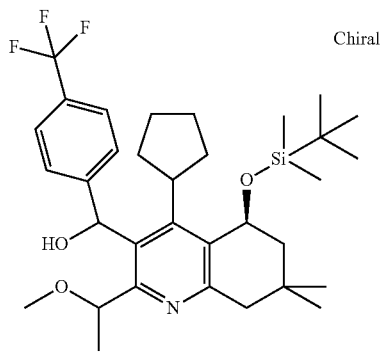 [SMILES: COC(C)c1nc2c(c(C3CCCC3)c1C(O)c1ccc(C(F)(F)F)cc1)[C@@H](O[Si](C)(C)C(C)(C)C)CC(C)(C)C2]

5-(S)-[5-(tert-Butyl-dimethyl-silanyloxy)-4-cyclo-
pentyl-2-(1-methoxy-ethyl)-7,7-dimethyl-5,6,7,8-
tetrahydro-quinolin-3-yl]-4-trifluoromethyl-phenyl)-
methanol (Diastereomer 2)

690 mg 5-(S)-[5-(tert-Butyl-dimethyl-silanyloxy)-4-cyclopentyl-2-(1-methoxy-ethyl)-7,7-dimethyl-5,6,7,8-tetrahydro-quinolin-3-yl]-(4-trifluoromethyl-phenyl)-methanone (Diastereomer 1) are dissolved in 15 ml tetrahydrofurane, cooled to 0° C. and thereto 1.76 ml of a 1 M solution of lithium aluminium hydride in tetrahydrofurane is added dropwise. The temperature is raised to room temperature during 12 hours and then 24 ml of a saturated solution of sodium potassium tartrate are added dropwise. The aqueous phase is twice extracted with ethylacetate and the combined organic phases are washed with brine. After drying with magnesium sulphate the solvents are evaporated in vacuo and the residue is chromatographed on silica gel (cyclohexane/ethylacetate 95:5 to 75:25).

5-(S)-[5-(tert-Butyl-dimethyl-silanyloxy)-4-cyclopentyl-2-(1-methoxy-ethyl)-7,7-dimethyl-5,6,7,8-tetrahydro-quinolin-3-yl]-(4-trifluoromethyl-phenyl)-methanol (Diastereomer 1) (elutes first from silica gel column):

Yield: 420 mg (61% of theory)

Mass spectrometry (ESI$^+$): m/z=592 [M+H]$^+$ and 5-(S)-[5-(tert-Butyl-dimethyl-silanyloxy)-4-cyclopentyl-2-(1-methoxy-ethyl)-7,7-dimethyl-5,6,7,8-tetrahydro-quinolin-3-yl]-(4-trifluoromethyl-phenyl)-methanol (Diastereomer 2) (elutes second from silica gel column):

Yield: 242 mg (35% of theory)

Mass spectrometry (ESI$^+$): m/z=592 [M+H]$^+$

Diastereomer 1 and Diastereomer 2 give retention times of 1.91 and 2.00 min. by HPLC Method 4.

Analogously to example VII the following compounds are obtained:

(1) 5-(S)-[5-(tert-Butyl-dimethyl-silanyloxy)-4-cyclopentyl-2-(1-methoxy-ethyl)-7,7-dimethyl-5,6,7,8-tetrahydro-quinolin-3-yl]-(4-trifluoromethyl-phenyl)-methanol (Diastereomer 3)

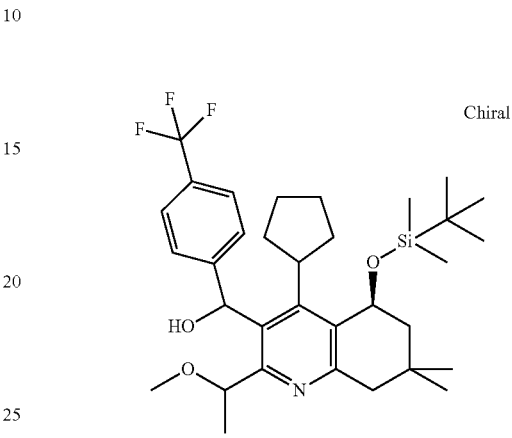

Mass spectrometry (ESI$^+$): m/z=592 [M+H]$^+$ and 5-(S)-[5-(tert-Butyl-dimethyl-silanyloxy)-4-cyclopentyl-2-(1-methoxy-ethyl)-7,7-dimethyl-5,6,7,8-tetrahydro-quinolin-3-yl]-(4-trifluoromethyl-phenyl)-methanol (Diastereomer 4)

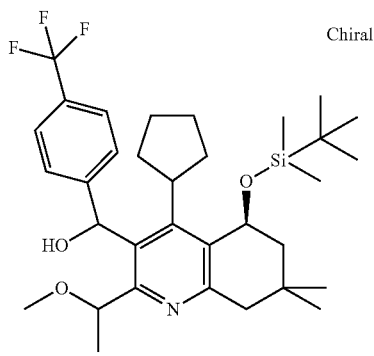 [SMILES: COC(C)c1nc2c(c(C3CCCC3)c1C(O)c1ccc(C(F)(F)F)cc1)[C@@H](O[Si](C)(C)C(C)(C)C)CC(C)(C)C2]

Mass spectrometry (ESI$^+$): m/z=592 [M+H]$^+$

The compounds are obtained starting from 5-(S)-[5-(tert-Butyl-dimethyl-silanyloxy)-4-cyclopentyl-2-(1-methoxy-ethyl)-7,7-dimethyl-5,6,7,8-tetrahydro-quinolin-3-yl]-(4-trifluoromethyl-phenyl)-methanone (Diastereomer 2). The diastereomers are separated by silica gel chromatography (cyclohexane/ethylacetate 95:5 to 75:25).

Diastereomer 3 and Diastereomer 4 give retention times of 1.91 and 1.96 min. by HPLC Method 4.

(2) 5-(S)-[5-(tert-Butyl-dimethyl-silanyloxy)-4-cyclopentyl-2-methoxymethyl-7,7-dimethyl-5,6,7,8-tetrahydro-quinolin-3-yl]-(4-trifluoromethyl-phenyl)-methanol

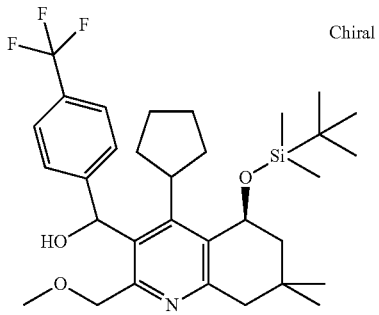 [SMILES: COCc1nc2c(c(C3CCCC3)c1C(O)c1ccc(C(F)(F)F)cc1)[C@@H](O[Si](C)(C)C(C)(C)C)CC(C)(C)C2]

The compound is obtained as a mixture of diastereomers and directly submitted to the next step (example IX).
The diastereomers give $R_f$-values of 0.64 and 0.68 (silica gel, petrole ether/ethylacetate 2:1)

(3) 5-(S)-[5-(tert-Butyl-dimethyl-silanyloxy)-4-cyclohexyl-2-(1-methoxy-ethyl)-7,7-dimethyl-5,6,7,8-tetrahydro-quinolin-3-yl]-(4-trifluoromethyl-phenyl)-methanol (Diastereomer 1)

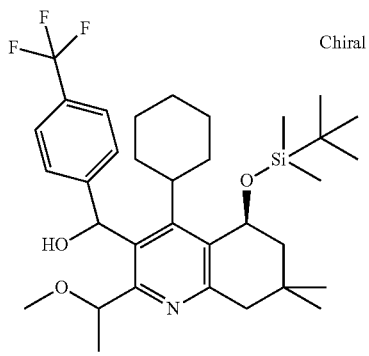 [SMILES: COC(C)c1nc2c(c(C3CCCCC3)c1C(O)c1ccc(C(F)(F)F)cc1)[C@@H](O[Si](C)(C)C(C)(C)C)CC(C)(C)C2]

and 5-(S)-[5-(tert-Butyl-dimethyl-silanyloxy)-4-cyclohexyl-2-(1-methoxy-ethyl)-7,7-dimethyl-5,6,7,8-tetrahydro-quinolin-3-yl]-(4-trifluoromethyl-phenyl)-methanol (Diastereomers 2, 3 and 4)

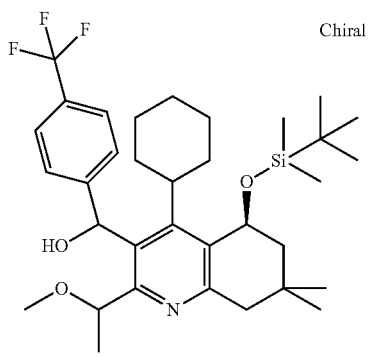 [SMILES: COC(C)c1nc2c(c(C3CCCCC3)c1C(O)c1ccc(C(F)(F)F)cc1)[C@@H](O[Si](C)(C)C(C)(C)C)CC(C)(C)C2]

The compounds are obtained starting from 5-(S)-[5-(tert-Butyl-dimethyl-silanyloxy)-4-cyclohexyl-2-(1-methoxy-ethyl)-7,7-dimethyl-5,6,7,8-tetrahydro-quinolin-3-yl]-(4-trifluoromethyl-phenyl)-methanone (example VI (3)).

Diastereomer 1 is obtained as a single diastereomer by silica gel chromatography (hexane/ethylacetate 10:1).
Mass spectrometry (ESI+): m/z=606 [M+H]+
$R_f$-value: 0.42 (silica gel, hexane/ethylacetate 7:3)
Diastereomers 2, 3 and 4 are obtained as a mixture.
Mass spectrometry (ESI+): m/z=606 [M+H]+
$R_f$-value: 0.53 (silica gel, hexane/ethylacetate 7:3)
Diastereomer 1, Diastereomer 2, Diastereomer 3 and Diastereomer 4 give retention times of 8.26, 8.42, 8.85 and 9.04 by HPLC Method 8.

(4) ((5S)-5-(tert-Butyldimethylsilyloxy)-4-(4-fluorophenyl)-2-(1-methoxyethyl)-7,7-dimethyl-5,6,7,8-tetrahydroquinolin-3-yl)-(4-(trifluoromethyl)phenyl)methanol (Diastereomer 1)

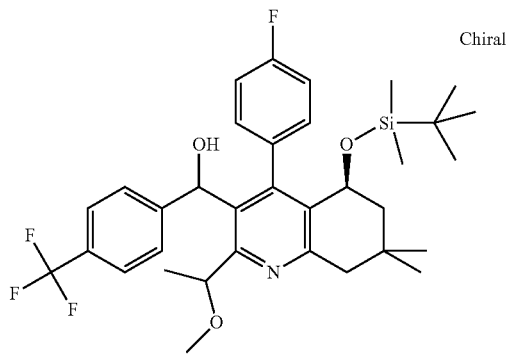 [SMILES: COC(C)c1nc2c(c(-c3ccc(F)cc3)c1C(O)c1ccc(C(F)(F)F)cc1)[C@@H](O[Si](C)(C)C(C)(C)C)CC(C)(C)C2]

and ((5S)-5-(tert-Butyldimethylsilyloxy)-4-(4-fluorophenyl)-2-(1-methoxyethyl)-7,7-dimethyl-5,6,7,8-tetrahydroquinolin-3-yl)-(4-(trifluoromethyl)phenyl)methanol (Diastereomer 2)

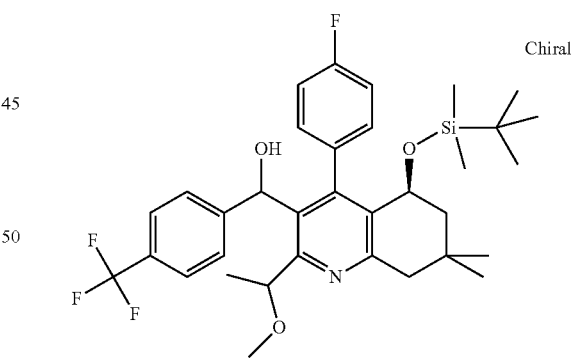

The compounds are obtained from ((5S)-5-(tert-Butyldimethylsilyloxy)-4-(4-fluorophenyl)-2-(1-methoxyethyl)-7,7-dimethyl-5,6,7,8-tetrahydroquinolin-3-yl)(4-(trifluoromethyl)-phenyl)methanone (Diastereomer 2) (example VI (4)).
Diastereomer 1 is obtained as a single diastereomer by silica gel chromatography (hexane/ethylacetate 9:1).
Mass spectrometry (ESI+): m/z=618 [M+H]+
HPLC (Method 9): Retention time=10.48 min.
Diastereomer 2 is obtained as a single diastereomer.
Mass spectrometry (ESI+): m/z=618 [M+H]+
HPLC (Method 9): Retention time=10.44 min.
Diastereomer 2 is used in example IX (2).

(5) (1R)-((5S)-5-(tert-butyldimethylsilyloxy)-2-(1-methoxyethyl)-7,7-dimethyl-4-(tetrahydro-2H-pyran-4-yl)-5,6,7,8-tetrahydroquinolin-3-yl)-(4-(trifluoromethyl)phenyl)methanol (Diastereomer 1)

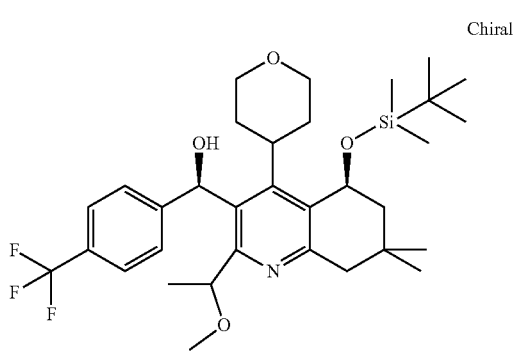 [SMILES: COC(C)c1nc2c(c(C3CCOCC3)c1[C@H](O)c1ccc(C(F)(F)F)cc1)[C@@H](O[Si](C)(C)C(C)(C)C)CC(C)(C)C2]

and (1R)-((5S)-5-(tert-butyldimethylsilyloxy)-2-(1-methoxyethyl)-7,7-dimethyl-4-(tetrahydro-2H-pyran-4-yl)-5,6,7,8-tetrahydroquinolin-3-yl)-(4-(trifluoromethyl)phenyl)methanol (Diastereomer 1, 2, 3)

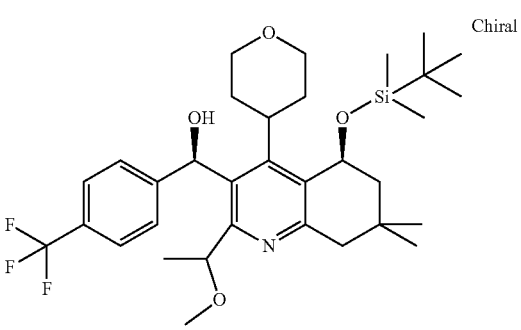 [SMILES: COC(C)c1nc2c(c(C3CCOCC3)c1[C@H](O)c1ccc(C(F)(F)F)cc1)[C@@H](O[Si](C)(C)C(C)(C)C)CC(C)(C)C2]

The compounds are obtained starting from ((5S)-5-(tert-Butyldimethylsilyloxy)-2-(1-methoxyethyl)-7,7-dimethyl-4-(tetrahydro-2H-pyran-4-yl)-5,6,7,8-tetrahydroquinolin-3-yl)-(4-(trifluoromethyl)phenyl)methanone (example VI (5)).

Diastereomer 1 is obtained as a single diastereomer by silica gel chromatography (hexane/ethylacetate 4:1).

Mass spectrometry (ESI⁺): m/z=608 [M+H]⁺

R$_f$-value: 0.18 (silica gel, n-hexane/ethylacetate 4:1)

HPLC (Method 10): Retention time=7.3 min.

Diastereomer 1 is used in example IX (3).

Diastereomer 1, 2, 3 are obtained as a mixture.

Mass spectrometry (ESI⁺): m/z=608 [M+H]⁺

Diastereomer 1, Diastereomer 2, Diastereomer 3 and Diastereomer 4 give retention times of 7.3, 7.9 and 8.3 by HPLC Method 10.

(6) ((5S)-5-(tert-Butyldimethylsilyloxy)-4-cyclopentyl-2-(1-methoxyethyl)-7,7-dimethyl-5,6,7,8-tetrahydroquinolin-3-yl)-(3-(trifluoromethyl)phenyl)methanol

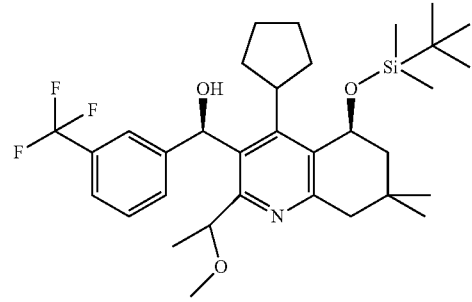 [SMILES: COC(C)c1nc2c(c(C3CCCC3)c1[C@H](O)c1cccc(C(F)(F)F)c1)[C@@H](O[Si](C)(C)C(C)(C)C)CC(C)(C)C2]

Mass spectrometry (ESI⁺): m/z=592 [M+H]⁺

Rf value: 0.21 (hexane/ethylacetate 4:1)

(7) ((5S)-5-(tert-Butyldimethylsilyloxy)-4-isopropyl-2-(1-methoxyethyl)-7,7-dimethyl-5,6,7,8-tetrahydroquinolin-3-yl)-(4-(trifluoromethyl)phenyl)methanol (Diastereomer 1)

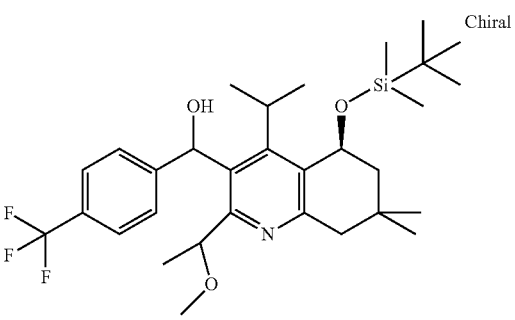 [SMILES: COC(C)c1nc2c(c(C(C)C)c1C(O)c1ccc(C(F)(F)F)cc1)[C@@H](O[Si](C)(C)C(C)(C)C)CC(C)(C)C2]

and ((5S)-5-(tert-Butyldimethylsilyloxy)-4-isopropyl-2-(1-methoxyethyl)-7,7-dimethyl-5,6,7,8-tetrahydroquinolin-3-yl)-(4-(trifluoromethyl)phenyl)methanol (Diastereomer 2)

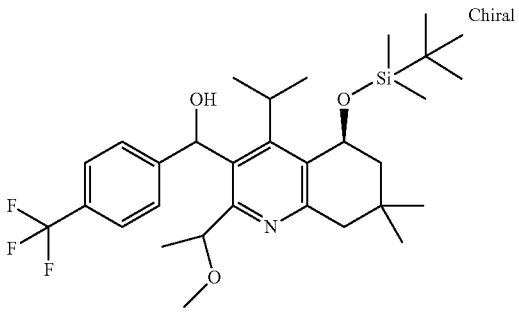 [SMILES: COC(C)c1nc2c(c(C(C)C)c1C(O)c1ccc(C(F)(F)F)cc1)[C@@H](O[Si](C)(C)C(C)(C)C)CC(C)(C)C2]

and ((5S)-5-(tert-Butyldimethylsilyloxy)-4-isopropyl-2-(1-methoxyethyl)-7,7-dimethyl-5,6,7,8-tetrahydroquinolin-3-yl)-(4-(trifluoromethyl)phenyl)methanol (Diastereomer 3)

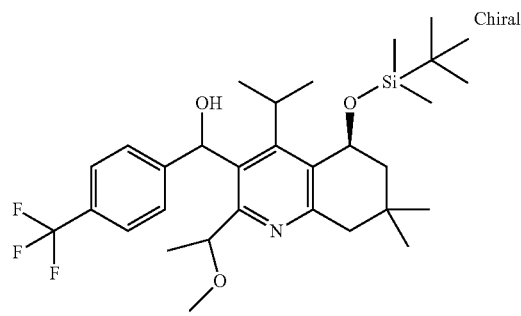 [SMILES: COC(C)c1nc2c(c(C(C)C)c1C(O)c1ccc(C(F)(F)F)cc1)[C@@H](O[Si](C)(C)C(C)(C)C)CC(C)(C)C2]

and ((5S)-5-(tert-Butyldimethylsilyloxy)-4-isopropyl-2-(1-methoxyethyl)-7,7-dimethyl-5,6,7,8-tetrahydroquinolin-3-yl)-(4-(trifluoromethyl)phenyl)methanol (Diastereomer 4)

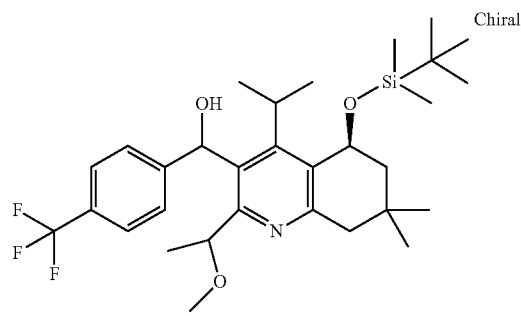 [SMILES: COC(C)c1nc2c(c(C(C)C)c1C(O)c1ccc(C(F)(F)F)cc1)[C@@H](O[Si](C)(C)C(C)(C)C)CC(C)(C)C2]

The compounds are obtained starting from ((5S)-5-(tert-Butyldimethylsilyloxy)-4-isopropyl-2-(1-methoxyethyl)-7,7-dimethyl-5,6,7,8-tetrahydroquinolin-3-yl)-(4-(trifluoromethyl)phenyl)methanone (example VI (8)).

Diastereomer 1 is obtained as a single diastereomer by HPLC

Mass spectrometry (ESI⁺): m/z=566 [M+H]⁺

Diastereomer 2 is obtained as a single diastereomer by HPLC.

Mass spectrometry (ESI⁺): m/z=566 [M+H]⁺

Diastereomer 3 is obtained as a single diastereomer by HPLC.

Mass spectrometry (ESI⁺): m/z=566 [M+H]⁺

Diastereomer 4 is obtained as a single diastereomer by HPLC.

Mass spectrometry (ESI⁺): m/z=566 [M+H]⁺

Diastereomer 2 is used in the next step (example IX (6)).

Diastereomer 1, Diastereomer 2, Diastereomer 3 and Diastereomer 4 give retention times of 7.11, 7.97, 6.87 and 7.59 by HPLC Method 10

(8) ((5S)-5-(tert-Butyldimethylsilyloxy)-4-(4-fluorophenyl)-2-(1-methoxyethyl)-7,7-dimethyl-5,6,7,8-tetrahydroquinolin-3-yl)-(4-(trifluoromethyl)phenyl)methanol (Diastereomer 1)

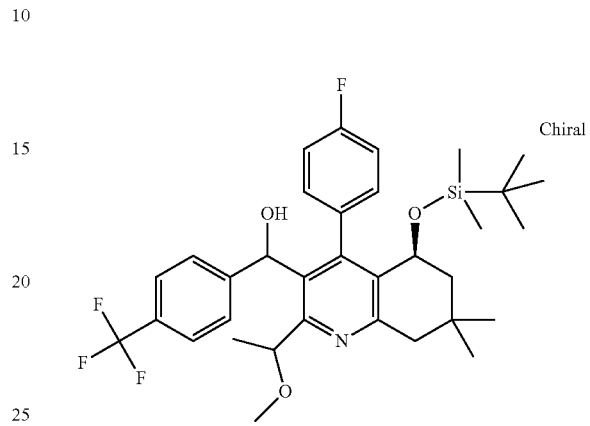

and ((5S)-5-(tert-Butyldimethylsilyloxy)-4-(4-fluorophenyl)-2-(1-methoxyethyl)-7,7-dimethyl-5,6,7,8-tetrahydroquinolin-3-yl)-(4-(trifluoromethyl)phenyl)methanol (Diastereomer 2)

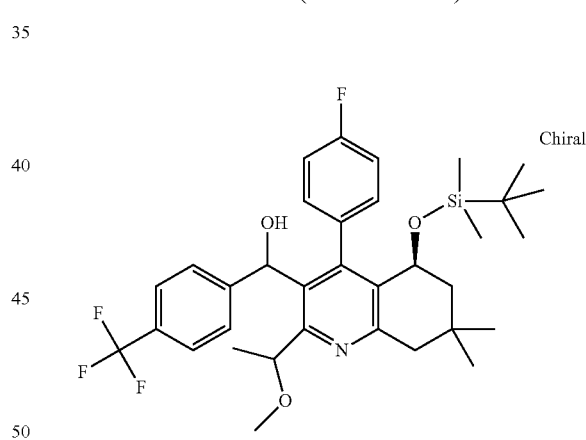

The compounds are obtained from ((5S)-5-(tert-butyldimethylsilyloxy)-4-(4-fluorophenyl)-2-(1-methoxyethyl)-7,7-dimethyl-5,6,7,8-tetrahydroquinolin-3-yl)-(4-(trifluoromethyl)phenyl)methanone (Diastereomer 1) (example VI (4)).

Diastereomer 1 is obtained as a single diastereomer by HPLC.

Mass spectrometry (ESI⁺): m/z=618 [M+H]⁺

HPLC (Method 9): Retention time=10.32 min.

Diastereomer 2 is obtained as a single diastereomer by HPLC.

Mass spectrometry (ESI⁺): m/z=618 [M+H]⁺

HPLC (Method 9): Retention time=11.06 min.

Diastereomer 2 is used in example IX (8).

Example VIII

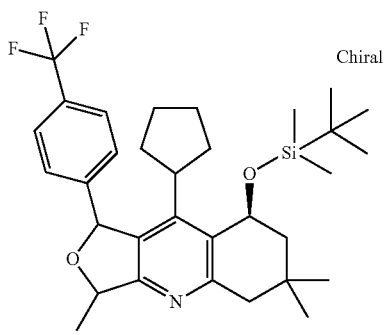 [SMILES: CC1OC(c2ccc(C(F)(F)F)cc2)c2c1nc1c(c2C2CCCC2)[C@@H](O[Si](C)(C)C(C)(C)C)CC(C)(C)C1]

8-(S)-8-(tert-Butyl-dimethyl-silanyloxy)-9-cyclopentyl-3,6,6-trimethyl-1-(4-trifluoromethyl-phenyl)-1,3,5,6,7,8-hexahydro-furo[3,4-b]quinoline (Diastereomer 1)

and

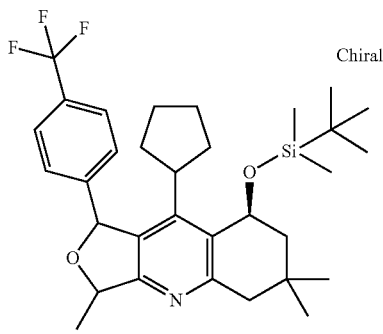 [SMILES: CC1OC(c2ccc(C(F)(F)F)cc2)c2c1nc1c(c2C2CCCC2)[C@@H](O[Si](C)(C)C(C)(C)C)CC(C)(C)C1]

8-(S)-8-(tert-Butyl-dimethyl-silanyloxy)-9-cyclopentyl-3,6,6-trimethyl-1-(4-trifluoromethyl-phenyl)-1,3,5,6,7,8-hexahydro-furo[3,4-b]quinoline (Diastereomer 2)

390 mg 5-(S)-[5-(tert-Butyl-dimethyl-silanyloxy)-4-cyclopentyl-2-(1-methoxy-ethyl)-7,7-dimethyl-5,6,7,8-tetrahydro-quinolin-3-yl]-(4-trifluoromethyl-phenyl)-methanol (Diastereomer 1) are dissolved in 10 ml of dichloromethane, cooled to −10° C. and 131 µl diethylaminosulfurtrichloride (DAST) are added hereto dropwise. After stirring for 3 hours the temperature is raised to 0° C. and then the reaction mixture is partitioned between saturated sodium bicarbonate and ethylacetate. The aqueous phase is extracted for 3 times with ethylacetate and the combined organic phases are washed with brine. After drying with magnesium sulphate the solvents are evaporated in vacuo and the residue is chromatographed on silica gel (cyclohexane/ethylacetate 95:5 to 70:30).

8-(S)-8-(tert-Butyl-dimethyl-silanyloxy)-9-cyclopentyl-3,6,6-trimethyl-1-(4-trifluoromethyl-phenyl)-1,3,5,6,7,8-hexahydro-furo[3,4-b]quinoline (Diastereomer 1) (elutes as second product from silica gel column)
Yield: 82 mg (21% of theory)
Mass spectrometry (ESI$^+$): m/z=560 [M+H]$^+$
HPLC (Method 4): Retention time=3.07 min.

and
8-(S)-8-(tert-Butyl-dimethyl-silanyloxy)-9-cyclopentyl-3,6,6-trimethyl-1-(4-trifluoromethyl-phenyl)-1,3,5,6,7,8-hexahydro-furo[3,4-b]quinoline (Diastereomer 2) (elutes as third product from silica gel column)
Yield: 211 mg (54% of theory)
Mass spectrometry (ESI$^+$): m/z=560 [M+H]$^+$
HPLC (Method 4): Retention time=3.04 min.

As a third product in this reaction the following compound is obtained:
5-(S)-5-(tert-Butyl-dimethyl-silanyloxy)-4-cyclopentyl-3-[fluoro-(4-trifluoromethyl-phenyl)-methyl]-2-(1-methoxy-ethyl)-7,7-dimethyl-5,6,7,8-tetrahydro-quinoline (elutes as first product from silica gel column)
Yield: 62 mg (16% of theory)
Mass spectrometry (ESI$^+$): m/z=594 [M+H]$^+$
HPLC (Method 4): Retention time=2.98 min.

Analogously to example VIII the following compounds are obtained:

(1) 8-(S)-8-(tert-Butyl-dimethyl-silanyloxy)-9-cyclopentyl-3,6,6-trimethyl-1-(4-trifluoromethyl-phenyl)-1,3,5,6,7,8-hexahydro-furo[3,4-b]quinoline (Diastereomer 3)

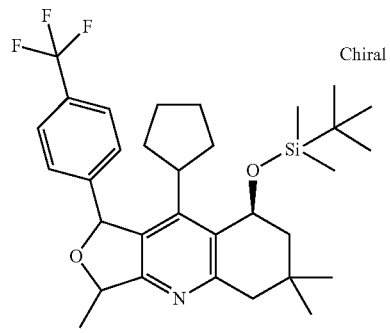 [SMILES: CC1OC(c2ccc(C(F)(F)F)cc2)c2c1nc1c(c2C2CCCC2)[C@@H](O[Si](C)(C)C(C)(C)C)CC(C)(C)C1]

and 8-(S)-8-(tert-Butyl-dimethyl-silanyloxy)-9-cyclopentyl-3,6,6-trimethyl-1-(4-trifluoromethyl-phenyl)-1,3,5,6,7,8-hexahydro-furo[3,4-b]quinoline (Diastereomer 4)

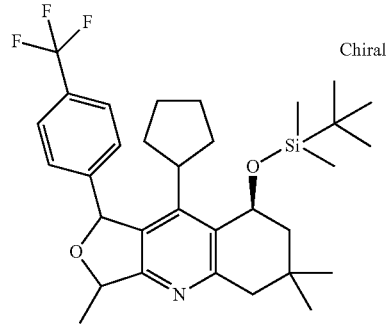 [SMILES: CC1OC(c2ccc(C(F)(F)F)cc2)c2c1nc1c(c2C2CCCC2)[C@@H](O[Si](C)(C)C(C)(C)C)CC(C)(C)C1]

The compounds are obtained starting from with 5-(S)-[5-(tert-Butyl-dimethyl-silanyloxy)-4-cyclopentyl-2-(1-methoxy-ethyl)-7,7-dimethyl-5,6,7,8-tetrahydro-quinolin-3-yl]-(4-trifluoromethyl-phenyl)-methanol (Diastereomer 3) as a mixture of diastereomers. The mixture is directly submitted to the next step (example 1 (2)).

Example IX

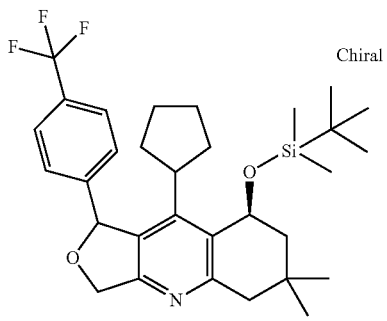 [SMILES: CC1(C)Cc2nc3c(c(C4CCCC4)c2[C@@H](O[Si](C)(C)C(C)(C)C)C1)C(c1ccc(C(F)(F)F)cc1)OC3]

8-(S)-8-(tert-Butyl-dimethyl-silanyloxy)-9-cyclopentyl-6,6-dimethyl-1-(4-trifluoromethyl-phenyl)-1,3,5,6,7,8-hexahydro-furo[3,4-b]quinoline 125 mg 5-(S)-[5-(tert-Butyl-dimethyl-silanyloxy)-4-cyclopentyl-2-methoxymethyl-7,7-dimethyl-5,6,7,8-tetrahydro-quinolin-3-yl]-(4-trifluoromethyl-phenyl)-methanol (example VII (2)) are dissolved in 5 ml tetrahydrofurane and cool to −50° C. Then 500 mg tetrabutylammonium iodide are added. Thereafter 100 µl diethylaminosulfurtrichloride (DAST) are added dropwise, the temperature is raised during 6 hours to 0° C. and then the mixture is stirred for 12 hours at room temperature. After cooling to 0° C. further 300 µl diethylaminosulfurtrichloride are added dropwise and the reaction is stirred for 2 hours while raising the temperature to room temperature. Then the mixture is diluted with ethylacetate and the organic phase is washed successively with 1 M hydrochloric acid, 1 M aqueous sodium hydroxide and brine. After drying with magnesium sulphate the solvents are evaporated in vacuo and the residue is chromatographed on silica gel (cyclohexane/ethylacetate 95:5 to 60:40). The product is thus obtained as a mixture of diastereomers and directly submitted to the next step (example 1 (3)).

Yield: 90 mg (76% of theory)
Mass spectrometry (ESI$^+$): m/z=546 [M+H]$^+$
HPLC (Method 3): Retention time=4.98 min.

Analogously to example IX the following compounds are obtained:

(1) 8-(S)-8-(tert-Butyl-dimethyl-silanyloxy)-9-cyclohexyl-3,6,6-trimethyl-1-(4-trifluoromethyl-phenyl)-1,3,5,6,7,8-hexahydro-furo[3,4-b]quinoline (Diastereomer 1)

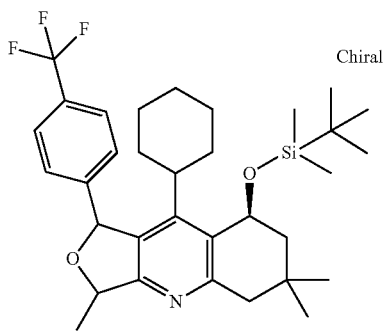 [SMILES: CC1OC(c2ccc(C(F)(F)F)cc2)c2c1nc1c(c2C2CCCCC2)[C@@H](O[Si](C)(C)C(C)(C)C)CC(C)(C)C1]

The compound is obtained from 5-(S)-[5-(tert-Butyl-dimethyl-silanyloxy)-4-cyclohexyl-2-(1-methoxy-ethyl)-7,7-dimethyl-5,6,7,8-tetrahydro-quinolin-3-yl]-(4-trifluoromethyl-phenyl)-methanol (Diastereomer 1) (example VII (3)).
Mass spectrometry (ESI$^+$): m/z=574 [M+H]$^+$
HPLC (Method 8): Retention time=11.07 min.

(2) (8S)-8-(tert-Butyldimethylsilyloxy)-9-(4-fluorophenyl)-3,6,6-trimethyl-1-(4-(trifluoromethyl)phenyl)-1,3,5,6,7,8-hexahydrofuro[3,4-b]quinoline

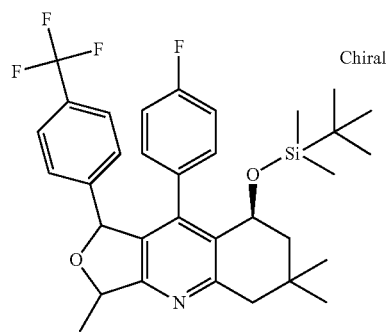 [SMILES: CC1OC(c2ccc(C(F)(F)F)cc2)c2c1nc1c(c2-c2ccc(F)cc2)[C@@H](O[Si](C)(C)C(C)(C)C)CC(C)(C)C1]

The compound is obtained starting from ((5S)-5-(tert-Butyldimethylsilyloxy)-4-(4-fluorophenyl)-2-(1-methoxyethyl)-7,7-dimethyl-5,6,7,8-tetrahydroquinolin-3-yl)-(4-(trifluoromethyl)phenyl)methanol (Diastereomer 2) (example VII(4)).
Mass spectrometry (ESI$^+$): m/z=586 [M+H]$^+$ (3) (8S)-8-(tert-Butyldimethylsilyloxy)-3,6,6-trimethyl-9-(tetrahydro-2H-pyran-4-yl)-1-(4-(trifluoromethyl)phenyl)-1,3,5,6,7,8-hexahydrofuro[3,4-b]quinoline

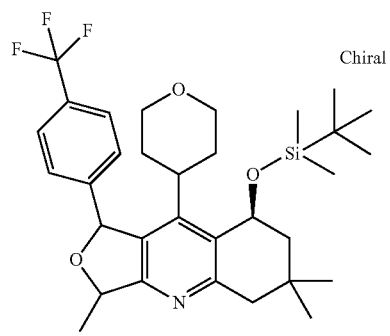 [SMILES: CC1OC(c2ccc(C(F)(F)F)cc2)c2c1nc1c(c2C2CCOCC2)[C@@H](O[Si](C)(C)C(C)(C)C)CC(C)(C)C1]

Mass spectrometry (ESI$^+$): m/z=576 [M+H]$^+$ (4) Benzyl 4-((8S)-8-(tert-butyldimethylsilyloxy)-3,6,6-trimethyl-1-(4-(trifluoromethyl)phenyl)-1,3,5,6,7,8-hexahydrofuro[3,4-b]quinolin-9-yl)piperidine-1-carboxylate (Diastereomer 1 and 2)

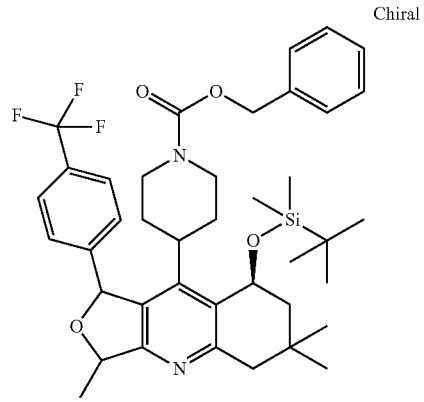 [SMILES: CC1OC(c2ccc(C(F)(F)F)cc2)c2c1nc1c(c2C2CCN(C(=O)OCc3ccccc3)CC2)[C@@H](O[Si](C)(C)C(C)(C)C)CC(C)(C)C1]

Diastereomer 1 and 2 are obtained as a mixture.
Mass spectrometry (ESI$^+$): m/z=709 [M+H]$^+$ Diastereomer 1 and Diastereomer 2 give retention times of 13.78 and 13.87 by HPLC Method 10.

(5) Benzyl 4-((8S)-8-(tert-butyldimethylsilyloxy)-3,6,6-trimethyl-1-(4-(trifluoromethyl)phenyl)-1,3,5,6,7,8-hexahydrofuro[3,4-b]quinolin-9-yl)piperidine-1-carboxylate (Diastereomer 1)

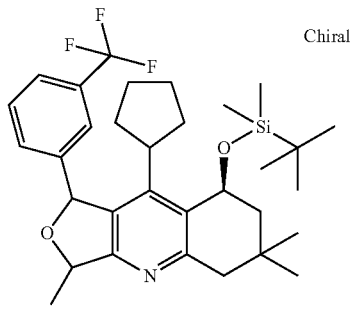 [SMILES: CC1OC(c2cccc(C(F)(F)F)c2)c2c1nc1c(c2C2CCCC2)[C@@H](O[Si](C)(C)C(C)(C)C)CC(C)(C)C1]

Mass spectrometry (ESI+): m/z=560 [M+H]+
and

Benzyl 4-((8S)-8-(tert-butyldimethylsilyloxy)-3,6,6-trimethyl-1-(4-(trifluoromethyl)phenyl)-1,3,5,6,7,8-hexahydrofuro[3,4-b]quinolin-9-yl)piperidine-1-carboxylate (Diastereomer 2)

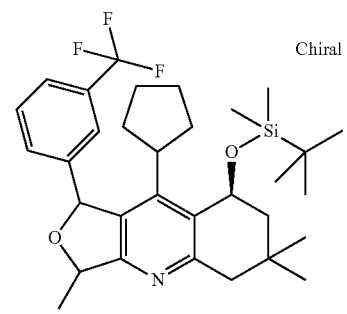 [SMILES: CC1OC(c2cccc(C(F)(F)F)c2)c2c1nc1c(c2C2CCCC2)[C@@H](O[Si](C)(C)C(C)(C)C)CC(C)(C)C1]

Mass spectrometry (ESI+): m/z=560 [M+H]+

(6) (8S)-8-(tert-Butyldimethylsilyloxy)-9-isopropyl-3,6,6-trimethyl-1-(4-(trifluoromethyl)phenyl)-1,3,5,6,7,8-hexahydrofuro[3,4-b]quinoline

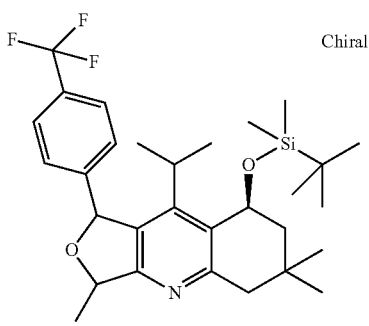 [SMILES: CC(C)c1c2c(nc3c1[C@@H](O[Si](C)(C)C(C)(C)C)CC(C)(C)C3)C(C)OC2c1ccc(C(F)(F)F)cc1]

The compound is obtained from ((5S)-5-(tert-Butyldimethylsilyloxy)-4-isopropyl-2-(1-methoxyethyl)-7,7-dimethyl-5,6,7,8-tetrahydroquinolin-3-yl)(4-(trifluoromethyl)phenyl)methanol (Diastereomer 2) (example VII (7)).
Mass spectrometry (ESI+): m/z=534 [M+H]+
HPLC (Method 9): Retention time=14.04 min.

(7) (8S)-8-(tert-Butyldimethylsilyloxy)-9-isopropyl-3,6,6-trimethyl-1-(4-(trifluoromethyl)phenyl)-1,3,5,6,7,8-hexahydrofuro[3,4-b]quinoline

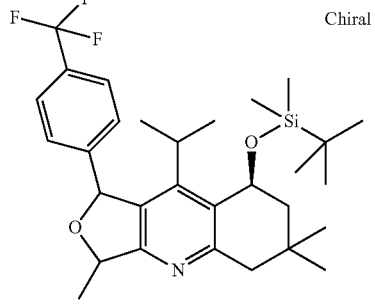

The compound is obtained from ((5S)-5-(tert-Butyldimethylsilyloxy)-4-isopropyl-2-(1-methoxyethyl)-7,7-dimethyl-5,6,7,8-tetrahydroquinolin-3-yl)-(4-(trifluoromethyl)phenyl)methanol (Diastereomer 1) (example VII (7)).
Mass spectrometry (ESI+): m/z=534 [M+H]+
HPLC (Method 9): Retention time=14.2 min.

(8) (8S)-8-(Tert-butyldimethylsilyloxy)-9-(4-fluorophenyl)-3,6,6-trimethyl-1-(4-(trifluoromethyl)phenyl)-1,3,5,6,7,8-hexahydrofuro[3,4-b]quinoline (Diastereomer 1)

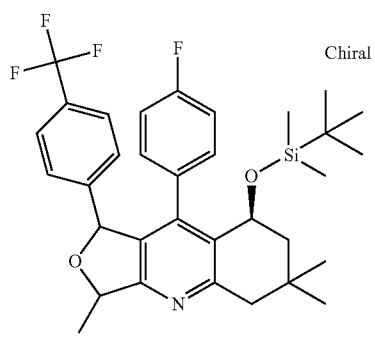 [SMILES: CC1OC(c2ccc(C(F)(F)F)cc2)c2c1nc1c(c2-c2ccc(F)cc2)[C@@H](O[Si](C)(C)C(C)(C)C)CC(C)(C)C1]

and (8S)-8-(tert-Butyldimethylsilyloxy)-9-(4-fluorophenyl)-3,6,6-trimethyl-1-(4-(trifluoromethyl)phenyl)-1,3,5,6,7,8-hexahydrofuro[3,4-b]quinoline (Diastereomer 2)

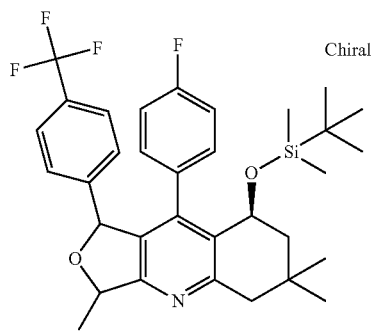 [SMILES: CC1OC(c2ccc(C(F)(F)F)cc2)c2c1nc1c(c2-c2ccc(F)cc2)[C@@H](O[Si](C)(C)C(C)(C)C)CC(C)(C)C1]

The compounds are obtained starting from with ((5S)-5-(tert-Butyldimethylsilyloxy)-4-(4-fluorophenyl)-2-(1-methoxyethyl)-7,7-dimethyl-5,6,7,8-tetrahydroquinolin-3-yl)(4-(trifluoromethyl)phenyl)methanol (Diastereomer 2) as a mixture of diastereomers. The mixture is directly submitted to the next step (example 1 (12)).

Mass spectrometry (ESI$^+$): m/z=586 [M+H]$^+$

Diastereomer 1 and Diastereomer 2 give retention times of 14.04 and 14.58 by HPLC Method 10.

Example X

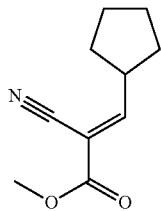

2-Cyano-3-cyclopentyl-acrylic acid methyl ester 10 g Cyclopentanecarbaldehyde are dissolved in 100 ml acetonitrile, cooled to 0° C. and hereto 10 ml of piperidine are added dropwise. Afterwards 9 ml cyano-acetic acid methyl ester are added and then 8 ml trifluoroacetic acid are added dropwise. The temperature is raised to 60° C. for 16 hours. After cooling to room temperature the solvents are evaporated in vacuo and the residue is chromatographed on silica gel (cyclohexane/ethylacetate 95:5 to 80:20).

Yield: 15 g (85% of theory)

Mass spectrometry (ESI$^-$): m/z=178 [M–H]$^-$

R$_f$-value: 0.54 (silica gel, petrole ether/ethylacetate 4:1)

Example XI

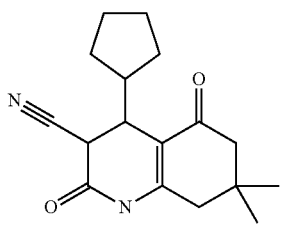 [SMILES: CC1(C)CC(=O)C2=C(C1)NC(=O)C(C#N)C2C1CCCC1]

4-Cyclopentyl-7,7-dimethyl-2,5-dioxo-1,2,3,4,5,6,7,8-octahydro-quinoline-3-carbonitrile 13.3 g 2-Cyano-3-cyclopentyl-acrylic acid methyl ester and 5.8 ml trifluoroacetic acid are dissolved in 70 ml acetonitrile and heated for 7 days to reflux. During the first 5 days 3-amino-5,5-dimethyl-cyclohex-2-enone is added in daily portions (12 g in total). Afterwards the reaction mixture is cooled to 0° C., the precipitate is isolated by filtration, washed 2 times with cold acetonitrile and dried in vacuo. The product is obtained as a mixture of diastereomers.

Yield: 11 g (52% of theory)

Mass spectrometry (ESI$^+$): m/z=287 [M+H]$^+$

HPLC (Method 2): Retention time=3.35 min.

Example XII

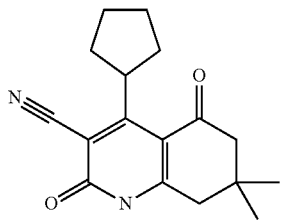 [SMILES: CC1(C)CC(=O)c2c([nH]c(=O)c(C#N)c2C2CCCC2)C1]

4-Cyclopentyl-7,7-dimethyl-2,5-dioxo-1,2,5,6,7,8-hexahydro-quinoline-3-carbonitrile 11.0 g 4-Cyclopentyl-7,7-dimethyl-2,5-dioxo-1,2,3,4,5,6,7,8-octahydro-quinoline-3-carbonitrile are suspended in 160 ml acetonitrile, heated to 60° C. and mixed dropwise with a solution of 85 g ammonium cer-(IV)-nitrate in 80 ml water. After heating for 1 h the mixture is diluted with 1200 ml dichloromethane and vigorously stirred. The aqueous bottom phase is discarded and the organic phase is washed successively with saturated sodium bicarbonate and brine. After drying with magnesium sulphate the solvents are evaporated in vacuo and the residue is triturated with diethylether. The solid is isolated by filtration, washed with diethylether and dried in vacuo.

Yield: 7 g (64% of theory)

Mass spectrometry (ESI$^+$): m/z=285 [M+H]$^+$

HPLC (Method 2): Retention time=3.32 min.

Example XIII

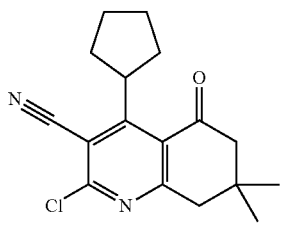 [SMILES: CC1(C)CC(=O)c2c(nc(Cl)c(C#N)c2C2CCCC2)C1]

2-Chloro-4-cyclopentyl-7,7-dimethyl-5-oxo-5,6,7,8-tetrahydro-quinoline-3-carbonitrile 3.05 g 4-Cyclopentyl-7,7-dimethyl-2,5-dioxo-1,2,5,6,7,8-hexahydro-quinoline-3-carbonitrile are suspended in 40 ml dichloromethane, mixed with 2.25 g phosphorpentachloride and stirred for 6 hours at room temperature. Then 20 ml Toluene are added in the mixture is heated for 12 hours at 55° C. The solvents are evaporated in vacuo and the residue is triturated with methanol. The solid is collected by filtration, washed with methanol and dried in vacuo.

Yield: 2.85 g (88% of theory)

Mass spectrometry (ESI$^+$): m/z=303 [M+H]$^+$

R$_f$-value: 0.53 (silica gel, petrole ether/ethylacetate 4:1)

Example XIV

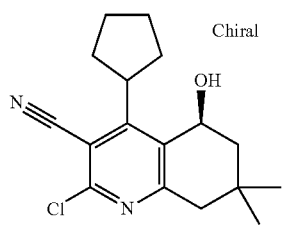 [SMILES: CC1(C)Cc2nc(Cl)c(C#N)c(C3CCCC3)c2[C@@H](O)C1]

5-(S)-2-Chloro-4-cyclopentyl-5-hydroxy-7,7-dimethyl-5,6,7,8-tetrahydro-quinoline-3-carbonitrile 300 mg (1R,2S)-(+)-cis-1-Amino-2-indanol are dissolved in 100 ml tetrahydrofurane and to this solution are dropwise added 2.6 ml of a borane-diethylaniline-complex. After completion of gas evolution the solution is cooled to 0° C. and 2.21 g 2-chloro-4-cyclopentyl-7,7-dimethyl-5-oxo-5,6,7,8-tetrahydro-quinoline-3-carbonitrile in 20 ml tetrahydrofurane are added dropwise. The temperature is raised during 12 hours to room temperature, 20 ml methanol are added dropwise and the mixture is stirred for additional 10 minutes. The solvents are evaporated in vacuo and the residue is partitioned between water and diethylether. The aqueous phase is extracted twice with diethylether and the combined organic phases are washed successively with 4 M hydrochloric acid and brine. After drying with magnesium sulphate the solvents are evaporated in vacuo and the residue is triturated with petrolether. The solid is collected by filtration and dried in vacuo.

Yield: 2.0 g (90% of theory)

Mass spectrometry (ESI$^+$): m/z=305 [M+H]$^+$

R$_f$-value: 0.26 (silica gel, petrole ether/ethylacetate 4:1)

The enantiomeric excess as determined by HPLC Method 1 is 45%.

Analogously to example XIV the following compounds are obtained:

(1) 5-(S)-4-Cyclohexyl-5-hydroxy-2-(1-methoxy-ethyl)-7,7-dimethyl-5,6,7,8-tetrahydro-quinoline-3-carboxylic acid ethyl ester

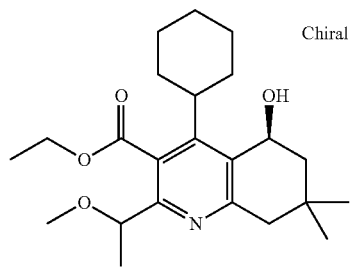 [SMILES: CCOC(=O)c1c(C(C)OC)nc2c(c1C1CCCCC1)[C@@H](O)CC(C)(C)C2]

Mass spectrometry (ESI$^+$): m/z=390 [M+H]$^+$

Example XV

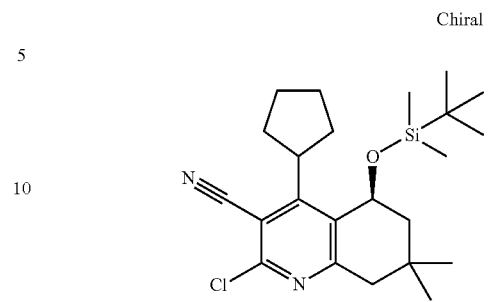

5-(S)-5-(tert-Butyl-dimethyl-silanyloxy)-2-chloro-4-cyclopentyl-7,7-dimethyl-5,6,7,8-tetrahydro-quinoline-3-carbonitrile 200 mg 5-(S)-2-Chloro-4-cyclopentyl-5-hydroxy-7,7-dimethyl-5,6,7,8-tetrahydro-quinoline-3-carbonitrile are dissolved in 10 ml diethylether, 120 µl 2,6-lutidine are added and the solution is cooled to 0° C. 190 µl trifluoromethanesulfonic acid-tert.-butyldimethylsilylester are added dropwise and the mixture is stirred for further 12 hours during which time the temperature is raised to room temperature. Afterwards 5 ml tetrahydrofurane and 120 µl 2,6-lutidine are added, followed by the dropwise addition of 190 µl trifluoromethanesulfonic acid-tert.-butyldimethylsilylester. The mixture is stirred for further 24 h at room temperature. Then it is partitioned between 1 M hydrochloric acid and ethylacetate. The aqueous phase is twice extracted with ethylacetate and the combined organic phases are washed successively with sodium bicarbonate and brine. After drying with magnesium sulphate the solvents are evaporated in vacuo and the residue is chromatographed on silica gel (cyclohexane/ethylacetate 95:5 to 85:15).

Yield: 210 mg (76% of theory)

Mass spectrometry (ESI$^+$): m/z=419 [M+H]$^+$

R$_f$-value: 0.83 (silica gel, petrole ether/ethylacetate 4:1)

Analogously to example XV the following compounds are obtained:

(1) 5-(S)-5-(tert-Butyl-dimethyl-silanyloxy)-4-cyclohexyl-2-(1-methoxy-ethyl)-7,7-dimethyl-5,6,7,8-tetrahydro-quinoline-3-carboxylic acid ethyl ester

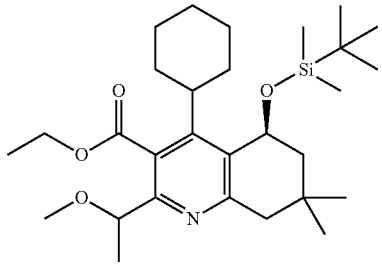

Toluene is used instead of diethylether as solvent.

Mass spectrometry (ESI$^+$): m/z=504 [M+H]$^+$

Example XVI

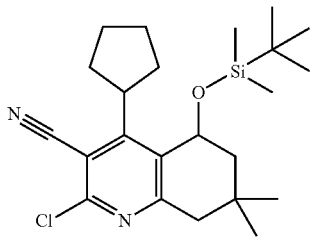 [SMILES: CC1(C)Cc2nc(Cl)c(C#N)c(C3CCCC3)c2C(O[Si](C)(C)C(C)(C)C)C1]

5-(tert-Butyl-dimethyl-silanyloxy)-2-chloro-4-cyclopentyl-7,7-dimethyl-5,6,7,8-tetrahydro-quinoline-3-carbonitrile A solution of 376 mg 2-Chloro-4-cyclopentyl-7,7-dimethyl-5-oxo-5,6,7,8-tetrahydro-quinoline-3-carbonitrile in 10 ml tetrahydrofurane is cooled to 0° C., treated with 30 mg lithium aluminium borohydride and stirred for 1 h at room temperature. The mixture is partitioned between saturated ammonium chloride and ethylacetate. The aqueous phase is extracted three times with ethylacetate and the combined organic phases are dried with magnesium sulphate. Then the solvents are evaporated in vacuo and the residue is taken up in 10 ml toluene. After cooling to 0° C. 578 µl 2,6-lutidine and 371 µl trifluoromethanesulfonic acid-tert.-butyldimethylsilylester are added dropwise. The mixture is stirred for 1 h at 0° C. and then partitioned between saturated ammonium chloride and ethylacetate. The aqueous phase is extracted twice with ethylacetate and the combined organic phases are dried with magnesium sulphate. Then the solvents are evaporated in vacuo and the residue is chromatographed on silica gel (cyclohexane/ethylacetate 95:5 to 85:15).

Yield: 390 mg (75% of theory)
Mass spectrometry (ESI$^+$): m/z=419 [M+H]$^+$

Example XVII

Chiral

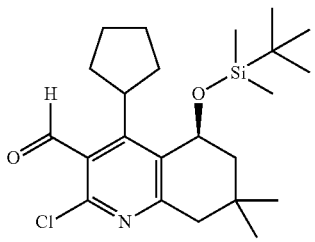

5-(S)-5-(tert-Butyl-dimethyl-silanyloxy)-2-chloro-4-cyclopentyl-7,7-dimethyl-5,6,7,8-tetrahydro-quinoline-3-carbaldehyde A solution of 200 mg 5-(S)-5-(tert-Butyl-dimethyl-silanyloxy)-2-chloro-4-cyclopentyl-7,7-dimethyl-5,6,7,8-tetrahydro-quinoline-3-carbonitrile in 5 ml dichloromethane is cooled to 0° C. and mixed dropwise with 500 µl of a 1 M solution of diisobutylaluminum hydride in toluene. After stirring for 1 hour the mixture is partitioned between 1 M hydrochloric acid and ethylacetate. The organic phase is washed with saturated sodium bicarbonate and brine. Subsequently it is dried with magnesium sulphate. Then the solvents are evaporated in vacuo and the residue is chromatographed on silica gel (cyclohexane/ethylacetate 95:5 to 75:25).

Yield: 110 mg (55% of theory)
Mass spectrometry (ESI$^+$): m/z=422 [M+H]$^+$
R$_f$-value: 0.41 (silica gel, petrole ether/ethylacetate 8:1)

Analogously to example XVII the following compounds are obtained:

(1) 5-(tert-Butyl-dimethyl-silanyloxy)-2-chloro-4-cyclopentyl-7,7-dimethyl-5,6,7,8-tetrahydro-quinoline-3-carbaldehyde

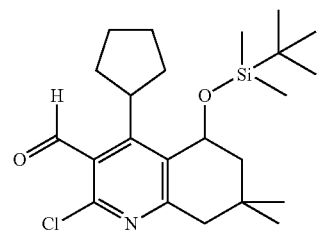 [SMILES: CC1(C)Cc2nc(Cl)c(C=O)c(C3CCCC3)c2C(O[Si](C)(C)C(C)(C)C)C1]

Mass spectrometry (ESI$^+$): m/z=422 [M+H]$^+$

Example XVIII

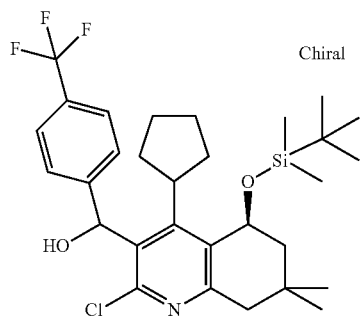 [SMILES: CC1(C)Cc2nc(Cl)c(C(O)c3ccc(C(F)(F)F)cc3)c(C3CCCC3)c2[C@@H](O[Si](C)(C)C(C)(C)C)C1]

Chiral 5-(S)-[5-(tert-Butyl-dimethyl-silanyloxy)-2-chloro-4-cyclopentyl-7,7-dimethyl-5,6,7,8-tetrahydro-quinolin-3-yl]-(4-trifluoromethyl-phenyl)-methanol A solution of 150 µl 1-Iodo-4-trifluoromethyl-benzene are in 5 ml tetrahydrofurane is cooled to −40° C. and 500 µl of a 2 M solution of isopropylmagnesium chloride in tetrahydrofurane is added dropwise. After stirring for 4 hours 100 mg of 5-(S)-5-(tert-Butyl-dimethyl-silanyloxy)-2-chloro-4-cyclopentyl-7,7-dimethyl-5,6,7,8-tetrahydro-quinoline-3-carbaldehyde are added and the mixture is stirred for further 4 hours during which time the temperature is raised to 0° C. Methanol (2 ml) is added and the mixture is stirred for 30 minutes at room temperature. The solvents are evaporated in vacuo and the residue is chromatographed on silica gel (cyclohexane/ethylacetate 95:5 to 60:40). The product is obtained as a mixture of diastereomers.

Yield: 110 mg (82% of theory)
Mass spectrometry (ESI$^+$): m/z=568 [M+H]$^+$
The diastereomers give R$_f$-values of 0.58 and 0.62 (silica gel, petrole ether/ethylacetate 4:1)

Analogously to example XVIII the following compounds are obtained:

(1) [5-(tert-Butyl-dimethyl-silanyloxy)-2-chloro-4-cyclopentyl-7,7-dimethyl-5,6,7,8-tetrahydro-quinolin-3-yl]-(4-trifluoromethyl-phenyl)-methanol

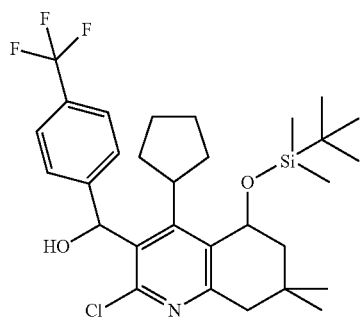 [SMILES: CC1(C)Cc2nc(Cl)c(C(O)c3ccc(C(F)(F)F)cc3)c(C3CCCC3)c2C(O[Si](C)(C)C(C)(C)C)C1]

Mass spectrometry (ESI$^+$): m/z=568 [M+H]$^+$
The product is obtained as a mixture of diastereomers.
HPLC (Method 4): Retention time=3.30 min.

(2) 5-(S)-[5-(tert-Butyl-dimethyl-silanyloxy)-4-cyclohexyl-2-(1-methoxy-ethyl)-7,7-dimethyl-5,6,7,8-tetrahydro-quinolin-3-yl]-(4-tert-butyl-phenyl)-methanol

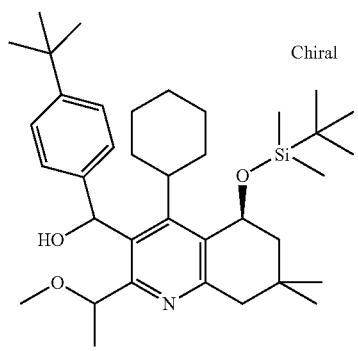 [SMILES: COC(C)c1nc2c(c(C3CCCCC3)c1C(O)c1ccc(C(C)(C)C)cc1)[C@@H](O[Si](C)(C)C(C)(C)C)CC(C)(C)C2]

Prepared from commercially available 4-tert.-Butyl-phenyl-magnesium bromide. Dioxane is used instead of tetrahydrofurane as solvent.
Mass spectrometry (ESI$^+$): m/z=594 [M+H]$^+$ Example XIX

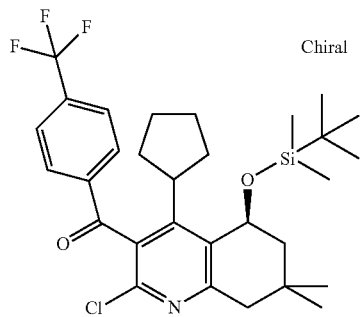 [SMILES: CC1(C)Cc2nc(Cl)c(C(=O)c3ccc(C(F)(F)F)cc3)c(C3CCCC3)c2[C@@H](O[Si](C)(C)C(C)(C)C)C1]

5-(S)-[5-(tert-Butyl-dimethyl-silanyloxy)-2-chloro-4-cyclopentyl-7,7-dimethyl-5,6,7,8-tetrahydro-quinolin-3-yl]-(4-trifluoromethyl-phenyl)-methanone 240 mg 5-(S)-[5-(tert-Butyl-dimethyl-silanyloxy)-2-chloro-4-cyclopentyl-7,7-dimethyl-5,6,7,8-tetrahydro-quinolin-3-yl]-(4-trifluoromethyl-phenyl)-methanol are dissolved in 5 ml dichloromethane, cooled to 0° C. and treated with 240 mg Dess-Martin-Periodinan. After stirring for 3 hours the solvent is evaporated in vacuo and the residue is chromatographed on silica gel (cyclohexane/ethylacetate 95:5 to 80:20).

Yield: 230 mg (96% of theory)

$R_f$-value: 0.67 (silica gel, petrole ether/ethylacetate 8:1)

Example XX

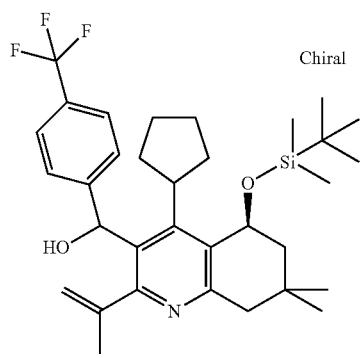

5-(S)-[5-(tert-Butyl-dimethyl-silanyloxy)-4-cyclopentyl-2-isopropenyl-7,7-dimethyl-5,6,7,8-tetrahydro-quinolin-3-yl]-(4-trifluoromethyl-phenyl)-methanol 105 mg 5-(S)-[5-(tert-Butyl-dimethyl-silanyloxy)-2-chloro-4-cyclopentyl-7,7-dimethyl-5,6,7,8-tetrahydro-quinolin-3-yl]-(4-trifluoromethyl-phenyl)-methanol and 160 mg 2-isopropylideneboronic acid are dissolved in 2 ml tetrahydrofurane and 2 ml toluene. Sodium carbonate (230 µl of a 2 M solution in water) is added and argon is bubbled through the mixture for several minutes. Then 45 mg of tetrakis-triphenylphosphin-palladium-(0) are added the flask is sealed and the mixture is heated for 48 hours at 85° C. Afterwards the mixture is diluted with dichloromethane and dried with magnesium sulphate. The solvents are evaporated in vacuo and the residue is chromatographed on silica gel (cyclohexane/ethylacetate 90:10 to 60:40).

Yield: 39 mg (37% of theory)

Mass spectrometry (ESI$^+$): m/z=574 [M+H]$^+$

Analogously to example XX the following compounds are obtained:

(1) [5-(tert-Butyl-dimethyl-silanyloxy)-4-cyclopentyl-2-isopropenyl-7,7-dimethyl-5,6,7,8-tetrahydroquinolin-3-yl]-(4-trifluoromethyl-phenyl)-methanol

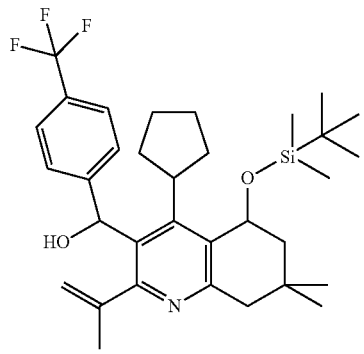 [SMILES: C=C(C)c1nc2c(c(C3CCCC3)c1C(O)c1ccc(C(F)(F)F)cc1)C(O[Si](C)(C)C(C)(C)C)CC(C)(C)C2]

The crude product is directly used in example XXI
Mass spectrometry (ESI$^+$): m/z=574 [M+H]$^+$ (2) 5-(S)-[5-(tert-Butyl-dimethyl-silanyloxy)-4-cyclopentyl-2-isopropenyl-7,7-dimethyl-5,6,7,8-tetrahydro-quinolin-3-yl]-(4-trifluoromethyl-phenyl)-methanone

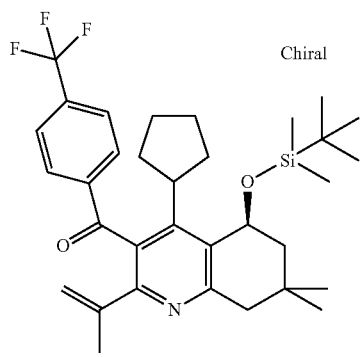 [SMILES: C=C(C)c1nc2c(c(C3CCCC3)c1C(=O)c1ccc(C(F)(F)F)cc1)[C@@H](O[Si](C)(C)C(C)(C)C)CC(C)(C)C2]

Mass spectrometry (ESI$^+$): m/z=572 [M+H]$^+$
$R_f$-value: 0.32 (silica gel, petrole ether/ethylacetate 16:1)

(3) (S)-(5-(tert-Butyldimethylsilyloxy)-2-cyclohexenyl-4-cyclopentyl-7,7-dimethyl-5,6,7,8-tetrahydroquinolin-3-yl)-(4-(trifluoromethyl)phenyl)methanone

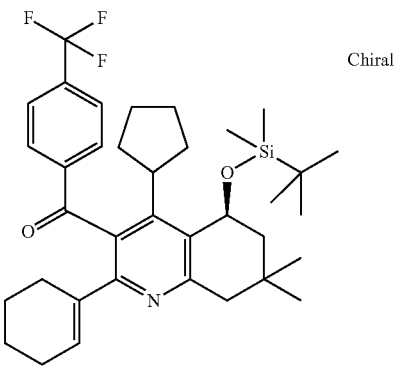 [SMILES: CC1(C)Cc2nc(C3=CCCCC3)c(C(=O)c3ccc(C(F)(F)F)cc3)c(C3CCCC3)c2[C@@H](O[Si](C)(C)C(C)(C)C)C1]

Mass spectrometry (ESI$^+$): m/z=612 [M+H]$^+$
$R_f$-value: 0.42 (silica gel, petrole ether/ethylacetate 16:1)

(4) (S)-(5-(tert-Butyldimethylsilyloxy)-2-cyclopentenyl-4-cyclopentyl-7,7-dimethyl-5,6,7,8-tetrahydroquinolin-3-yl)-(4-(trifluoromethyl)phenyl)methanone

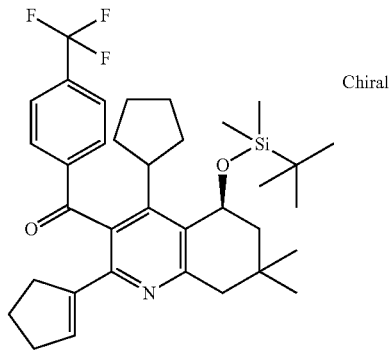 [SMILES: CC1(C)Cc2nc(C3=CCCC3)c(C(=O)c3ccc(C(F)(F)F)cc3)c(C3CCCC3)c2[C@@H](O[Si](C)(C)C(C)(C)C)C1]

Mass spectrometry (ESI$^+$): m/z=598 [M+H]$^+$
$R_f$-value: 0.43 (silica gel, petrol ether/ethylacetate 16:1)
HPLC (Method 4): Retention time=3.30 min.

Example XXI

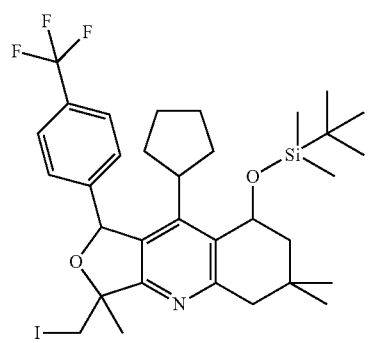 [SMILES: CC1(C)Cc2nc3c(c(C4CCCC4)c2C(O[Si](C)(C)C(C)(C)C)C1)C(c1ccc(C(F)(F)F)cc1)OC3(C)CI]

8-(tert-Butyl-dimethyl-silanyloxy)-9-cyclopentyl-3-iodomethyl-3,6,6-trimethyl-1-(4-trifluoromethyl-phenyl)-1,3,5,6,7,8-hexahydro-furo[3,4-b]quinoline A solution of 9 mg [5-(tert-Butyl-dimethyl-silanyloxy)-4-cyclopentyl-2-isopropenyl-7,7-dimethyl-5,6,7,8-tetrahydroquinolin-3-yl]-(4-trifluoromethyl-phenyl)-methanol in 1 ml of acetonitrile is cooled to 0° C. and mixed under argon successively with 2.7 mg sodium bicarbonate, 8 mg iodine and 3.7 mg silver-(I)-oxide. After stirring for 3 hours at room temperature the mixture is partitioned between 5% aqueous sodium thiosulfate and ethylacetate. The aqueous phase is extracted twice with ethylacetate and the combined organic phases are washed with brine. After drying with magnesium sulphate the solvents are evaporated in vacuo and the residue is chromatographed on silica gel (cyclohexane/ethylacetate 90:10 to 70:30). The product thus obtained is directly submitted to the next step (example XXII).

Mass spectrometry (ESI$^+$): m/z=700 [M+H]$^+$
HPLC (Method 4): Retention time=3.38 min.

Analogously to example XXI the following compounds are obtained:

(1) (8'S)-8'-(tert-Butyldimethylsilyloxy)-9'-cyclopentyl-2-iodo-6',6'-dimethyl-1'-(4-(trifluoromethyl)phenyl)-5',6',7',8'-tetrahydro-1'H-spiro[cyclohexane-1,3'-furo[3,4-b]quinoline]

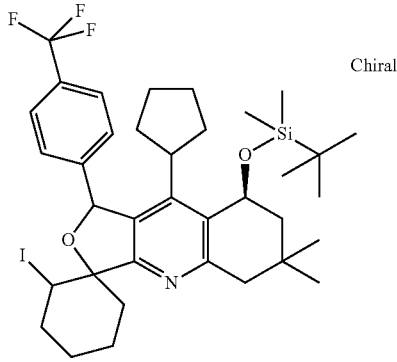 [SMILES: CC1(C)Cc2nc3c(c(C4CCCC4)c2[C@@H](O[Si](C)(C)C(C)(C)C)C1)C(c1ccc(C(F)(F)F)cc1)OC31CCCCC1I]

Mass spectrometry (ESI⁺): m/z=740 [M+H]⁺
R$_f$-value: 0.31 (silica gel, petrole ether/ethylacetate 16:1)
HPLC (Method 4): Retention time=3.651 min.

(2) (8'S)-8'-(tert-butyldimethylsilyloxy)-9'-cyclopentyl-2-iodo-6',6'-dimethyl-1'-(4-(trifluoromethyl)phenyl)-5',6',7',8'-tetrahydro-1'H-spiro[cyclopentane-1,3'-furo[3,4-b]quinoline]

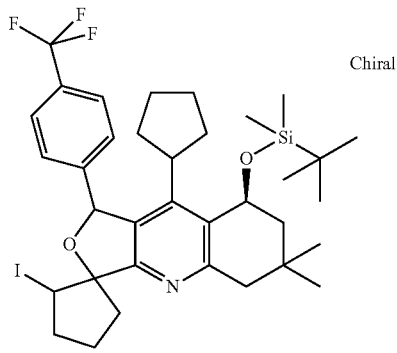 [SMILES: CC1(C)Cc2nc3c(c(C4CCCC4)c2[C@@H](O[Si](C)(C)C(C)(C)C)C1)C(c1ccc(C(F)(F)F)cc1)OC31CCCC1I]

Mass spectrometry (ESI⁺): m/z=726 [M+H]⁺
R$_f$-value: 0.38 (silica gel, petrole ether/ethylacetate 8:1)
HPLC (Method 4): Retention time=3.50 min.

Example XXII

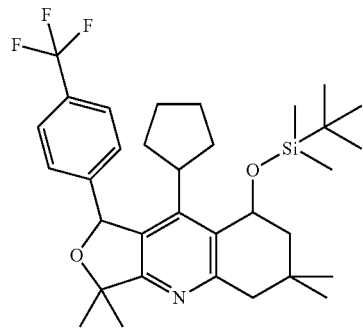 [SMILES: CC1(C)Cc2nc3c(c(C4CCCC4)c2C(O[Si](C)(C)C(C)(C)C)C1)C(c1ccc(C(F)(F)F)cc1)OC3(C)C]

8-(tert-Butyl-dimethyl-silanyloxy)-9-cyclopentyl-3,3,6,6-tetramethyl-1-(4-trifluoromethyl-phenyl)-1,3,5,6,7,8-hexahydro-furo[3,4-b]quinoline 10 mg 8-(tert-Butyl-dimethyl-silanyloxy)-9-cyclopentyl-3-iodomethyl-3,6,6-trimethyl-1-(4-trifluoromethyl-phenyl)-1,3,5,6,7,8-hexahydro-furo[3,4-b]quinoline (example XXI) are dissolved in 1 ml toluene and mixed successively under argon with 300 µl tris-trimethylsilyl-silane and 1 mg azo-bis-isobutyro-nitrile. The reaction mixture is heated for 4 hours to 110° C. and for 12 hours at room temperature. After addition of 1 ml methanol the solvents are evaporated in vacuo and the residue is partitioned between water and ethylacetate. The aqueous phase is extracted twice with ethylacetate and the combined organic phases are washed with brine. After drying with magnesium sulphate the solvents are evaporated in vacuo. The crude product thus obtained is directly submitted to the next step (example 1 (4)).
Mass spectrometry (ESI⁺): m/z=574 [M+H]⁺
HPLC (Method 4): Retention time=3.18 min.

Example XXIII

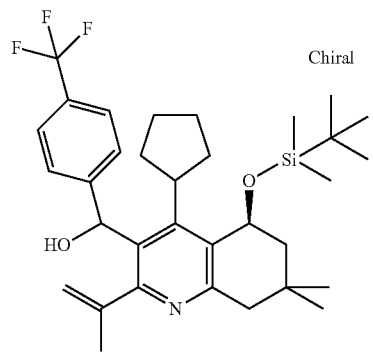 [SMILES: C=C(C)c1nc2c(c(C3CCCC3)c1C(O)c1ccc(C(F)(F)F)cc1)[C@@H](O[Si](C)(C)C(C)(C)C)CC(C)(C)C2]

5-(S)-[5-(tert-Butyl-dimethyl-silanyloxy)-4-cyclopentyl-2-isopropenyl-7,7-dimethyl-5,6,7,8-tetrahydro-quinolin-3-yl]-(4-trifluoromethyl-phenyl)-methanol (Diastereomer 1) and

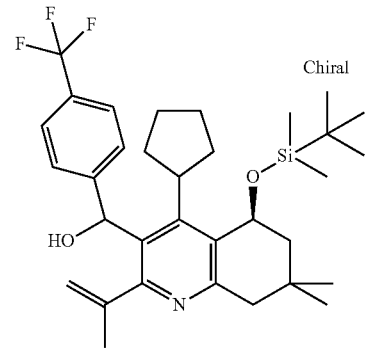 [SMILES: C=C(C)c1nc2c(c(C3CCCC3)c1C(O)c1ccc(C(F)(F)F)cc1)[C@@H](O[Si](C)(C)C(C)(C)C)CC(C)(C)C2]

5-(S)-[5-(tert-Butyl-dimethyl-silanyloxy)-4-cyclopentyl-2-isopropenyl-7,7-dimethyl-5,6,7,8-tetrahydro-quinolin-3-yl]-(4-trifluoromethyl-phenyl)-methanol (Diastereomer 2)

125 mg 5-(S)-[5-(tert-Butyl-dimethyl-silanyloxy)-4-cyclopentyl-2-isopropenyl-7,7-dimethyl-5,6,7,8-tetrahydroquinolin-3-yl]-(4-trifluoromethyl-phenyl)-methanone are dissolved in 10 ml tetrahydrofurane cooled to 0° C. and mixed with 890 µl of a 1 M solution of lithium ammonium hydride in tetrahydrofurane. The mixture is stirred for 2 h, diluted with ethylacetate and mixed with 890 µl of a 1 M hydrochloric acid. Then the mixture is dried with magnesium sulphate, the solvents are evaporated in vacuo and the residue is chromatographed on silica gel (cyclohexane/ethylacetate 95:5 to 70:30).

5-(S)-[5-(tert-Butyl-dimethyl-silanyloxy)-4-cyclopentyl-2-isopropenyl-7,7-dimethyl-5,6,7,8-tetrahydro-quinolin-3-yl]-(4-trifluoromethyl-phenyl)methanol (Diastereomer 1)

Yield: 30 mg (24% of theory)
$R_f$-value: 0.72 (silica gel, petrole ether/ethylacetate 4:1)
Mass spectrometry (ESI$^+$): m/z=574 [M+H]$^+$ 5-(S)-[5-(tert-Butyl-dimethyl-silanyloxy)-4-cyclopentyl-2-isopropenyl-7,7-dimethyl-5,6,7,8-tetrahydro-quinolin-3-yl]-(4-trifluoromethyl-phenyl)-methanol (Diastereomer 2)

Yield: 35 mg (28% of theory)
$R_f$-value: 0.58 (silica gel, petrole ether/ethylacetate 4:1)
Mass spectrometry (ESI$^+$): m/z=574 [M+H]$^+$ Analogously to example XXIII the following compounds are obtained:

(1) ((S)-5-(tert-Butyldimethylsilyloxy)-2-cyclohexenyl-4-cyclopentyl-7,7-dimethyl-5,6,7,8-tetrahydro-quinolin-3-yl)-(4-(trifluoromethyl)phenyl)methanol

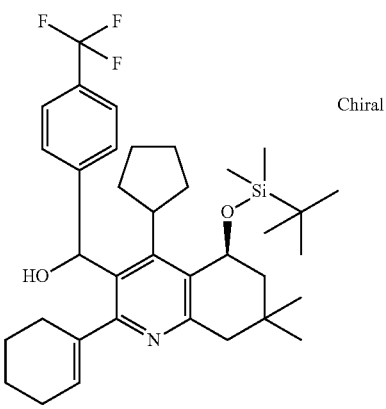 [SMILES: CC1(C)Cc2nc(C3=CCCCC3)c(C(O)c3ccc(C(F)(F)F)cc3)c(C3CCCC3)c2[C@@H](O[Si](C)(C)C(C)(C)C)C1]

Mass spectrometry (ESI$^+$): m/z=614 [M+H]$^+$
$R_f$-value: 0.3 (silica gel, petrol ether/ethylacetate 8:1)
HPLC (Method 4): Retention time=1.95 min.

(2) ((S)-5-(tert-Butyldimethylsilyloxy)-2-cyclopentenyl-4-cyclopentyl-7,7-dimethyl-5,6,7,8-tetrahydro-quinolin-3-yl)-(4-(trifluoromethyl)phenyl)methanol

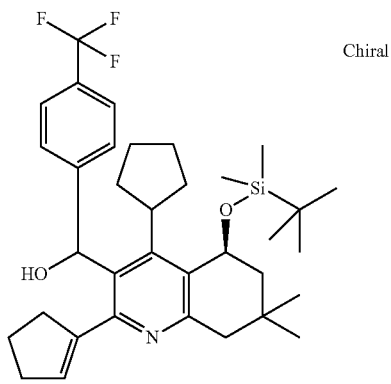 [SMILES: CC1(C)Cc2nc(C3=CCCC3)c(C(O)c3ccc(C(F)(F)F)cc3)c(C3CCCC3)c2[C@@H](O[Si](C)(C)C(C)(C)C)C1]

Mass spectrometry (ESI$^+$): m/z=600 [M+H]$^+$
HPLC (Method 4): Retention time=1.97 min.

Example XXIV

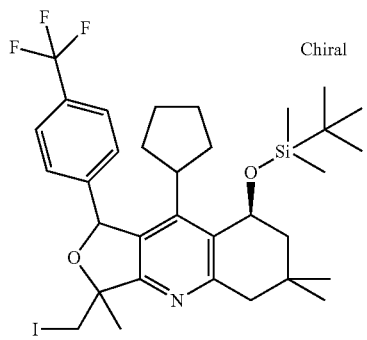

8-(S)-8-(tert-Butyl-dimethyl-silanyloxy)-9-cyclopentyl-3-iodomethyl-3,6,6-trimethyl-1-(4-trifluoromethyl-phenyl)-1,3,5,6,7,8-hexahydro-furo[3,4-b] quinoline (Diastereomer 1)

and

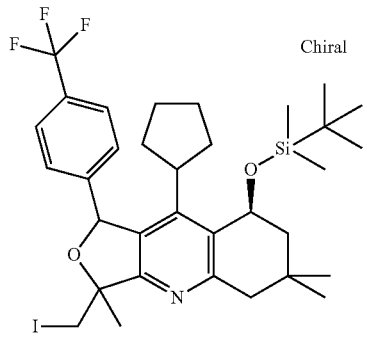

8-(S)-8-(tert-Butyl-dimethyl-silanyloxy)-9-cyclopentyl-3-iodomethyl-3,6,6-trimethyl-1-(4-trifluoromethyl-phenyl)-1,3,5,6,7,8-hexahydro-furo[3,4-b]quinoline (Diastereomer 2)

30 mg 5-(S)-[5-(tert-Butyl-dimethyl-silanyloxy)-4-cyclopentyl-2-isopropenyl-7,7-dimethyl-5,6,7,8-tetrahydro-quinolin-3-yl]-(4-trifluoromethyl-phenyl)-methanol (Diastereomer 1) are dissolved in 3 ml tetrahydrofurane and cooled to 0° C. Afterwards 10 mg sodium bicarbonate, 30 mg iodine and 15 mg silver-I-oxide are added successively. The mixture is stirred for 12 hours at room temperature and under exclusion of light. Thereafter the mixture is diluted with ethylacetate and washed with 5% sodium thiosulphate and brine. After drying with magnesium sulphate the solvents are evaporated in vacuo and the residue is chromatographed on silica gel (cyclohexane/ethylacetate 95:5 to 70:30).

8-(S)-8-(tert-Butyl-dimethyl-silanyloxy)-9-cyclopentyl-3-iodomethyl-3,6,6-trimethyl-1-(4-trifluoromethyl-phenyl)-1,3,5,6,7,8-hexahydro-furo[3,4-b]quinoline (Diastereomer 1)

Yield: 13 mg (36% of theory)
HPLC (Method 4): Retention time=3.28 min.
Mass spectrometry (ESI$^+$): m/z=700 [M+H]$^+$ 8-(S)-8-(tert-Butyl-dimethyl-silanyloxy)-9-cyclopentyl-3-iodomethyl-3,6,6-trimethyl-1-(4-trifluoromethyl-phenyl)-1,3,5,6,7,8-hexahydro-furo[3,4-b]quinoline (Diastereomer 2)

Yield: 14 mg (38% of theory)
HPLC (Method 4): Retention time=3.24 min.
Mass spectrometry (ESI$^+$): m/z=700 [M+H]$^+$ Analogously to example XXIV the following compounds are obtained:

(1) 8-(S)-8-(tert-Butyl-dimethyl-silanyloxy)-9-cyclopentyl-3-iodomethyl-3,6,6-trimethyl-1-(4-trifluoromethyl-phenyl)-1,3,5,6,7,8-hexahydro-furo[3,4-b]quinoline (Diastereomer 3)

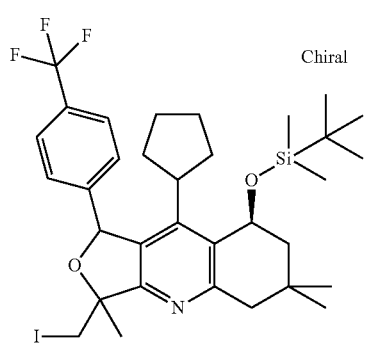 [SMILES: CC1(C)Cc2nc3c(c(C4CCCC4)c2[C@@H](O[Si](C)(C)C(C)(C)C)C1)C(c1ccc(C(F)(F)F)cc1)OC3(C)CI]

and 8-(S)-8-(tert-Butyl-dimethyl-silanyloxy)-9-cyclopentyl-3-iodomethyl-3,6,6-trimethyl-1-(4-trifluoromethyl-phenyl)-1,3,5,6,7,8-hexahydro-furo[3,4-b]quinoline (Diastereomer 4)

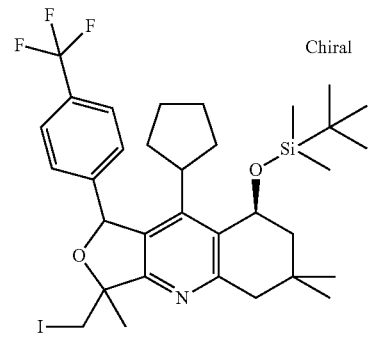

The compounds are obtained as a mixture of diastereomers starting from 5-(S)-[5-(tert-Butyl-dimethyl-silanyloxy)-4-cyclopentyl-2-isopropenyl-7,7-dimethyl-5,6,7,8-tetrahydro-quinolin-3-yl]-(4-trifluoromethyl-phenyl)methanol (Diastereomer 2).

HPLC (Method 4): Retention time=3.26 min.
Mass spectrometry (ESI$^+$): m/z=700 [M+H]$^+$ Example XXV

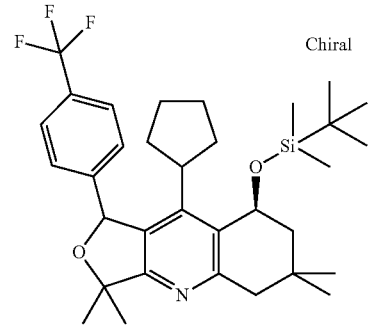 [SMILES: CC1(C)Cc2nc3c(c(C4CCCC4)c2[C@@H](O[Si](C)(C)C(C)(C)C)C1)C(c1ccc(C(F)(F)F)cc1)OC3(C)C]

8-(S)-8-(tert-Butyl-dimethyl-silanyloxy)-9-cyclopentyl-3,3,6,6-tetramethyl-1-(4-trifluoromethyl-phenyl)-1,3,5,6,7,8-hexahydro-furo[3,4-b]quinoline (Diastereomer 1)

11 mg 8-(S)-8-(tert-Butyl-dimethyl-silanyloxy)-9-cyclopentyl-3-iodomethyl-3,6,6-trimethyl-1-(4-trifluoromethyl-phenyl)-1,3,5,6,7,8-hexahydro-furo[3,4-b]quinoline (Diastereomer 1), 100 μl tris-trimethylsilyl-silane and 1 mg azo-bis-isobutyro-nitrile are dissolved in 2 ml of toluene. Argon is bubbled through this solution for 5 minutes. Then the mixture is heated to 100° C. for 2 hours. Afterwards it is diluted with ethylacetate washed with brine and dried with magnesium sulphate. The solvents are evaporated in vacuo and the residue is chromatographed on silica gel (cyclohexane/ethylacetate 95:5 to 70:30).

Yield: 6 mg (67% of theory)
HPLC (Method 4): Retention time=3.11 min.
Mass spectrometry (ESI$^+$): m/z=574 [M+H]$^+$

151

Analogously to example XXV the following compounds are obtained:

(1) 8-(S)-8-(tert-Butyl-dimethyl-silanyloxy)-9-cyclopentyl-3,3,6,6-tetramethyl-1-(4-trifluoromethyl-phenyl)-1,3,5,6,7,8-hexahydro-furo[3,4-b]quinoline (Diastereomer 1)

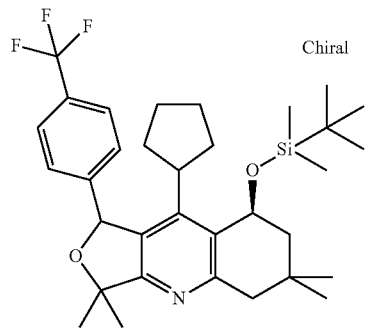 [SMILES: CC1(C)Cc2nc3c(c(C4CCCC4)c2[C@@H](O[Si](C)(C)C(C)(C)C)C1)C(c1ccc(C(F)(F)F)cc1)OC3(C)C]

8-(S)-8-(tert-Butyl-dimethyl-silanyloxy)-9-cyclopentyl-3,3,6,6-tetramethyl-1-(4-trifluoromethyl-phenyl)-1,3,5,6,7,8-hexahydro-furo[3,4-b]quinoline (Diastereomer 1) is also obtained starting from 8-(S)-8-(tert-Butyl-dimethyl-silanyloxy)-9-cyclopentyl-3-iodomethyl-3,6,6-trimethyl-1-(4-trifluoromethyl-phenyl)-1,3,5,6,7,8-hexahydro-furo[3,4-b]quinoline (Diastereomer 2).

HPLC (Method 4): Retention time=3.11 min.

Mass spectrometry (ESI$^+$): m/z=574 [M+H]$^+$ (2) 8-(S)-8-(tert-Butyl-dimethyl-silanyloxy)-9-cyclopentyl-3,3,6,6-tetramethyl-1-(4-trifluoromethyl-phenyl)-1,3,5,6,7,8-hexahydro-furo[3,4-b]quinoline (Diastereomer 2)

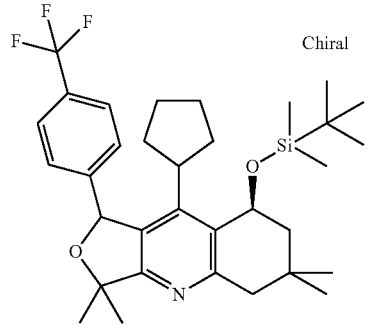 [SMILES: CC1(C)Cc2nc3c(c(C4CCCC4)c2[C@@H](O[Si](C)(C)C(C)(C)C)C1)C(c1ccc(C(F)(F)F)cc1)OC3(C)C]

Is obtained from a mixture of diastereomers of 8-(S)-8-(tert-Butyl-dimethyl-silanyloxy)-9-cyclopentyl-3-iodomethyl-3,6,6-trimethyl-1-(4-trifluoromethyl-phenyl)-1,3,5,6,7,8-hexahydro-furo[3,4-b]quinoline (Diastereomer 3) and 8-(S)-8-(tert-Butyl-dimethyl-silanyloxy)-9-cyclopentyl-3-iodomethyl-3,6,6-trimethyl-1-(4-trifluoromethyl-phenyl)-1,3,5,6,7,8-hexahydro-furo[3,4-b]quinoline (Diastereomer 4).

HPLC (Method 4): Retention time=3.06 min.

Mass spectrometry (ESI$^+$): m/z=574 [M+H]$^+$

152

Example XXVI

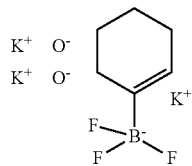

Potassium cyclohexenyltrifluoroborate

To 1 g 1-cyclohexylboronic acid in 20 ml of diethylether is added 1.86 g potassiumhydrogenefluoride and 0.86 ml water. Then the mixture is stirred over might at ambient temperature. The reaction is evaporated in vacuum and the residue is stirred with diethylether precipitate is filtered and dried under vacuum.

Yield: 2.3 g (97% of theory)

Mass spectrometry (EI): m/z=130 [M+]

Analogously to example XXVI the following compounds are obtained:

(1) Potassium cyclopentenyltrifluoroborate

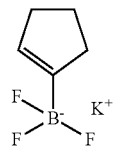

Mass spectrometry (EI): m/z=130 [M+]

Example XXVII

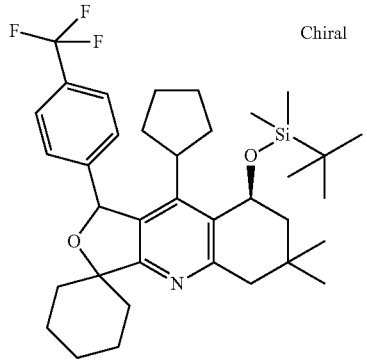 [SMILES: CC1(C)Cc2nc3c(c(C4CCCC4)c2[C@@H](O[Si](C)(C)C(C)(C)C)C1)C(c1ccc(C(F)(F)F)cc1)OC31CCCCC1]

(8'S)-8'-(tert-Butyldimethylsilyloxy)-9'-cyclopentyl-6',6'-dimethyl-1'-(4-(trifluoromethyl)phenyl)-5',6',7',8'-tetrahydro-1'H-spiro[cyclohexane-1,3'-furo[3,4-b]quinoline]

To 35 mg (8'S)-8'-(tert-Butyldimethylsilyloxy)-9'-cyclopentyl-2-iodo-6',6'-dimethyl-1-(4-(trifluoromethyl)phenyl)-5',6',7',8'-tetrahydro-1'H-spiro[cyclohexane-1,3'-furo[3,4-b]quinoline] and 25 μl triethylamine in 20 ml of methanol is added 10 mg palladium on charcoal (10%). Then the mixture is stirred under 50 psi hydrogen pressure at ambient temperature for 2 h. The reaction is filtered and evaporated under vacuum. The residue is purified by MPLC with a gradient of cyclohexane and ethylacetate.

Yield: 11 mg (38% of theory)
HPLC (Method 4): Retention time=3.4 min.
Mass spectrometry (ESI$^+$): m/z=614 [M+H]$^+$
Analogously to example XXVII the following compounds are obtained:

(1) (8'S)-8'-(tert-Butyldimethylsilyloxy)-9'-cyclopentyl-6',6'-dimethyl-1'-(4-(trifluoromethyl)phenyl)-5',6',7',8'-tetrahydro-1'H-spiro[cyclopentane-1,3'-furo[3,4-b]quinoline]

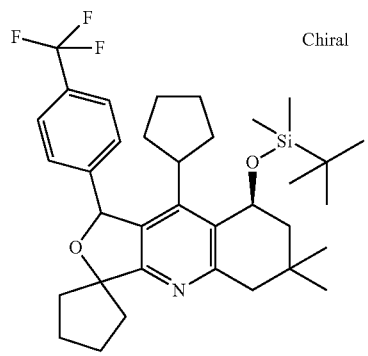

Mass spectrometry (ESI$^+$): m/z=614 [M+H]$^+$
R$_f$-value: 0.67 (silica gel, petrol ether/ethylacetate 8:1)
HPLC (Method 4): Retention time=3.30 min.

Example XXVIII

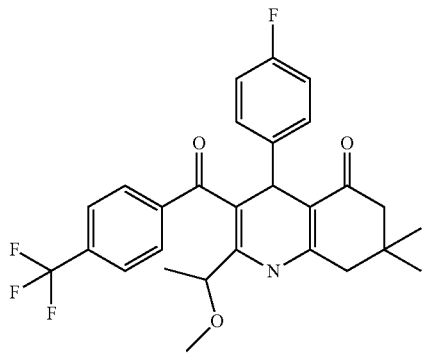 [SMILES: COC(C)C1=C(C(=O)c2ccc(C(F)(F)F)cc2)C(c2ccc(F)cc2)C2=C(CC(C)(C)CC2=O)N1]

4-(4-Fluorophenyl)-2-(1-methoxyethyl)-7,7-dimethyl-3-(4-(trifluoromethyl)benzoyl)-4,6,7,8-tetrahydroquinolin-5(1H)-one 6.4 g 3-Amino-4-methoxy-1-(4-trifluoromethyl-phenyl)-pent-2-en-1-one are dissolved in 25 ml of ethanol, 2.51 ml 4-fluorobenzaldehyde and 3.28 g 5,5-dimethyl-cyclohexane-1,3-dione and 270 mg DL-proline are successively added and the mixture is stirred for 30 minutes at room temperature. Then the mixture is heated for 24 hours to reflux at a deanstark trap. After cooling to room temperature the solvents are evaporated in vacuo. The residue is chromatographed on silica gel.

Yield: 3.7 g (31% of theory)

Mass spectrometry (ESI$^+$): m/z=502 [M+H]$^+$
HPLC (Method 9): Retention time=9.71 min.

Example XXIX

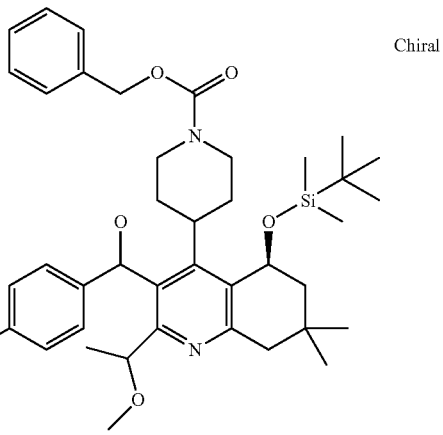

Benzyl 4-((5S)-5-(tert-butyldimethylsilyloxy)-3-(hydroxy(4-(trifluoromethyl)phenyl)methyl)-2-(1-methoxyethyl)-7,7-dimethyl-5,6,7,8-tetrahydroquinolin-4-yl)piperidine-1-carboxylate Diastereomer 1, Diastereomer 2 and Diastereomer 3

959 mg (6) Benzyl 4-((5S)-5-(tert-butyldimethylsilyloxy)-2-(1-methoxyethyl)-7,7-dimethyl-3-(4-(trifluoromethyl)benzoyl)-5,6,7,8-tetrahydroquinolin-4-yl)piperidine-1-carboxylate (Example VI (69) are dissolved in 15 ml ethanol. To the mixture 441 mg of sodiumborohydride is added. The reaction is stirred for 2 hours at 70° C. Then 8 equivalents of sodiumborohydride are added and the reaction is stirred over night at 70° C. The solvent is evaporated under vacuum. Water, ethylacetate and 1M hydrochloric acid are added. The aqueous phase is extracted with ethylacetate and the combined organic phases are washed with brine. After drying with natrium sulphate the solvents are evaporated under vacuum and the residue is chromatographed on isolate.

Yield: 307 mg (36% of theory)
Diastereomer 1, 2, 3 are obtained as a mixture.
Mass spectrometry (ESI$^+$): m/z=741 [M+H]$^+$
Diastereomer 1, Diastereomer 2 and Diastereomer 3 give retention times of 8.97, 9.45 and 9.63 by HPLC Method 10.

Example XXX

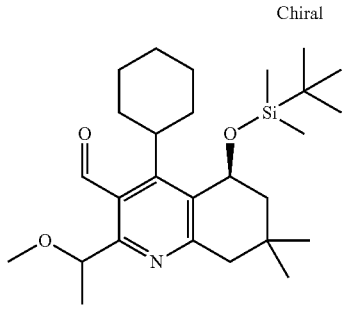 [SMILES: COC(C)c1nc2c(c(C3CCCCC3)c1C=O)[C@@H](O[Si](C)(C)C(C)(C)C)CC(C)(C)C2]

5-(S)-5-(tert-Butyl-dimethyl-silanyloxy)-4-cyclohexyl-2-(1-methoxy-ethyl)-7,7-dimethyl-5,6,7,8-tetrahydro-quinoline-3-carbaldehyde 769 mg 5-(S)-[5-(tert-Butyl-dimethyl-silanyloxy)-4-cyclohexyl-2-(1-methoxy-ethyl)-7,7-dimethyl-5,6,7,8-tetrahydro-quinolin-3-yl]-methanol are dissolved in 10 ml dichloromethane, cooled to 0° C. and treated with 801 mg Dess-Martin-Periodinan. After stirring for 48 hours, the mixture is allowed to warm to room temperature and aqueous sodium thiosulfate and saturated aqueous sodium bicarbonate solution is added. The mixture is stirred for 10 minutes, the phases are separated and the organic phase is evaporated in vacuo. The residue is treated with acetonitrile/water/trifluoroacetic acid (50:50:0.13) and the solid which precipitates is collected by filtration.

Yield: 463 mg (54% of theory)
Mass spectrometry (ESI$^+$): m/z=460 [M+H]$^+$

Example XXXI

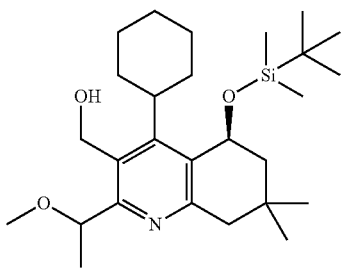

Chiral

5-(S)-[5-(tert-Butyl-dimethyl-silanyloxy)-4-cyclohexyl-2-(1-methoxy-ethyl)-7,7-dimethyl-5,6,7,8-tetrahydro-quinolin-3-yl]-methanol Under nitrogen 850 mg lithium aluminium hydride are dissolved in 50 ml tetrahydrofurane. The mixture is cooled to 4° C. and a solution of 1.18 g 5-(S)-5-(tert-Butyl-dimethyl-silanyloxy)-4-cyclohexyl-2-(1-methoxy-ethyl)-7,7-dimethyl-5,6,7,8-tetrahydro-quinoline-3-carboxylic acid ethyl ester in 10 ml tetrahydrofurane is added. The mixture is warmed to room temperature and stirred for 5 hours. After cooling to 0° C. 2 ml water in 10 ml tetrahydrofurane are added, followed by 10 ml of saturated aqueous sodium sulphate solution. The mixture is filtrated over celite and the filter cake is washed with tetrahydrofurane. The solvents are evaporated in vacuo, and the residue is triturated with petrol ether and the solids are collected by filtration.

Yield: 309 mg (29% of theory)
Mass spectrometry (ESI$^+$): m/z=462 [M+H]$^+$

Example XXXII

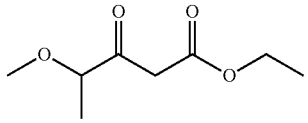

4-Methoxy-3-oxo-pentanoic acid ethyl ester 89 g ethyl potassium malonate are dissolved in 700 ml acetonitrile. While being stirred 109 ml triethylamine and 60 g magnesium chloride are added and the mixture is stirred for 2 hours. Then a solution of 1-imidazol-1-yl-2-methoxy-propan-1-one in 150 ml acetonitrile, prepared by mixing 27 g 2-methoxypropionic acid and 48 g carbonyldiimidazol in acetonitrile and stirring for 12 hours, is added and stirring is continued for 12 hours. 1 l of a 13% solution of hydrochloric acid is added while keeping the temperature below 25° C. and the mixture is stirred for 10 minutes. The phases are separated and the aqueous phase is extracted three times with ethylacetate. The combined organic phases are washed with saturated aqueous sodium bicarbonate and brine. After drying with magnesium sulphate the solvents are evaporated. The crude product is used directly in the next step.

Yield: 57 g (63% of theory)
Mass spectrometry (ESI$^+$): m/z=175 [M+H]$^+$

Example XXXII

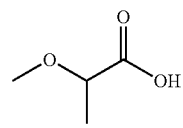

2-Methoxypropionic acid 50 g sodium hydride (60% in mineral oil) are dissolved in 600 ml tetrahydrofurane and cooled to 0° C. 98 g methyl-(S)-(−)-lactate in 150 ml tetrahydrofurane are added dropwise and stirring is continued for 20 minutes. Then 76 ml methyliodide in 100 ml tetrahydrofurane are added dropwise and the mixture is stirred for further 12 hours, while warming to room temperature. After cooling to 5° C. 400 ml of a 10 N solution of sodium hydroxide in water are added and the mixture is stirred for 2 hours. Then concentrated hydrochloric acid until pH of 1 is reached is added. The tetrahydrofurane is evaporated in vacuo and the aqueous phase is extracted three times with dichloromethane. The combined organic phases are dried with magnesium sulphate and the solvents are evaporated in vacuo. The crude product, which is obtained as a racemate under the reaction conditions, is used directly in the next step.

Yield: 65.6 g (67% of theory)
Mass spectrometry (ESI$^-$): m/z=103 [M−H]$^-$

Preparation of the Final Compounds

Example 1

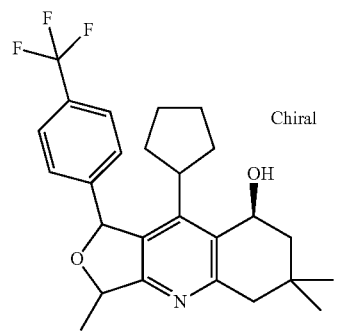

Chiral

8-(S)-9-Cyclopentyl-3,6,6-trimethyl-1-(4-trifluoromethyl-phenyl)-1,3,5,6,7,8-hexahydro-furo[3,4-b]quinolin-8-ol (Diastereomer 1)

80 mg 8-(S)-8-(tert-Butyl-dimethyl-silanyloxy)-9-cyclopentyl-3,6,6-trimethyl-1-(4-trifluoromethyl-phenyl)-1,3,5,6,7,8-hexahydro-furo[3,4-b]quinoline (Diastereomer 1) are dissolved in 6 ml tetrahydrofurane, cooled to 0° C. and 539 µl of a 1 M solution of tetrabutylammonium fluoride in tetrahydrofurane are added hereto dropwise. The mixture is stirred for 4 hours, diluted with ethylacetate and washed successively with water and brine. The organic phase is dried with magnesium sulphate, the solvents evaporated in vacuo and the residue chromatographed on silica gel (cyclohexane/ethylacetate 95:5 to 50:50).

Yield: 31 mg (48% of theory)
Mass spectrometry (ESI$^+$): m/z=446 [M+H]$^+$
HPLC (Method 3): Retention time=3.42 min.

The relative stereochemistry of the substituents on C-1 and C-9 is determined as trans by NOE-experiments.

Analogously to Example 1 the following compounds are obtained:

(1) 8-(S)-9-Cyclopentyl-3,6,6-trimethyl-1-(4-trifluoromethyl-phenyl)-1,3,5,6,7,8-hexahydro-furo[3,4-b]quinolin-8-ol (Diastereomer 2)

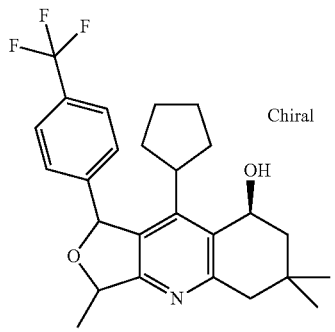 [SMILES: CC1OC(c2ccc(C(F)(F)F)cc2)c2c1nc1c(c2C2CCCC2)[C@@H](O)CC(C)(C)C1]

The compound is obtained starting from 8-(S)-8-(tert-Butyl-dimethyl-silanyloxy)-9-cyclopentyl-3,6,6-trimethyl-1-(4-trifluoromethyl-phenyl)-1,3,5,6,7,8-hexahydro-furo[3,4-b]quinoline (Diastereomer 2).

Mass spectrometry (ESI$^+$): m/z=446 [M+H]$^+$
HPLC (Method 3): Retention time=3.41 min.

The relative stereochemistry of the substituents on C-1 and C-9 is determined as cis by NOE-experiments.

The enantiomeric excess (ee) is determined by NMR analysis of the mosher ester to be 94%.

(2) 8-(S)-9-Cyclopentyl-3,6,6-trimethyl-1-(4-trifluoromethyl-phenyl)-1,3,5,6,7,8-hexahydro-furo[3,4-b]quinolin-8-ol (Diastereomer 3)

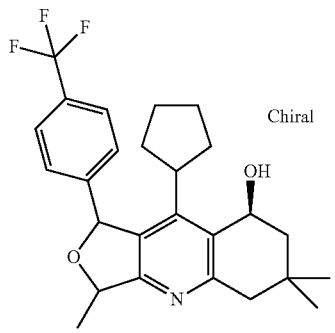

and 8-(S)-9-Cyclopentyl-3,6,6-trimethyl-1-(4-trifluoromethyl-phenyl)-1,3,5,6,7,8-hexahydro-furo[3,4-b]quinolin-8-ol (Diastereomer 4)

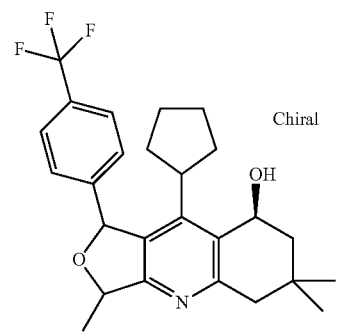

The compounds are obtained starting from example VIII (1). The diastereomers are separated by chromatography on silica gel (cyclohexane/ethylacetate 95:5 to 10:90).

8-(S)-9-Cyclopentyl-3,6,6-trimethyl-1-(4-trifluoromethyl-phenyl)-1,3,5,6,7,8-hexahydro-furo[3,4-b]quinolin-8-ol (Diastereomer 3) (elutes as first product from silica gel column)

Mass spectrometry (ESI$^+$): m/z=446 [M+H]$^+$
HPLC (Method 3): Retention time=3.43 min.

The relative stereochemistry of the substituents on C-1 and C-9 is determined as trans by NOE-experiments.

8-(S)-9-Cyclopentyl-3,6,6-trimethyl-1-(4-trifluoromethyl-phenyl)-1,3,5,6,7,8-hexahydro-furo[3,4-b]quinolin-8-ol (Diastereomer 4) (elutes as second product from silica gel column)

Mass spectrometry (ESI$^+$): m/z=446 [M+H]$^+$
HPLC (Method 3): Retention time=3.42 min.

The relative stereochemistry of the substituents on C-1 and C-9 is determined as cis by NOE-experiments.

(3) 8-(S)-9-Cyclopentyl-6,6-dimethyl-1-(4-trifluoromethyl-phenyl)-1,3,5,6,7,8-hexahydro-furo[3,4-b]quinolin-8-ol (Diastereomer 1)

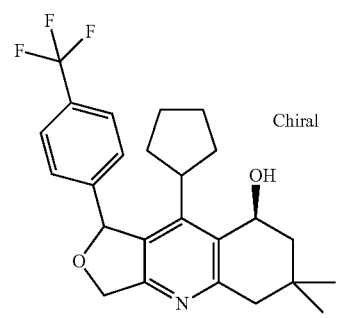

and 8-(S)-9-Cyclopentyl-6,6-dimethyl-1-(4-trifluoromethyl-phenyl)-1,3,5,6,7,8-hexahydro-furo[3,4-b]quinolin-8-ol (Diastereomer 2)

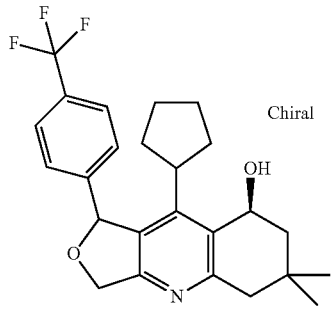 [SMILES: CC1(C)Cc2nc3c(c(C4CCCC4)c2[C@@H](O)C1)C(c1ccc(C(F)(F)F)cc1)OC3]

Obtained starting from the diastereomeric mixture from example IX. The products can be separated by chromatography on silica gel (cyclohexane/ethylacetate 95:5 to 50:50).

8-(S)-9-Cyclopentyl-6,6-dimethyl-1-(4-trifluoromethyl-phenyl)-1,3,5,6,7,8-hexahydro-furo[3,4-b]quinolin-8-ol (Diastereomer 1)

Mass spectrometry (ESI+): m/z=432 [M+H]+

$R_f$-value: 0.76 (silica gel, petrole ether/ethylacetate 1:1)

8-(S)-9-Cyclopentyl-6,6-dimethyl-1-(4-trifluoromethyl-phenyl)-1,3,5,6,7,8-hexahydro-furo[3,4-b]quinolin-8-ol (Diastereomer 2)

Mass spectrometry (ESI+): m/z=432 [M+H]+

$R_f$-value: 0.53 (silica gel, petrole ether/ethylacetate 1:1)

(4) 9-Cyclopentyl-3,3,6,6-tetramethyl-1-(4-trifluoromethyl-phenyl)-1,3,5,6,7,8-hexahydro-furo[3,4-b]quinolin-8-ol

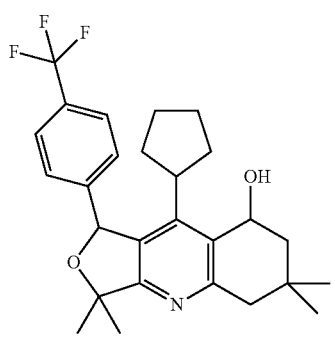 [SMILES: CC1(C)Cc2nc3c(c(C4CCCC4)c2C(O)C1)C(c1ccc(C(F)(F)F)cc1)OC3(C)C]

The product is obtained as a single diastereomer starting from 8-(tert-butyl-dimethyl-silanyloxy)-9-cyclopentyl-3,3,6,6-tetramethyl-1-(4-trifluoromethyl-phenyl)-1,3,5,6,7,8-hexahydro-furo[3,4-b]quinoline (example XXII).

Mass spectrometry (ESI+): m/z=460 [M+H]+

HPLC (Method 4): Retention time=2.06 min.

(5) 8-(S)-9-Cyclopentyl-3,3,6,6-tetramethyl-1-(4-trifluoromethyl-phenyl)-1,3,5,6,7,8-hexahydro-furo[3,4-b]quinolin-8-ol (Diastereomer 1)

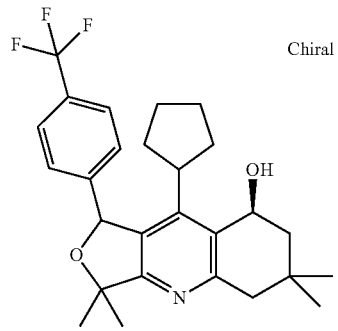 [SMILES: CC1(C)Cc2nc3c(c(C4CCCC4)c2[C@@H](O)C1)C(c1ccc(C(F)(F)F)cc1)OC3(C)C]

The product is obtained as a single diastereomer starting from 8-(S)-8-(tert-Butyl-dimethyl-silanyloxy)-9-cyclopentyl-3,3,6,6-tetramethyl-1-(4-trifluoromethyl-phenyl)-1,3,5,6,7,8-hexahydro-furo[3,4-b]quinoline (Diastereomer 1) (example XXV).

HPLC (Method 4): Retention time=2.04 min.

Mass spectrometry (ESI+): m/z=460 [M+H]+

(6) 8-(S)-9-Cyclopentyl-3,3,6,6-tetramethyl-1-(4-trifluoromethyl-phenyl)-1,3,5,6,7,8-hexahydro-furo[3,4-b]quinolin-8-ol (Diastereomer 2)

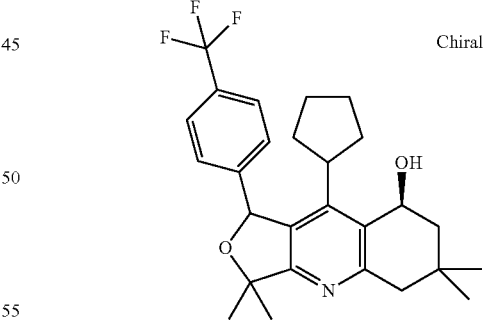

The product is obtained as a single diastereomer starting from 8-(S)-8-(tert-Butyl-dimethyl-silanyloxy)-9-cyclopentyl-3,3,6,6-tetramethyl-1-(4-trifluoromethyl-phenyl)-1,3,5,6,7,8-hexahydro-furo[3,4-b]quinoline (Diastereomer 2) (example XXV).

$R_f$-value: 0.43 (silica gel, petrole ether/ethylacetate 2:1)

Mass spectrometry (ESI+): m/z=460 [M+H]+

(7) 8-(S)-9-Cyclohexyl-3,6,6-trimethyl-1-(4-trifluoromethyl-phenyl)-1,3,5,6,7,8-hexahydro-furo[3,4-b]quinolin-8-ol (Diastereomer 1)

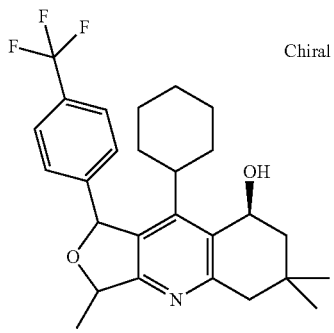 [SMILES: CC1OC(c2ccc(C(F)(F)F)cc2)c2c1nc1c(c2C2CCCCC2)[C@@H](O)CC(C)(C)C1]

The product is obtained as a single diastereomer starting from 8-(S)-8-(tert-Butyl-dimethyl-silanyloxy)-9-cyclohexyl-3,6,6-trimethyl-1-(4-trifluoromethyl-phenyl)-1,3,5,6,7,8-hexahydro-furo[3,4-b]quinoline (Diastereomer 1) (example IX (1)).

Mass spectrometry (ESI⁺): m/z=460 [M+H]⁺

HPLC (Method 8): Retention time=9.80 min.

(8) (1'S,8'S)-9'-Cyclopentyl-6',6'-dimethyl-1'-(4-(trifluoromethyl)phenyl)-5',6',7',8'-tetrahydro-1'H-spiro[cyclohexane-1,3'-furo[3,4-b]quinolin]-8'-ol

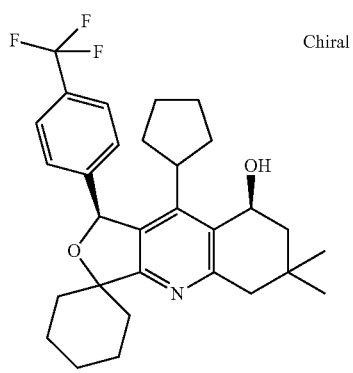 [SMILES: CC1(C)Cc2nc3c(c(C4CCCC4)c2[C@@H](O)C1)[C@H](c1ccc(C(F)(F)F)cc1)OC31CCCCC1]

The product is obtained as a single diastereomer starting from (8'S)-8'-(tert-Butyldimethylsilyloxy)-9'-cyclopentyl-6',6'-dimethyl-1'-(4-(trifluoromethyl)phenyl)-5',6',7',8'-tetrahydro-1'H-spiro[cyclohexane-1,3'-furo[3,4-b]quinoline] (example XXVII).

Mass spectrometry (ESI⁺): m/z=500 [M+H]⁺

HPLC (Method 4): Retention time=2.34 min.

R$_f$-value: 0.42 (silica gel, petrol ether/ethylacetate 1:1)

(9) (1'R,8'S)-9'-Cyclopentyl-6',6'-dimethyl-1'-(4-(trifluoromethyl)phenyl)-5',6',7',8'-tetrahydro-1'H-spiro[cyclohexane-1,3'-furo[3,4-b]quinolin]-8'-ol

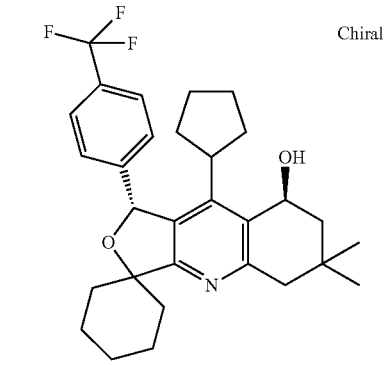 [SMILES: CC1(C)Cc2nc3c(c(C4CCCC4)c2[C@@H](O)C1)[C@@H](c1ccc(C(F)(F)F)cc1)OC31CCCCC1]

The product is obtained as a single diastereomer starting from (8'S)-8'-(tert-butyldimethylsilyloxy)-9'-cyclopentyl-6',6'-dimethyl-1'-(4-(trifluoromethyl)phenyl)-5',6',7',8'-tetrahydro-1'H-spiro[cyclohexane-1,3'-furo[3,4-b]quinoline] (example XXVII).

Mass spectrometry (ESI⁺): m/z=500 [M+H]⁺

HPLC (Method 4): Retention time=2.35 min.

R$_f$-value: 0.28 (silica gel, petrol ether/ethylacetate 4:1)

(10) (1'S,8'S)-9'-Cyclopentyl-6',6'-dimethyl-1'-(4-(trifluoromethyl)phenyl)-5',6',7',8'-tetrahydro-1'H-spiro[cyclopentane-1,3'-furo[3,4-b]quinolin]-8'-ol

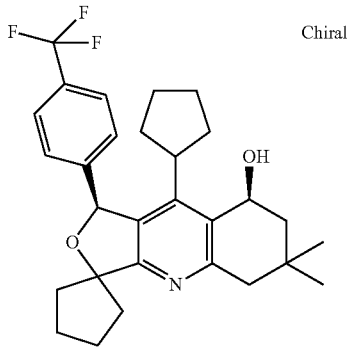 [SMILES: CC1(C)Cc2nc3c(c(C4CCCC4)c2[C@@H](O)C1)[C@H](c1ccc(C(F)(F)F)cc1)OC31CCCC1]

The product is obtained as a single diastereomer starting from (8'S)-8'-(tert-butyldimethylsilyloxy)-9'-cyclopentyl-6',6'-dimethyl-1'-(4-(trifluoromethyl)phenyl)-5',6',7',8'-tetrahydro-1'H-spiro[cyclopentane-1,3'-furo[3,4-b]quinoline] (example XXVII(1)).

Mass spectrometry (ESI⁺): m/z=486 [M+H]⁺

HPLC (Method 4): Retention time=2.23 min.

R$_f$-value: 0.39 (silica gel, petrol ether/ethylacetate 4:1)

(11) (1'R,8'S)-9'-Cyclopentyl-6',6'-dimethyl-1'-(4-(trifluoromethyl)phenyl)-5',6',7',8'-tetrahydro-1'H-spiro[cyclopentane-1,3'-furo[3,4-b]quinolin]-8'-ol

(13) (8S)-3,6,6-Trimethyl-9-(tetrahydro-2H-pyran-4-yl)-1-(4-(trifluoromethyl)phenyl)-1,3,5,6,7,8-hexahydrofuro[3,4-b]quinolin-8-ol

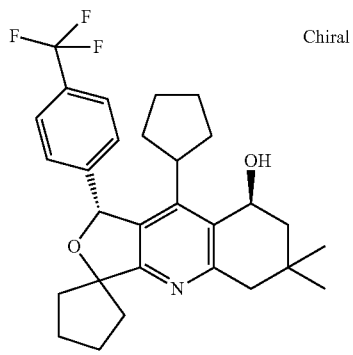 [SMILES: CC1(C)Cc2nc3c(c(C4CCCC4)c2[C@@H](O)C1)[C@@H](c1ccc(C(F)(F)F)cc1)OC31CCCC1]

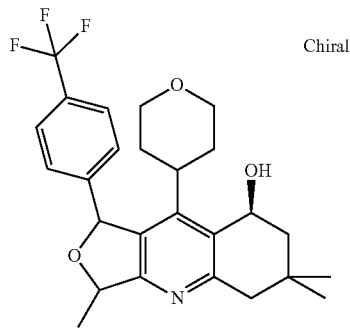

The product is obtained as a single diastereomer starting from (8'S)-8'-(tert-butyldimethylsilyloxy)-9'-cyclopentyl-6',6'-dimethyl-1'-(4-(trifluoromethyl)phenyl)-5',6',7',8'-tetrahydro-1'H-spiro[cyclopentane-1,3'-furo[3,4-b]quinoline] (example XXVII(1)).

Mass spectrometry (ESI$^+$): m/z=486 [M+H]$^+$

HPLC (Method 4): Retention time=2.25 min.

$R_f$-value: 0.23 (silica gel, petrol ether/ethylacetate 4:1)

(12) (8S)-9-(4-Fluorophenyl)-3,6,6-trimethyl-1-(4-(trifluoromethyl)phenyl)-1,3,5,6,7,8-hexahydrofuro[3,4-b]quinolin-8-ol The product is obtained as a single diastereomer starting from (8S)-8-(tert-butyldimethylsilyloxy)-3,6,6-trimethyl-9-(tetrahydro-2H-pyran-4-yl)-1-(4-(trifluoromethyl)phenyl)-1,3,5,6,7,8-hexahydrofuro[3,4-b]quinoline (example IX (3)).

Mass spectrometry (ESI$^+$): m/z=462 [M+H]$^+$

HPLC (Method 9): Retention time=7.52 min.

(14) Benzyl-4-((8S)-8-hydroxy-3,6,6-trimethyl-1-(4-(trifluoromethyl)phenyl)-1,3,5,6,7,8-hexahydrofuro[3,4-b]quinolin-9-yl)piperidine-1-carboxylate

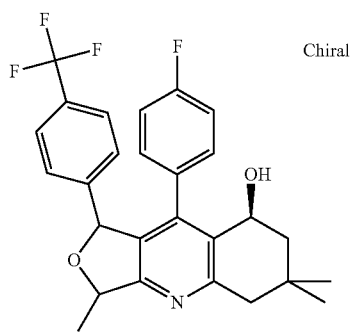 [SMILES: CC1OC(c2ccc(C(F)(F)F)cc2)c2c1nc1c(c2-c2ccc(F)cc2)[C@@H](O)CC(C)(C)C1]

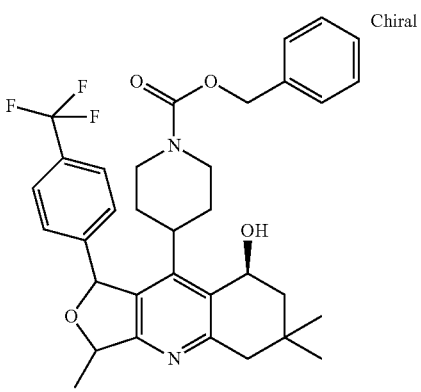 [SMILES: CC1OC(c2ccc(C(F)(F)F)cc2)c2c1nc1c(c2C2CCN(C(=O)OCc3ccccc3)CC2)[C@@H](O)CC(C)(C)C1]

The product is obtained as a single diastereomer starting from a mixture of diastereomers (8S)-8-(tert-butyldimethylsilyloxy)-9-(4-fluorophenyl)-3,6,6-trimethyl-1-(4-(trifluoromethyl)phenyl)-1,3,5,6,7,8-hexahydrofuro[3,4-b]quinoline (example IX (8)).

Mass spectrometry (ESI$^+$): m/z=472 [M+H]$^+$

HPLC (Method 9): Retention time=9.25 min

The product is obtained as a single diastereomer starting from (benzyl-4-((8S)-8-(tert-butyldimethylsilyloxy)-3,6,6-trimethyl-1-(4-(trifluoromethyl)phenyl)-1,3,5,6,7,8-hexahydrofuro[3,4-b]quinolin-9-yl)piperidine-1-carboxylate (example IX (4)).

Mass spectrometry (ESI$^+$): m/z=595 [M+H]$^+$

HPLC (Method 10): Retention time=9.54 min.

(15) (8S)-9-Cyclopentyl-3,6,6-trimethyl-1-(3-(trifluoromethyl)phenyl)-1,3,5,6,7,8-hexahydrofuro[3,4-b]quinolin-8-ol

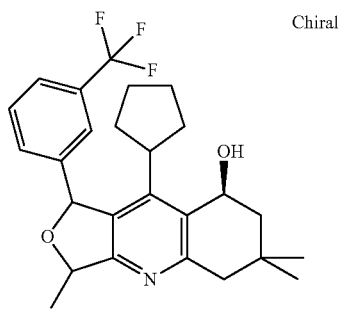 [SMILES: CC1OC(c2cccc(C(F)(F)F)c2)c2c1nc1c(c2C2CCCC2)[C@@H](O)CC(C)(C)C1]

The product is obtained as a single diastereomer starting from ((5S)-5-(tert-butyldimethylsilyloxy)-4-cyclopentyl-2-(1-methoxyethyl)-7,7-dimethyl-5,6,7,8-tetrahydroquinolin-3-yl)-(3-(trifluoromethyl)phenyl)methanol (Diastereomer 1) (example IX (5)).
Mass spectrometry (ESI$^+$): m/z=446 [M+H]$^+$
HPLC (Method 9): Retention time=8.84 min.

(16) (8S)-9-Isopropyl-3,6,6-trimethyl-1-(4-(trifluoromethyl)phenyl)-1,3,5,6,7,8-hexahydrofuro[3,4-b]quinolin-8-ol

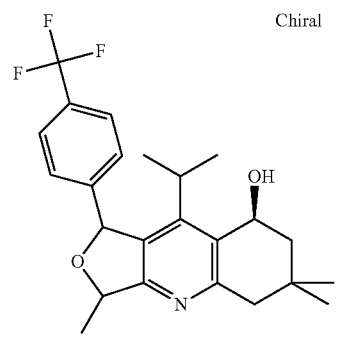 [SMILES: CC(C)c1c2c(nc3c1[C@@H](O)CC(C)(C)C3)C(C)OC2c1ccc(C(F)(F)F)cc1]

The product is obtained as a single diastereomer starting from (8S)-8-(tert-butyldimethylsilyloxy)-9-isopropyl-3,6,6-trimethyl-1-(4-(trifluoromethyl)phenyl)-1,3,5,6,7,8-hexahydrofuro[3,4-b]quinolin (example IX (6)).
Mass spectrometry (ESI$^+$): m/z=420 [M+H]$^+$
HPLC (Method 9): Retention time=8.15 min.

Example 2

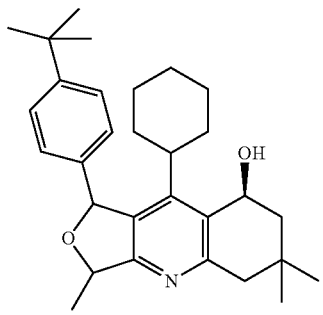 [SMILES: CC1OC(c2ccc(C(C)(C)C)cc2)c2c1nc1c(c2C2CCCCC2)[C@@H](O)CC(C)(C)C1]

8-(S)-1-(4-tert-Butyl-phenyl)-9-cyclohexyl-3,6,6-trimethyl-1,3,5,6,7,8-hexahydro-furo[3,4b]quinolin-8-ol 37 mg of 5-(S)-[5-(tert-Butyl-dimethyl-silanyloxy)-4-cyclohexyl-2-(1-methoxy-ethyl)-7,7-dimethyl-5,6,7,8-tetrahydro-quinolin-3-yl]-(4-tert-butyl-phenyl)-methanol (example VII (9)) are dissolved in 0.50 ml tetrahydrofurane and 46 mg tetrabutylammonium iodide are added. The mixture is cooled to −20° C. and 42 μl diethylaminosulfurtrichloride (DAST) are added. The mixture is allowed to warm to room temperature and stirred for 12 hours. 2 ml tetrahydrofurane are added and stirring is continued for further 24 hours. The mixture is diluted with water and ethylacetate and the organic phase is separated. The organic phase is washed with 1 N hydrochloric acid, dried and the solvent evaporated. The remainder is dissolved in acetonitrile/methanol/water and purified by HPLC (eluent A: water+0.13% TFA, eluent B: acetonitrile).
Yield: 1.6 mg (3.8% of theory)
Mass spectrometry (ESI$^+$): m/z=448 [M+H]$^+$
HPLC (Method 11): Retention time=1.81 min.

Some examples of formulations will now be described in which the term "active substance" denotes one or more compounds according to the invention, including the salts thereof. In the case of one of the combinations with one or additional active substances as described previously, the term "active substance" also includes the additional active substances.

Example A

Tablets Containing 100 mg of active substance

Composition:

| 1 tablet contains: | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:
The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

| Weight of tablet: | 220 mg |
|---|---|
| Diameter: | 10 mm, biplanar, facetted on both sides and notched on one side. |

Example B

Tablets Containing 150 mg of Active Substance

Composition:

| 1 tablet contains: | |
|---|---|
| active substance | 150.0 mg |
| powdered lactose | 89.0 mg |
| corn starch | 40.0 mg |
| colloidal silica | 10.0 mg |

167
-continued

| 1 tablet contains: | |
|---|---|
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

| Weight of tablet: | 300 mg |
|---|---|
| die: | 10 mm, flat |

Example C

Hard Gelatine Capsules Containing 150 mg of Active Substance

Composition:

| 1 capsule contains: | |
|---|---|
| active substance | 150.0 mg |
| corn starch (dried) | approx. 180.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

| Capsule filling: | approx. 320 mg |
|---|---|
| Capsule shell: | size 1 hard gelatine capsule. |

Example D

Suppositories Containing 150 mg of Active Substance

Composition:

| 1 suppository contains: | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

Example E

Ampoules Containing 10 mg Active Substance

Composition:

| active substance | 10.0 mg |
|---|---|
| 0.01N hydrochloric acid | q.s. |
| double-distilled water | ad 2.0 ml |

Preparation:

The active substance is dissolved in the necessary amount of 0.01 N HCl, made isotonic with common salt, filtered sterile and transferred into 2 ml ampoules.

Example F

Ampoules Containing 50 mg of Active Substance

Composition:

| active substance | 50.0 mg |
|---|---|
| 0.01N hydrochloric acid | q.s. |
| double-distilled water | ad 10.0 ml |

Preparation:

The active substance is dissolved in the necessary amount of 0.01 N HCl, made isotonic with common salt, filtered sterile and transferred into 10 ml ampoules.

The invention claimed is:

1. A compound of formula I wherein
$R^1$ is phenyl substituted by a group selected from $R^{11}$, $R^{12}$, and $R^{13}$ or a combination thereof, or pyridyl substituted by $R^{11}$, in which
$R^{11}$ is fluorine, tert-butyl, trifluoromethyl or trifluoromethoxy,
$R^{12}$ is fluorine or trifluoromethyl,
$R^{13}$ is fluorine,
either
$R^2$ is ethyl, propyl or isopropyl, and
$R^3$ is hydrogen,
or
$R^2$ is methyl, and
$R^3$ is hydrogen,
or
$R^2$ is methyl, and
$R^3$ is methyl,
or
$R^2$ is hydrogen, and
$R^3$ is hydrogen, or R² and R³ together and with inclusion of the carbon atom, to which they are attached, form a cyclopentane ring,
or R² and R³ together and with inclusion of the carbon atom, to which they are attached, form a cyclohexane ring,
either
R⁴ is isopropyl or isobutyl, and
R⁵ is hydrogen,
or
R⁴ is methyl, and
R⁵ is methyl,
or
R⁴ is hydrogen, and
R⁵ is hydrogen,
or R⁴ and R⁵ together and with inclusion of the carbon atom, to which they are attached, form a cyclopropane, cyclobutane, cyclopentane or cyclohexane ring,
either
R⁶ is fluorine or methoxy, and
R⁷ is hydrogen,
or
R⁶ is hydroxyl, and
R⁷ is methyl,
or
R⁶ is hydroxyl, and
R⁷ is hydrogen,
or R⁶ and R⁷ taken together and with the carbon atom, to which they are bonded, form a carbonyl (>C=O) or oxime (>C=N—OH) group,
R⁸ is 1-4C-alkyl, cyclopropyl, cyclobutyl, cyclopentyl, cyclohexyl, cyclopentenyl, cyclohexenyl, tetrahydropyranyl, or phenyl substituted by a group selected from R⁸¹ and R⁸² or a combination thereof, in which
R⁸¹ is fluorine, methyl, trifluoromethyl, methoxy or trifluoromethoxy,
R⁸² is fluorine or trifluoromethyl,
or a tautomer, stereoisomer, mixture thereof or a salt thereof.

2. The compound of formula I according to claim 1, wherein
R¹ is trifluoromethyl-phenyl,
either
R² is ethyl, and
R³ is hydrogen,
or
R² is isopropyl, and
R³ is hydrogen,
or
R² is methyl, and
R³ is hydrogen,
or
R² is methyl, and
R³ is methyl,
or R² and R³ together and with inclusion of the carbon atom, to which they are attached, form a cyclopentane ring,
or R² and R³ together and with inclusion of the carbon atom, to which they are attached, form a cyclohexane ring,
either
R⁴ is methyl, and
R⁵ is methyl,
or R⁴ and R⁵ together and with inclusion of the carbon atom, to which they are attached, form a cyclopropane ring, or R⁴ and R⁵ together and with inclusion of the carbon atom, to which they are attached, form a cyclobutane ring,
or R⁴ and R⁵ together and with inclusion of the carbon atom, to which they are attached, form a cyclopentane ring,
or R⁴ and R⁵ together and with inclusion of the carbon atom, to which they are attached, form a cyclohexane ring,
R⁶ is hydroxyl,
R⁷ is hydrogen,
R⁸ is isopropyl, cyclopropyl, cyclobutyl, cyclopentyl, cyclohexyl, tetrahydropyranyl, or fluorophenyl,
or a tautomer, stereoisomer, mixture thereof or a salt thereof.

3. The compound according to claim 1 which is of formula I*

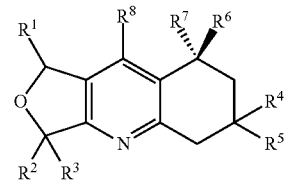

comprising one or more of the following:
R¹ is 4-trifluoromethyl-phenyl or 3-trifluoromethyl-phenyl;
R² is methyl, and
R³ is methyl, or
R² is methyl, and
R³ is hydrogen, or
R² and R³ together and with inclusion of the carbon atom, to which they are attached, form a cyclopentane ring, or
R² and R³ together and with inclusion of the carbon atom, to which they are attached, form a cyclohexane ring;
R⁴ is methyl, and
R⁵ is methyl;
R⁶ is hydroxyl, and
R⁷ is hydrogen;
and
R⁸ is isopropyl, cyclopentyl, cyclohexyl, tetrahydropyran-4-yl or 4-fluorophenyl;
or a tautomer, stereoisomer, mixture thereof or a salt thereof.

4. The compound according to claim 3 comprising one or more of the following:
R¹ is 4-trifluoromethyl-phenyl;
either
R² is methyl, and
R³ is methyl,
or
R² is methyl, and
R³ is hydrogen;
R⁴ is methyl, and
R⁵ is methyl;
R⁶ is hydroxyl, and
R⁷ is hydrogen;
and
R⁸ is cyclopentyl or cyclohexyl;
or a tautomer, stereoisomer, mixture thereof or a salt thereof.

5. The compound according to claim 1 wherein
R² is methyl, and
R³ is methyl, or a tautomer, stereoisomer, mixture thereof or a salt thereof.

6. The compound according to claim 1 wherein R$^2$ and R$^3$ together and with inclusion of the carbon atom, to which they are attached, form a cyclopentane ring, or a tautomer, stereoisomer, mixture thereof or a salt thereof.

7. The compound according to claim 1 wherein R$^2$ and R$^3$ together and with inclusion of the carbon atom, to which they are attached, form a cyclohexane ring, or a tautomer, stereoisomer, mixture thereof or a salt thereof.

8. The compound according to claim 1 which is of formula Ie*

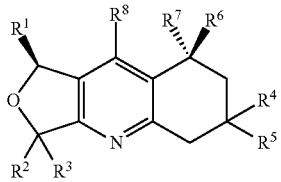

(Ie*)

or a tautomer, stereoisomer, mixture thereof or a salt thereof.

9. The compound according to claim 1 wherein R$^2$ is methyl, and R$^3$ is hydrogen, or a tautomer, stereoisomer, mixture thereof or a salt thereof.

10. The compound according to claim 9 which is of formula Ia*

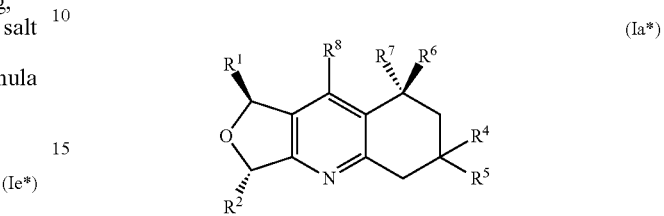

(Ia*)

or a tautomer, stereoisomer, mixture thereof or a salt thereof.

11. A pharmaceutical composition, comprising a compound of formula I according to claim 1 or a physiologically acceptable salt thereof, optionally together with one or more inert carriers, diluents, or any combination thereof.

* * * * *